United States Patent
Könemann et al.

(10) Patent No.: US 9,790,423 B2
(45) Date of Patent: Oct. 17, 2017

(54) CYANATED NAPHTHALENEBENZIMIDAZOLE COMPOUNDS

(71) Applicant: BASF SE, Ludwigshafen (DE)

(72) Inventors: Martin Könemann, Mannheim (DE); Gabriele Mattern, Schifferstadt (DE); Gerhard Wagenblast, Wachenheim (DE); Sorin Ivanovici, Heidelberg (DE); Robert Send, Karlsruhe (DE)

(*) Notice: Subject to any disclaimer, the term of this patent is extended or adjusted under 35 U.S.C. 154(b) by 0 days.

(21) Appl. No.: 14/910,078

(22) PCT Filed: Aug. 4, 2014

(86) PCT No.: PCT/IB2014/063674
§ 371 (c)(1),
(2) Date: Feb. 4, 2016

(87) PCT Pub. No.: WO2015/019270
PCT Pub. Date: Feb. 12, 2015

(65) Prior Publication Data
US 2016/0177177 A1   Jun. 23, 2016

(30) Foreign Application Priority Data
Aug. 5, 2013 (EP) .................................... 13179303

(51) Int. Cl.
| C07D 471/04 | (2006.01) |
| C07D 471/06 | (2006.01) |
| C09K 11/06 | (2006.01) |
| H01L 33/50 | (2010.01) |
| H01L 31/0232 | (2014.01) |
| H01L 51/00 | (2006.01) |
| H01L 51/52 | (2006.01) |

(52) U.S. Cl.
CPC ............ *C09K 11/06* (2013.01); *C07D 471/04* (2013.01); *C07D 471/06* (2013.01); *H01L 31/02322* (2013.01); *H01L 33/502* (2013.01); *H01L 51/0072* (2013.01); *H01L 51/5262* (2013.01); *C09K 2211/1007* (2013.01); *C09K 2211/1044* (2013.01); *Y02E 10/52* (2013.01)

(58) Field of Classification Search
CPC .... C07D 471/04; C07D 471/06; C09K 11/06; C09K 2211/1007; C09K 2211/1044; H01L 31/02322; H01L 33/502; H01L 51/0072; H01L 51/5262
USPC ................... 546/52; 252/301.35; 257/40, 98; 136/257
See application file for complete search history.

(56) References Cited

U.S. PATENT DOCUMENTS

| 2,820,037 A * | 1/1958 | Schmidt-Nickels .... C09B 57/12 546/52 |
| 9,105,410 B2 | 8/2015 | Wonneberger et al. |
| 9,389,315 B2 | 7/2016 | Bruder et al. |
| 2014/0012002 A1 | 1/2014 | Bruder et al. |

(Continued)

FOREIGN PATENT DOCUMENTS

| DE | 2408044 A1 | 9/1975 |
| JP | 2004006064 A | 1/2004 |
| WO | WO2012168395 | * 12/2012 |
| WO | WO-2012168395 A1 | 12/2012 |
| WO | WO-2013018041 A1 | 2/2013 |
| WO | WO-2014111365 A1 | 7/2014 |
| WO | WO-2014147525 A2 | 9/2014 |

OTHER PUBLICATIONS

Schmidt "Benzimidazoben . . . " CA52:45643 (1958).*
Mamada et al. "Benzimidazole derivatives . . . " Chem. Eur. J. 20 pp. 11835-11846 (2014).*
Lack et al. "Targeting the ginding . . . " CA156:564 (2011).*
International Search Report for PCT/IB2014/063674 mailed Jan. 6, 2015.

*Primary Examiner* — Celia Chang
(74) *Attorney, Agent, or Firm* — Drinker Biddle & Reath LLP

(57) ABSTRACT

The present invention relates to cyanated naphthalenebenzimidazole compounds of the formula (I) and mixtures thereof, in which $R^1$, $R^2$, $R^3$, $R^4$, $R^5$, $R^6$, $R^7$, $R^8$, $R^9$ and $R^{10}$ are each independently hydrogen, cyano or aryl which is unsubstituted or has one or more identical or different substituents $R^{Ar}$, where $R^{Ar}$ is as defined in the claims and in the description, with the proviso that the compounds of the formula I comprise at least one cyano group. The invention further relates to color converters comprising at least one polymer as a matrix material and at least one cyanated naphthalenebenzimidazole compound or mixtures thereof as a fluorescent dye, to the use of the color converters and to lighting devices comprising at least one LED and at least one color converter.

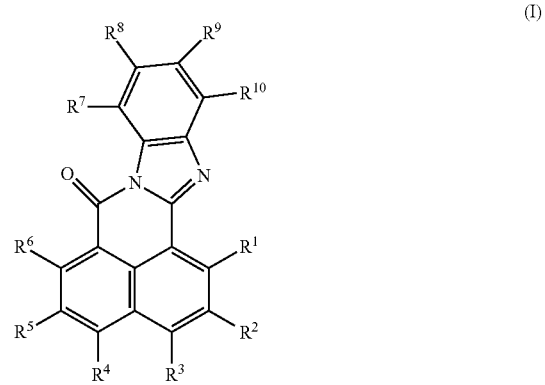

17 Claims, 1 Drawing Sheet

(56) References Cited

U.S. PATENT DOCUMENTS

| | | |
|---|---|---|
| 2014/0252280 A1 | 9/2014 | Schaefer et al. |
| 2014/0301935 A1 | 10/2014 | Ivanovici et al. |
| 2015/0005497 A1 | 1/2015 | Murer et al. |
| 2015/0108415 A1 | 4/2015 | Send et al. |
| 2015/0207083 A1 | 7/2015 | Schaefer et al. |
| 2015/0243907 A1 | 8/2015 | Wolleb et al. |
| 2015/0284569 A1 | 10/2015 | Wonneberger et al. |
| 2015/0318501 A1 | 11/2015 | Watanabe et al. |
| 2016/0072081 A1 | 3/2016 | Metz et al. |
| 2016/0099429 A1 | 4/2016 | Bruder et al. |
| 2016/0141521 A1 | 5/2016 | Watanabe et al. |
| 2016/0177177 A1 | 6/2016 | Konemann et al. |

\* cited by examiner

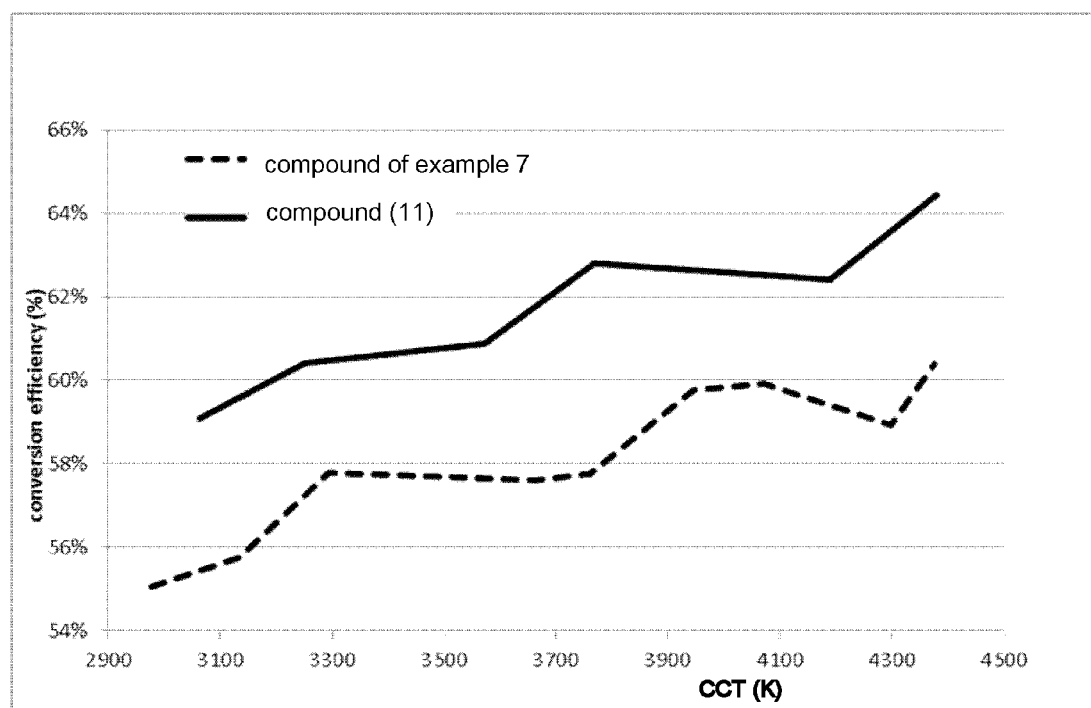

CYANATED NAPHTHALENEBENZIMIDAZOLE COMPOUNDS

CROSS-REFERENCE TO RELATED APPLICATIONS

This application is a national stage application (under 35 U.S.C. §371) of PCT/IB2014/063674, filed Aug. 5, 2014, which claims benefit of European Application No. 13179303.6, filed Aug. 5, 2013, both of which are incorporated herein by reference in their entirety.

The present invention relates to novel cyanated naphthalenebenzimidazole compounds and mixtures thereof, to processes for preparation thereof, to color converters comprising at least one polymer as a matrix material and at least one cyanated naphthalenebenzimidazole compound or mixtures thereof as a fluorescent dye, to the use of the color converters and to lighting devices comprising at least one LED and at least one color converter.

Because of their low energy consumption, LEDs (light-emitting diodes, LEDs) are increasingly being used as a light source for general lighting, for example in offices and residences, or for architectural lighting, in information signs, small appliances, and in the automobile and aircraft industries. Light emission is based on the recombination of electron-hole pairs (excitons) in the junction region of a pn junction poled in forward direction in a semiconductor. The size of the band gap of this semiconductor determines the approximate wavelength of the light emitted. In order to generate a particular color, LEDs with different band gaps can be combined to form a multi-LED.

Alternatively, a radiation conversion luminophore (also referred to as phosphor, or fluorescent colorant or fluorescent dye) can also be combined with an LED. In this context, the radiation emitted by the LED is partly absorbed by the radiation conversion luminophore, which is thus induced to photoluminesce. The resulting light color of the LED results from the proportion of LED light transmitted and the emission spectrum of the radiation conversion luminophore. In one method, for this purpose, a polymeric material comprising a radiation conversion luminophore is applied directly to the LED light source (LED chip). Frequently, the polymeric material is applied to the LED chip, for instance, in droplet form or in hemispherical form, as a result of which particular optical effects contribute to the emission of the light. Setups of this kind, in which radiation conversion luminophore in a polymeric matrix is applied directly and without any intermediate space to an LED chip, are also referred to as "phosphor on a chip". In phosphor on a chip LEDs, the radiation conversion luminophores used are generally inorganic materials. In phosphor on a chip LEDs, the polymeric material and the radiation conversion luminophore are subject to relatively high thermal stress and radiation stress. For this reason, organic radiation conversion luminophores have not been suitable to date for use in phosphor on a chip LEDs.

In another method, the color converter (also referred to as "converter" or "light converter"), which generally comprises a polymer layer and one or more radiation conversion luminophore(s), is at a certain distance from the LED chip. A setup of this kind is referred to as "remote phosphor".

The spatial distance between the primary light source, the LED, and the color converter reduces the stress resulting from heat and radiation to such an extent that organic fluorescent dyes can also be used as radiation conversion luminophores. Furthermore, LEDs according to the "remote phosphor" concept are more energy-efficient than those according to the "phosphor on a chip" concept. The use of organic fluorescent dyes in these converters offers various advantages. Firstly, the hue of the light has good adjustability with fluorescent dyes. Secondly, there is no requirement for materials comprising rare earths, which have to be obtained by mining and provided in a costly and inconvenient manner and are available only to a limited extent.

White light-emitting LEDs are used in many application sectors as a lighting source or as a backlight in full-color displays. White light can be generated in various ways with LEDs. The basis for the emission of white light is always the superimposition (mixing) of various colors. In what are called multi-LEDs, for example, three light-emitting diodes which emit light in different colors, generally one blue, one green and one red, or two light-emitting diodes which emit light in complementary colors, one blue and one yellow, are combined in a housing. Because of the different brightnesses and operating conditions for the various light-emitting diodes, the multi-LED is technically complex and therefore expensive. Moreover, component miniaturization of the multi-LED is severely limited.

White light can also be generated by applying at least one radiation converter to an LED which preferably emits blue light having a wavelength of 400 to 500 nm. The radiation conversion luminophore used is frequently cerium-doped yttrium aluminum garnet (also referred to hereinafter as Ce:YAG). Ce is a luminophore which exhibits a broad emission band having a maximum at about 560 nm. According to the concentration of the radiation converter, portions of the blue light emitted by the LED are absorbed and converted to luminescence light which is yellow for the most part, such that the mixing of the blue light transmitted and the yellow light emitted gives rise to white light. The white hue or the color temperature of the LED therefore depends on the layer thickness and the exact composition of the Ce:YAG radiation converter. LEDs based on a blue-emitting LED and Ce:YAG are easy to produce. For simple applications in which color rendering and hue are of minor importance, the LED based on the blue-emitting Ce:YAG LED is of good suitability. Since the red component in the spectrum is absent, the blue portion dominates the light emitted. Therefore, an LED based on a blue-emitting LED and YAG as a sole radiation conversion luminophore is unsuitable for many applications. For applications in which high-quality color rendering is desired, the light radiation of the LED in the wavelength range from 460 to 580 nm is inadequate. A further disadvantage is the use of materials comprising rare earths, such as Ce:YAG, as explained hereinafter.

The color rendering index (CRI) is understood to mean a photometric parameter which gives an assessment of a light source in comparison to an ideal light source (Planckian radiator) with regard to quality in terms of the color rendering of up to 14 listed reference colors (CIE 1974). The size of the CRI value may be between 0 and 100 and describes the extent to which a light source is able to render the different colors of reference colors. The first commercially available white light LEDs had color rendering of 70 to 80. Sunlight has a CRI of up to 100.

WO 2012/168395 describes color converters which comprise at least one polymer and at least one organic fluorescent dye, wherein the organic fluorescent dye comprises at least one structural unit of the formula (A)

(A)

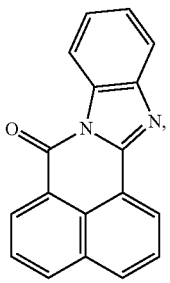

where the structural unit may be mono- or polysubstituted by identical or different substituents and where one or more CH groups in the six-membered ring of the benzimidazole structure shown may be replaced by nitrogen. Cyanated fluorescent dyes are not described in this document.

WO 2013/018041 describes color converters for LEDs, which comprise Ce:YAG with inorganic green and red radiation converters. Inorganic radiation converters comprise rare earths, which are obtained in a costly and inconvenient manner by mining and are therefore expensive. Furthermore, the color rendering index of the LEDs is not always satisfactory.

Some of the organic fluorescent dyes known from the prior art are unsatisfactory in terms of their photostability with respect to blue light in the wavelength range from 400 to 500 nm and/or the fluorescence quantum yield.

It is an object of the present invention to provide novel organic fluorescent dyes. The fluorescent dyes should have at least one of the following properties:
high photostability,
high fluorescence quantum yield,
high compatibility with the LED production operation,
use in place of Ce:YAG as a radiation conversion luminophore and
in combination with further red-emitting fluorescent dyes, improvement in the color rendering index of the light source.

The object is achieved by the provision of cyanated naphthalenebenzimidazole compounds of the formula I

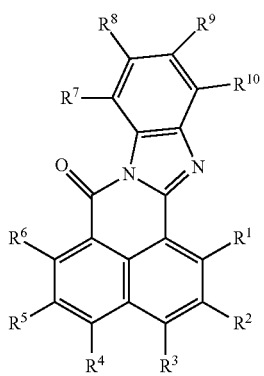

(I)

and mixtures thereof,
in which
$R^1$, $R^2$, $R^3$, $R^4$, $R^5$, $R^6$, $R^7$, $R^8$, $R^9$ and $R^{10}$ are each independently hydrogen, cyano (CN) or aryl which is unsubstituted or has one or more identical or different substituents $R^{Ar}$, where
each $R^{Ar}$ is independently selected from cyano, hydroxyl, mercapto, halogen, $C_1$-$C_{20}$-alkoxy, $C_1$-$C_{20}$-alkylthio, nitro, —$NR^{Ar2}R^{Ar3}$, —$NR^{Ar2}COR^{Ar3}$, —$CONR^{Ar2}R^{Ar3}$, —$SO_2NR^{Ar2}R^{Ar3}$, —$COOR^{Ar2}$, —$SO_3R^{Ar2}$,
$C_1$-$C_{30}$-alkyl, $C_2$-$C_{30}$-alkenyl, $C_2$-$C_{30}$-alkynyl, where the three latter radicals are unsubstituted or bear one or more $R^a$ groups,
$C_3$-$C_8$-cycloalkyl, 3- to 8-membered heterocyclyl, where the two latter radicals are unsubstituted or bear one or more $R^b$ groups,
aryl, U-aryl, heteroaryl and U-heteroaryl, where the four latter radicals are unsubstituted or bear one or more $R^b$ groups,
where
each $R^a$ is independently selected from cyano, hydroxyl, oxo, mercapto, halogen, $C_1$-$C_{20}$-alkoxy, $C_1$-$C_{20}$-alkylthio, nitro, —$NR^{Ar2}R^{Ar3}$, —$NR^{Ar2}COR^{Ar3}$, —$CONR^{Ar2}R^{Ar3}$, —$SO_2NR^{Ar2}R^{Ar3}$, —$COOR^{Ar2}$, —$SO_3R^{Ar2}$, $C_3$-$C_8$-cycloalkyl, 3- to 8-membered heterocyclyl, aryl and heteroaryl, where the cycloalkyl, heterocyclyl, aryl and heteroaryl radicals are unsubstituted or bear one or more $R^b$ groups;
each $R^b$ is independently selected from cyano, hydroxyl, oxo, mercapto, halogen, $C_1$-$C_{20}$-alkoxy, $C_1$-$C_{20}$-alkylthio, nitro, —$NR^{Ar2}R^{Ar3}$, —$NR^{Ar2}COR^{Ar3}$, —$CONR^{Ar2}R^{Ar3}$, —$SO_2NR^{Ar2}R^{Ar3}$, —$COOR^{Ar2}$, —$SO_3R^{Ar2}$, $C_1$-$C_{18}$-alkyl, $C_2$-$C_{18}$-alkenyl, $C_2$-$C_{18}$-alkynyl, $C_3$-$C_8$-cycloalkyl, 3- to 8-membered heterocyclyl, aryl and heteroaryl, where the four latter radicals are unsubstituted or bear one or more $R^b$ groups,
each $R^b$ is independently selected from cyano, hydroxyl, mercapto, oxo, nitro, halogen, —$NR^{Ar2}R^{Ar3}$, —$NR^{Ar2}COR^{Ar3}$, —$CONR^{Ar2}R^{Ar3}$, —$SO_2NR^{Ar2}R^{Ar3}$, —$COOR^{Ar2}$, —$SO_3R^{Ar2}$, —$SO_3R^{Ar2}$, $C_1$-$C_{18}$-alkyl, $C_2$-$C_{18}$-alkenyl, $C_2$-$C_{18}$-alkynyl, $C_1$-$C_{12}$-alkoxy, $C_1$-$C_{12}$-alkylthio,
U is an —O—, —S—, —$NR^{Ar1}$, —CO—, —SO— or —$SO_2$— moiety;
$R^{Ar1}$, $R^{Ar2}$, $R^{Ar3}$ are each independently hydrogen, $C_1$-$C_{18}$-alkyl, 3- to 8-membered cycloalkyl, 3- to 8-membered heterocyclyl, aryl or heteroaryl, where alkyl is unsubstituted or bears one or more $R^a$ groups, where 3- to 8-membered cycloalkyl, 3- to 8-membered heterocyclyl, aryl and heteroaryl are unsubstituted or bear one or more $R^b$ groups;
with the proviso that the compound of the formula I comprises at least one cyano group.

The inventive compounds of the formula I have at least one cyano (CN) group per compound. In general, the inventive compounds of the formula I comprise 1, 2, 3 or 4 cyano groups. The cyano group is bonded directly to the 1,8-naphthoylene-1,2-benzimidazole base skeleton of the formula A (A)

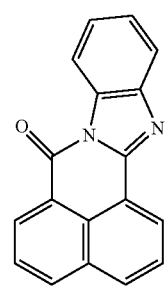

and/or to the base skeleton of the formula A via at least one of the substituents $R^1$, $R^2$, $R^3$, $R^4$, $R^5$, $R^6$, $R^7$, $R^8$, $R^9$ and $R^{10}$.

The inventive cyanated naphthalenebenzimidazole compounds of the formula I and mixtures thereof are surprisingly photostable, and therefore they are usable in a color converter for blue LEDs. In addition, the inventive cyanated naphthalenebenzimidazole compounds of the formula I and mixtures thereof have a high fluorescence quantum yield. They have high compatibility with the LED production process. The inventive cyanated naphthalenebenzimidazole compounds of the formula I and mixtures thereof are suitable, in combination with red-emitting fluorescent dyes, especially for color converters in blue-emitting LEDs, green-emitting or white emitting LEDs for production of light sources having a CRI above 90. Surprisingly, the novel fluorescent dyes are also suitable as alternative radiation conversion luminophores for Ce:YAG, and so white LEDs not comprising any rare earths as a luminophore are obtainable.

The present invention further provides a cyanated naphthalenebenzimidazole compound of the formula I or a mixtures of these obtainable by a process as described hereinafter.

The present invention further provides cyanated naphthalenebenzimidazole compounds of the formulae Ia and Ib

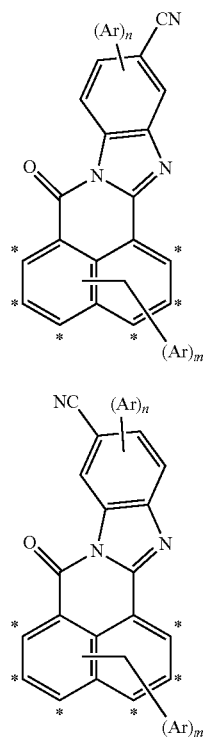

(Ia)

(Ib)

and mixtures thereof, in which Ar is aryl which is unsubstituted or mono- or polysubstituted by $R^{Ar}$, wherein $R^{Ar}$ is as defined above and n and m are each 1 or 2, and where $(Ar)_m$ are at one of the positions indicated with * obtainable by a process as described hereinafter.

The present invention further provides cyanated naphthalenebenzimidazole compounds of the formulae Ic and Id

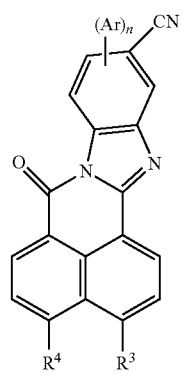

(Ic)

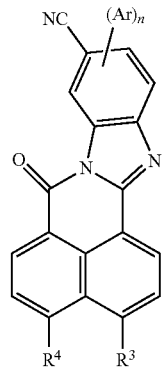

(Id)

and mixtures thereof, in which $R^3$, $R^4$ and Ar are aryl which is unsubstituted or mono- or polysubstituted by $R^{Ar}$, $R^{Ar}$ is as defined above and n is 1 or 2, obtainable by a process as described hereinafter.

The present invention further provides cyanated naphthalenebenzimidazole compounds of the formulae Ie and If

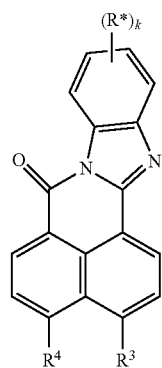

(Ie)

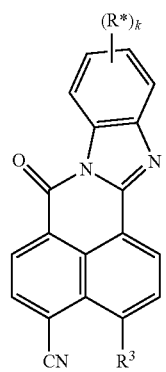

(If)

and mixtures thereof, in which
R³, if present, is aryl which is unsubstituted or mono- or polysubstituted by $R^{Ar}$;
R⁴, if present is aryl which is unsubstituted or mono- or polysubstituted by $R^{Ar}$;
each R* is independently cyano or aryl which is unsubstituted or has one or more identical or different substituents $R^{Ar}$, where $R^{Ar}$ is as defined in above; and
k is 0, 1 or 2
obtainable by a process as described hereinafter.

The present invention further provides cyanated naphthalenebenzimidazole compounds of the formula Ig

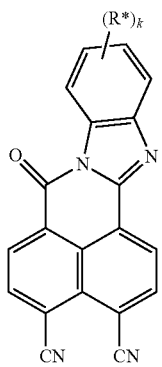

(Ig)

in which
each R* is independently cyano or aryl which is unsubstituted or has one or more identical or different substituents $R^{Ar}$, where $R^{Ar}$ is as defined above;
k is 0, 1 or 2;
obtainable by a process as described hereinafter.

The present invention further provides a cyanated naphthalenebenzimidazole compound of the formula I or a mixture of these of the formulae Ih, Ii, Ik or Im

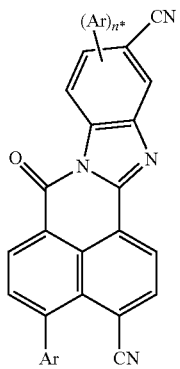

(Ih)

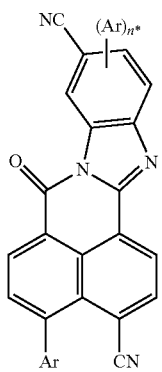

(Ii)

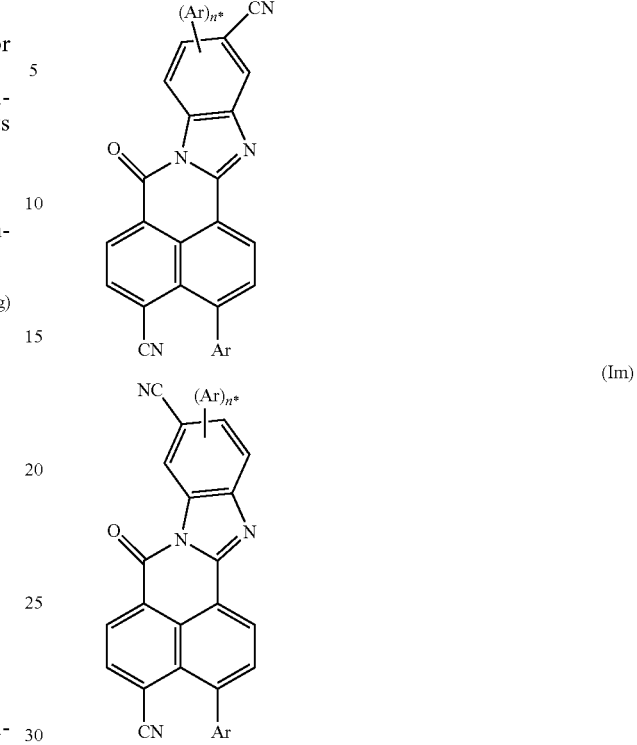

(Ik)

(Im)

in which Ar is aryl which is unsubstituted or mono- or polysubstituted by $R^{Ar}$, where $R^{Ar}$ is as defined above; and n* is 0, 1 or 2.

The present invention further provides color converters comprising at least one polymer and at least one cyanated naphthalenebenzimidazole compound of the formula I or mixtures thereof as defined above, and for the use thereof.

The present invention further provides lighting devices comprising at least one LED and at least one color converter, as defined above.

The present invention further provides a device producing electric power upon illumination comprising a photovoltaic cell and the color converter as defined herein, where at least a part of the light not absorbed by the photovoltaic cell is absorbed by the color converter.

BRIEF DESCRIPTION OF THE DRAWING

FIG. 1 shows the energy conversion efficiency versus the cortelated color temperature CCT of the inventive compound (11) versus example 10 from WO 2012/168395.

The definitions of the variables specified in the above formulae use collective terms which are generally representative of the respective substituents. The definition $C_n$-$C_m$ gives the number of carbon atoms possible in each case in the respective substituent or substituent moiety:

Halogen: fluorine, chlorine, bromine or iodine.
Alkyl and alkyl moieties in alkoxy and alkylthio: saturated straight-chain or branched hydrocarbyl radicals having 1 to 30 ($C_1$-$C_{30}$-alkyl), frequently 1 to 20 ($C_1$-$C_{20}$-alkyl) and especially 1 to 10 ($C_1$-$C_{10}$-alkyl) carbon atoms, such as methyl, ethyl, n-propyl, 1-methylethyl, n-butyl, 1-methylpropyl, 2-methylpropyl, 1,1-dimethylethyl, n-pentyl, 1-methylbutyl, 2-methylbutyl, 3-methylbutyl, 2,2-dimethylpropyl, 1-ethylpropyl, n-hexyl, 1,1-dimethylpropyl, 1,2-dimethylpropyl, 1-methyl pentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl and 1-ethyl-2-methylpropyl, n-heptyl, 1-methylhexyl, n-octyl, 1-methylheptyl, 2-ethylhexyl, n-nonyl, n-decyl.

Haloalkyl and all haloalkyl moieties in haloalkoxy: straight-chain or branched alkyl groups having 1 to 30, frequently 1 to 20 and especially 1 to 10 carbon atoms (as specified above), where some or all of the hydrogen atoms in these groups are replaced by halogen atoms as specified above.

Alkenyl: monounsaturated straight-chain or branched hydrocarbyl radicals having 2 to 30 ($C_2$-$C_{30}$-alkenyl), for example 2 to 20 or 3 to 10, carbon atoms and a double bond in any position, for example ethenyl, 1-propenyl, 2-propenyl, 1-methylethenyl, 1-butenyl, 2-butenyl, 3-butenyl, 1-methyl-1-propenyl, 2-methyl-1-propenyl, 1-methyl-2-propenyl, 2-methyl-2-propenyl.

Alkynyl: straight-chain or branched hydrocarbyl groups having 2 to 30 ($C_2$-$C_{30}$-alkynyl), for example 2 to 20 or 3 to 10, carbon atoms and a triple bond in any position, for example ethynyl, 1-propynyl, 2-propynyl, 1-butynyl, 2-butynyl, 3-butynyl, 1-methyl-2-propynyl.

Cycloalkyl: mono- or bicyclic saturated hydrocarbyl group having 3 to 8 carbon ring members, for example $C_3$-$C_8$-cycloalkyl such as cyclopropyl, cyclobutyl, cyclopentyl, cyclohexyl, cycloheptyl, cyclooctyl, bicyclo[2.2.1]hept-1-yl, bicyclo[2.2.1]hept-2-yl, bicyclo[2.2.1]hept-7-yl, bicyclo[2.2.2]oct-1-yl, bicyclo[2.2.2]oct-2-yl and bicyclo[3.3.0]octyl.

Aryl: mono-, di- or trinuclear (monocyclic, bicyclic or tricyclic) aromatic hydrocarbyl radicals having 6 to 14 and more preferably 6 to 10 carbon atoms, which do not comprise any ring heteroatoms. Examples of aryl are especially phenyl, naphthyl, indenyl, fluorenyl, anthracenyl, phenanthrenyl, and especially phenyl or naphthyl.

$C_5$-$C_8$-aryloxy: $C_5$-$C_8$-aryl as defined above, which is bonded to the skeleton via an oxygen atom (—O—). Preference is given to phenoxy and naphthyloxy.

3- to 8-membered heterocyclyl: mono- or bicyclic saturated or partially unsaturated ring system having 3, 4, 5, 6, 7 or 8 ring members, comprising, as well as carbon atoms as ring members, one, two, three or four heteroatoms or heteroatom-containing groups selected from O, N, S, SO and $S(O)_2$ as ring members.

Heteroaryl (hetaryl): mono-, di- or trinuclear (monocyclic, bicyclic or tricyclic) aromatic ring system having 5 to 14 ring members, some of which can be derived from the aforementioned aryl, in which at least one carbon atom in the aryl base skeleton is replaced by a heteroatom. Preferred heteroatoms are N, O and S. More preferably, the heteroaryl radicals have 5 to 13 ring atoms. More preferably, the heteroaryl radicals have, as well as carbon atoms, one, two, three or four heteroatoms selected from O, S and N as ring members. Especially preferably, the base skeleton of the heteroaryl radicals is selected from systems such as:

five- or six-membered aromatic heterocycle comprising one, two, three or four heteroatoms from the group of oxygen, nitrogen and sulfur: for example C-bonded 5-membered heteroaryl comprising one to three nitrogen atoms or one or two nitrogen atoms and/or one sulfur or oxygen atom as ring members, such as 2-furyl, 3-furyl, 2-thienyl, 3-thienyl, 2-pyrrolyl, 3-pyrrolyl, 3-isoxazolyl, 4-isoxazolyl, 5-isoxazolyl, 3-isothiazolyl, 4-isothiazolyl, 5-isothiazolyl, 3-pyrazolyl, 4-pyrazolyl, 5-pyrazolyl, 2-oxazolyl, 4-oxazolyl, 5-oxazolyl, 2-thiazolyl, 4-thiazolyl, 5-thiazolyl, 2-imidazolyl, 4-imidazolyl, 1,2,4-oxadiazol-3-yl, 1,2,4-oxadiazol-5-yl, 1,2,4-thiadiazol-3-yl, 1,2,4-thiadiazol-5-yl, 1,2,4-triazol-3-yl, 1,3,4-oxadiazol-2-yl, 1,3,4-thiadiazol-2-yl and 1,3,4-triazol-2-yl; nitrogen-bonded 5-membered heteroaryl comprising one to three nitrogen atoms as ring members, such as pyrrol-1-yl, pyrazol-1-yl, imidazol-1-yl, 1,2,3-triazol-1-yl and 1,2,4-triazol-1-yl; 6-membered heteroaryl comprising one to three nitrogen atoms as ring members, such as pyridin-2-yl, pyridin-3-yl, pyridin-4-yl, 3-pyridazinyl, 4-pyridazinyl, 2-pyrimidinyl, 4-pyrimidinyl, 5-pyrimidinyl, 2-pyrazinyl, 1,3,5-triazin-2-yl and 1,2,4-triazin-3-yl;

benzofused five- or six-membered aromatic heterocycle comprising one, two, three or four, preferably one, two or three heteroatoms from the group of oxygen, nitrogen and sulfur: for example five- or six-membered aromatic heterocycles, as defined above, which may comprise, as well as carbon atoms, one to four nitrogen atoms or one to three nitrogen atoms and one sulfur or oxygen atom as ring members, and in which two adjacent carbon ring members or one nitrogen and one adjacent carbon ring member may be bridged by a buta-1,3-diene-1,4-diyl group, such as indolyl, indazolyl, benzofuryl, dibenzofuryl, isobenzofuranyl, benzothiophenyl, dibenzothiophenyl, benzothiazolyl, benzoxazolyl, benzimidazolyl, carbazolyl, quinolinyl, isoquinolinyl, quinazolinyl, quinoxalinyl, cinnolinyl, phthalazinyl, purinyl, acridinyl, phenanthridinyl, phenazinyl and 1,7-phenanthrolinyl.

In the context of the present invention, a "blue LED" is understood to mean an LED which emits light in the wavelength range from 400 to 500 nm, preferably 420 to 480 nm and especially 440 to 460 nm. Suitable semiconductor materials are silicon carbide, zinc selenide and nitrides such as aluminum nitride (AlN), gallium nitride (GaN), indium nitride (InN) and indium gallium nitride (InGaN). In the context of the present invention, a "green LED" is understood to mean an LED which emits light in the wavelength range from 501 to 560 nm, preferably 501 to 540 nm and especially 520 to 540 nm. Suitable semiconductor materials are for example based on GaInNAs. In the context of the present invention, a "white LED" is understood to mean an LED which produces white light. Examples of a white LED are multi-LEDs or a blue LED in combination with at least one radiation conversion luminophore.

In the context of the present invention, "color converter" is understood to mean all physical devices capable of absorbing light of particular wavelengths and converting it to light of other wavelengths. Color converters are, for example, part of lighting devices, especially those lighting devices which utilize LEDs or OLEDs as a light source, or of fluorescence conversion solar cells.

The word "essentially" in the context of the present invention encompasses the words "completely", "wholly" and "all". The word encompasses a proportion of 90% or more, such as 95% or more, especially 99% or 100%.

The remarks which follow relating to preferred embodiments of the variables (substituents) of the compounds of the formulae I, I-A, Ia, Ib, Ic, Id, Ie, If, Ig, Ih, Ii, Ik or Im apply to any substituent independently and likewise in a combination of the substituents with one another.

The remarks which follow relating to preferred embodiments of the variables additionally apply to the compounds of the formulae I, I-A, Ia, Ib, Ic, Id, Ie, If, Ig, Ih, Ii, I k or Im and also to the use thereof in color converters and lighting devices.

The inventive compound of the formula I preferably comprises one, two or three cyano (CN) groups, especially 1 or 2 cyano groups.

With regard to the use of the inventive compound of the formula I as a fluorescent dye, the variables $R^1$, $R^2$, $R^3$, $R^4$, $R^5$, $R^6$, $R^7$, $R^8$, $R^9$ and $R^{10}$ are each independently, and preferably in combination, defined as follows, with the proviso that every compound of the formula I comprises at least one cyano group:

0, 1, 2, 3, 4, 5, 6 or 7 of the $R^1$, $R^2$, $R^3$, $R^4$, $R^5$, $R^6$, $R^7$, $R^8$, $R^9$ and $R^{10}$ radicals are identical or different aryl which is unsubstituted or has one or more identical or different substituents $R^{Ar}$. Among these, preference is given to those compounds of the formula I and mixtures thereof in which 1, 2, 3 or 4 of the $R^1$, $R^2$, $R^3$, $R^4$, $R^5$, $R^6$, $R^7$, $R^8$, $R^9$ and $R^{10}$ radicals are identical or different aryl which is unsubstituted or has 1, 2 or 3 identical or different substituents $R^{Ar}$. Preferably, each $R^{Ar}$ is independently selected from cyano, $C_1$-$C_{12}$-alkoxy, hydroxyl, halogen, nitro, —$NR^{Ar2}R^{Ar3}$, $NR^{Ar2}COR^{Ar3}$, —$CONR^{Ar2}R^{Ar3}$, —$SO_2NR^{Ar2}R^{Ar3}$, —$COOR^{Ar2}$, —$SO_3R^{Ar2}$, $C_1$-$C_{18}$-alkyl which is unsubstituted or mono- or polysubstituted, for example mono-, di-, tri- or tetrasubstituted, by hydroxyl, halogen, cyano, nitro or —$NR^{Ar2}R^{Ar3}$, and $C_3$-$C_8$-cycloalkyl and phenyl, where the two latter radicals are in turn unsubstituted or mono- or polysubstituted, for example mono-, di- or trisubstituted, by $C_1$-$C_{18}$-alkyl, $C_1$-$C_{12}$-alkoxy or cyano. In particular, $R^{Ar}$, if present, is selected from cyano and $C_1$-$C_{10}$-alkyl. In a very particularly preferred embodiment $R^{Ar}$ is cyano. Likewise, in a further particularly preferred embodiment $R^{Ar}$ is $C_1$-$C_{10}$-alkyl, such as methyl, ethyl, n-propyl, n-butyl, n-pentyl, n-hexyl.

Especially preferred are compounds of the formula I and mixtures thereof in which at least one of the $R^1$, $R^2$, $R^3$, $R^4$, $R^5$, $R^6$, $R^7$, $R^8$, $R^9$ and $R^{10}$ radicals is phenyl which is unsubstituted or has one or more identical or different $R^{Ar}$ radicals, where $R^{Ar}$ has one of the definitions given above, especially one of the preferred definitions. The other $R^1$, $R^2$, $R^3$, $R^4$, $R^5$, $R^6$, $R^7$, $R^8$, $R^9$ and $R^{10}$ radicals are each hydrogen or cyano. Even more preferred are compounds of the formula I and mixtures thereof in which at least one of the $R^1$, $R^2$, $R^3$, $R^4$, $R^5$, $R^6$, $R^7$, $R^8$, $R^9$ and $R^{10}$ radicals is phenyl which is unsubstituted or bears a cyano group. Likewise, even more preferred are compounds of the formula I and mixtures thereof in which at least one of the $R^1$, $R^2$, $R^3$, $R^4$, $R^5$, $R^6$, $R^7$, $R^8$, $R^9$ and $R^{10}$ radicals is phenyl, which is unsubstituted or carries 1, 2 or 3 substituents selected from $C_1$-$C_{10}$-alkyl. More particularly, 1, 2, 3 or 4, most preferably 1, 2 or 3, of the $R^1$, $R^2$, $R^3$, $R^4$, $R^5$, $R^6$, $R^7$, $R^8$, $R^9$ and $R^{10}$ radicals are phenyl which is unsubstituted or bears 1, 2 or 3 identical or different $R^{Ar}$ radicals, where $R^{Ar}$ has one of the above general or, in particular, one of the above preferred meanings. The other $R^1$, $R^2$, $R^3$, $R^4$, $R^5$, $R^6$, $R^7$, $R^8$, $R^9$ and $R^{10}$ radicals are each hydrogen or cyano. In a specific embodiment, one of the $R^1$, $R^2$, $R^3$, $R^4$, $R^5$, $R^6$ radicals is phenyl or 4-cyanophenyl and the other $R^1$, $R^2$, $R^3$, $R^4$, $R^5$, $R^6$ radicals are hydrogen or cyano and 0, 1 or 2 of the $R^6$, $R^7$, $R^8$, $R^9$ and $R^{10}$ radicals are phenyl or 4-cyanophenyl and the other $R^6$, $R^7$, $R^8$, $R^9$ and $R^{10}$ radicals are hydrogen or cyano. Likewise, in a further specific embodiment, one of the $R^1$, $R^2$, $R^3$, $R^4$, $R^5$, $R^6$ radicals is phenyl which is unsubstituted or carries 1, 2 or 3 substituents selected from $C_1$-$C_{10}$-alkyl and the other $R^1$, $R^2$, $R^3$, $R^4$, $R^5$, $R^6$ radicals are hydrogen or cyano and 1 or 2 of the $R^6$, $R^7$, $R^8$, $R^9$ and $R^{10}$ radicals are phenyl which is unsubstituted or carries 1, 2 or 3 substituents selected from $C_1$-$C_{10}$-alkyl and the other $R^6$, $R^7$, $R^8$, $R^9$ and $R^{10}$ radicals are hydrogen or cyano.

Zero, one, two or three of the $R^1$, $R^2$, $R^3$, $R^4$, $R^5$, $R^6$, $R^7$, $R^8$, $R^9$ and $R^{10}$ radicals are cyano. Among these, preference is given to those compounds of the formula I and mixtures thereof in which zero, one or two of the $R^1$, $R^2$, $R^3$, $R^4$, $R^5$, $R^6$, $R^7$, $R^8$, $R^9$ and $R^{10}$ radicals are cyano. More particularly, one or two of the $R^1$, $R^2$, $R^3$, $R^4$, $R^5$, $R^6$, $R^7$, $R^8$, $R^9$ and $R^{10}$ radicals are cyano.

In a first preferred embodiment, one or two of the $R^1$, $R^2$, $R^3$, $R^4$, $R^5$, $R^6$ radicals are phenyl, phenyl which carries 1, 2 or 3 substituents selected from $C_1$-$C_{10}$-alkyl or 4-cyanophenyl and the other $R^1$, $R^2$, $R^3$, $R^4$, $R^5$, $R^6$ radicals are hydrogen; and zero, one or two of the $R^7$, $R^8$, $R^9$ and $R^{10}$ radicals are phenyl, phenyl which carries 1, 2 or 3 substituents selected from $C_1$-$C_{10}$-alkyl, or 4-cyanophenyl and the other $R^7$, $R^8$, $R^9$ and $R^{10}$ radicals are hydrogen or cyano. Among these, preference is given to those compounds of the formula I and mixtures thereof where one or two of the $R^1$, $R^2$, $R^3$, $R^4$, $R^5$, $R^6$ radicals are phenyl or 4-cyanophenyl and the other $R^1$, $R^2$, $R^3$, $R^4$, $R^5$, $R^6$ radicals are hydrogen; and zero, one or two of the $R^7$, $R^8$, $R^9$ and $R^{10}$ radicals are phenyl or 4-cyanophenyl and the other $R^7$, $R^8$, $R^9$ and $R^{10}$ radicals are hydrogen or cyano. More preferably, one or two of the $R^1$, $R^2$, $R^3$, $R^4$, $R^5$, $R^6$ radicals are phenyl and the other $R^1$, $R^2$, $R^3$, $R^4$, $R^5$, $R^6$ radicals are hydrogen; and one or two of the $R^7$, $R^8$, $R^9$ and $R^{10}$ radicals are phenyl, one of the $R^7$, $R^8$, $R^9$ and $R^{10}$ radicals is cyano and the other $R^7$, $R^8$, $R^9$ and $R^{10}$ radicals is hydrogen.

In a second preferred embodiment, one or two of the $R^1$, $R^2$, $R^3$, $R^4$, $R^5$, $R^6$ radicals is/are cyano, phenyl, 4-cyanophenyl or phenyl which carries 1, 2 or 3 substituents selected from $C_1$-$C_{10}$-alkyl and the other $R^1$, $R^2$, $R^3$, $R^4$, $R^5$, $R^6$ radicals are hydrogen; and zero, one or two of the $R^7$, $R^8$, $R^9$ and $R^{10}$ radicals is/are phenyl, 4-cyanophenyl or phenyl which carries 1, 2 or 3 substituents selected from $C_1$-$C_{10}$-alkyl and the other $R^7$, $R^8$, $R^9$ and $R^{10}$ radicals are hydrogen or cyano. Especially, one or two of the $R^1$, $R^2$, $R^3$, $R^4$, $R^5$, $R^6$ radicals are phenyl, 4-cyanophenyl or cyano and the other $R^1$, $R^2$, $R^3$, $R^4$, $R^5$, $R^6$ radicals are hydrogen; and zero, one, two or three of the $R^7$, $R^8$, $R^9$ and $R^{10}$ radicals are phenyl or 4-cyanophenyl and the other $R^7$, $R^8$, $R^9$ and $R^{10}$ radicals are hydrogen or cyano. Among these, preference is given to those compounds of the formula I and mixtures thereof in which one of the $R^1$, $R^2$, $R^3$, $R^4$, $R^5$, $R^6$ radicals is phenyl, one of the $R^1$, $R^2$, $R^3$, $R^4$, $R^5$, $R^6$ radicals is cyano and the other $R^1$, $R^2$, $R^3$, $R^4$, $R^5$, $R^6$ radicals are hydrogen; and two of the $R^7$, $R^8$, $R^9$ and $R^{10}$ radicals are phenyl, and the other $R^7$, $R^8$, $R^9$ and $R^{10}$ radicals are hydrogen. Among these, preference is also given to those compounds of the formula I and mixtures thereof in which one of the $R^1$, $R^2$, $R^3$, $R^4$, $R^5$, $R^6$ radicals is phenyl, one of the $R^1$, $R^2$, $R^3$, $R^4$, $R^5$, $R^6$ radicals is cyano and the other $R^1$, $R^2$, $R^3$, $R^4$, $R^5$, $R^6$ radicals are hydrogen; and the $R^7$, $R^8$, $R^9$ and $R^{10}$ radicals are hydrogen. Among these, preference is also given to those compounds of the formula I and mixtures thereof in which two of the $R^1$, $R^2$, $R^3$, $R^4$, $R^5$, $R^6$ radicals are cyano, and the other $R^1$, $R^2$, $R^3$, $R^4$, $R^5$, $R^6$ radicals are hydrogen; and two of the $R^7$, $R^8$, $R^9$ and $R^{10}$ radicals are phenyl. Among these, preference is also given to those compounds of the formula I and mixtures thereof in which one of the $R^1$, $R^2$, $R^3$, $R^4$, $R^5$, $R^6$ radicals is phenyl, one of the $R^1$, $R^2$, $R^3$, $R^4$, $R^5$, $R^6$ radicals is cyano and the other $R^1$, $R^2$, $R^3$, $R^4$, $R^5$, $R^6$ radicals are hydrogen; and two of the $R^7$, $R^8$, $R^9$ and $R^{10}$ radicals are phenyl, and one of the $R^7$, $R^8$, $R^9$ and $R^{10}$ radicals is cyano and one of the $R^7$, $R^8$, $R^9$ and $R^{10}$ radicals is hydrogen. Among these, preference is also given to those compounds of the formula I and mixtures thereof in which one of the $R^1$, $R^2$, $R^3$, $R^4$, $R^5$, $R^6$ radicals is phenyl, two of the $R^1$, $R^2$, $R^3$, $R^4$, $R^5$, $R^6$ radicals are cyano and the other $R^1$, $R^2$, $R^3$, $R^4$, $R^5$, $R^6$ radicals are hydrogen; and two of the $R^7$, $R^8$, $R^9$ and $R^{10}$ radicals are phenyl, and the other $R^7$, $R^8$, $R^9$ and $R^{10}$ radicals are hydrogen. Among these, preference is also given to those compounds of the formula I and mixtures thereof in which one of the $R^1$, $R^2$, $R^3$, $R^4$, $R^5$, $R^6$ radicals is 4-cyanophenyl, one of the $R^1$, $R^2$, $R^3$, $R^4$, $R^5$, $R^6$ radicals is cyano and the other $R^1$, $R^2$, $R^3$, $R^4$, $R^5$, $R^6$ radicals are hydrogen; and two of the $R^7$, $R^8$, $R^9$ and $R^{10}$ radicals are phenyl, and the other $R^7$, $R^8$, $R^9$ and $R^{10}$ radicals are hydrogen. Likewise preferably, one of the $R^1$, $R^2$, $R^3$, $R^4$, $R^5$, $R^6$ radicals is phenyl which is unsubstituted or carries 1, 2 or 3 substituents selected from $C_1$-$C_{10}$-alkyl, one of the $R^1$, $R^2$, $R^3$, $R^4$, $R^5$, $R^6$ radicals is cyano and the other $R^1$, $R^2$, $R^3$, $R^4$, $R^5$, $R^6$ radicals are hydrogen; and two of the $R^7$, $R^8$, $R^9$ and $R^{10}$ radicals are phenyl, which is unsubstituted or carries 1, 2 or 3 substituents selected from $C_1$-$C_{10}$-alkyl and the other $R^7$, $R^8$, $R^9$ and $R^{10}$ radicals are hydrogen. Likewise preferably, one of the $R^1$, $R^2$, $R^3$, $R^4$, $R^5$, $R^6$ radicals is phenyl which carries 1 or 2 substituents, more preferably 1 substituent, selected from $C_1$-$C_{10}$-alkyl, one of the $R^1$, $R^2$, $R^3$, $R^4$, $R^5$, $R^6$ radicals is cyano and the other $R^1$, $R^2$, $R^3$, $R^4$, $R^5$, $R^6$ radicals are hydrogen; and two of the $R^7$, $R^8$, $R^9$ and $R^{10}$ radicals are phenyl, and the other $R^7$, $R^8$, $R^9$ and $R^{10}$ radicals are hydrogen. Likewise preferably, one of the $R^1$, $R^2$, $R^3$, $R^4$, $R^5$, $R^6$ radicals is phenyl which carries 1 or 2 substituents, more preferably 1 substituent, selected from $C_1$-$C_{10}$-alkyl, one of the $R^1$, $R^2$, $R^3$, $R^4$, $R^5$, $R^6$ radicals is cyano and the other $R^1$, $R^2$, $R^3$, $R^4$, $R^5$, $R^6$ radicals are hydrogen; and two of the $R^7$, $R^8$, $R^9$ and $R^{10}$ radicals are phenyl which carries 1, 2 or 3 substituents selected from $C_1$-$C_{10}$-alkyl, and the other $R^7$, $R^8$, $R^9$ and $R^{10}$ radicals are hydrogen. Likewise preferably, one of the $R^1$, $R^2$, $R^3$, $R^4$, $R^5$, $R^6$ radicals is phenyl, one of the $R^1$, $R^2$, $R^3$, $R^4$, $R^5$, $R^6$ radicals is cyano and the other $R^1$, $R^2$, $R^3$, $R^4$, $R^5$, $R^6$ radicals are hydrogen; and two of the $R^7$, $R^8$, $R^9$ and $R^{10}$ radicals are phenyl which carries 1, 2 or 3 substituents selected from $C_1$-$C_{10}$-alkyl, and the other $R^7$, $R^8$, $R^9$ and $R^{10}$ radicals are hydrogen.

Among these, a particularly preferred embodiment relates to compounds of the general formula I-A and mixtures thereof

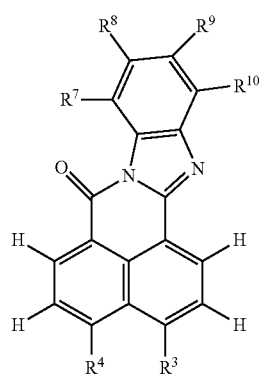

(I-A)

in which
$R^3$ and $R^4$ are each independently cyano, phenyl, 4-cyanophenyl or phenyl which carries 1, 2 or 3 substituents selected from $C_1$-$C_{10}$-alkyl, especially cyano, phenyl or 4-cyanophenyl; and
$R^7$, $R^8$, $R^9$ and $R^{10}$ are each independently hydrogen, cyano, phenyl, 4-cyanophenyl or phenyl which carries 1, 2 or 3 substituents selected from $C_1$-$C_{10}$-alkyl, especially hydrogen, cyano, phenyl or 4-cyanophenyl.

Compounds in turn preferred among the compounds of the formula I-A are those which correspond to the formula I-Aa

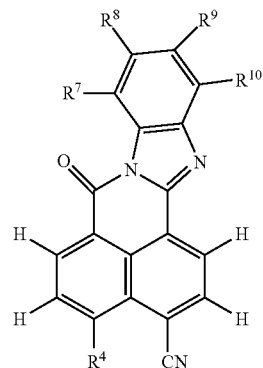

(I-Aa)

in which
$R^4$ is phenyl, 4-cyanophenyl or phenyl which carries 1, 2 or 3 substituents selected from $C_1$-$C_{10}$-alkyl; and
two of the radicals $R^7$, $R^8$, $R^9$ and $R^{10}$ are each independently, phenyl, 4-cyanophenyl or phenyl which carries 1, 2 or 3 substituents selected from $C_1$-$C_{10}$-alkyl and the other radicals $R^7$, $R^8$, $R^9$ and $R^{10}$ are hydrogen.

Compounds in turn preferred among the compounds of the formula I-A are also those which correspond to the formulae I-Ab and I-Ab'

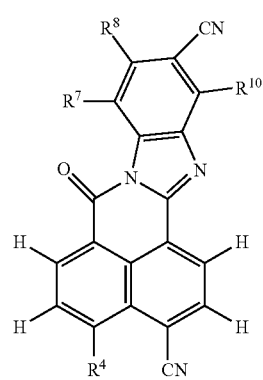

(I-Ab)

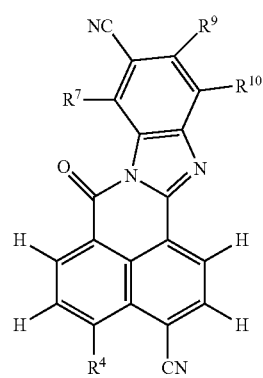

(I-Ab')

in which
$R^4$ is phenyl, 4-cyanophenyl or phenyl which carries 1, 2 or 3 substituents selected from $C_1$-$C_{10}$-alkyl; and zero, one or two of the radicals $R^7$, $R^{10}$, if present, $R^8$ and $R^9$ are each independently, phenyl, 4-cyanophenyl or phenyl which carries 1, 2 or 3 substituents selected from $C_1$-$C_{10}$-alkyl and the other radicals $R^7$, $R^{10}$, $R^8$, $R^9$, if present, are hydrogen.

Compounds in turn preferred among the compounds of the formula I-A are also those which correspond to the formula I-Ac

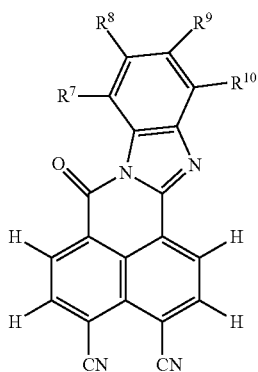

(I-Ac)

in which
one or two of the radicals $R^7$, $R^8$, $R^9$ and $R^{10}$ are each independently, phenyl, 4-cyanophenyl or phenyl which carries 1, 2 or 3 substituents selected from $C_1$-$C_{10}$-alkyl and the other radicals $R^7$, $R^8$, $R^9$ and $R^{10}$ are hydrogen.

Compounds in turn preferred among the compounds of the formula I-A are also those which correspond to the formula I-Ad and I-Ad'

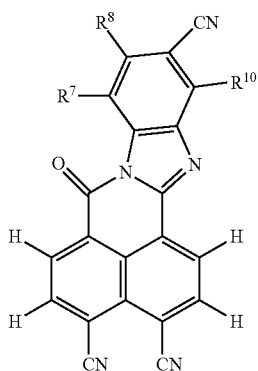

(I-Ad)

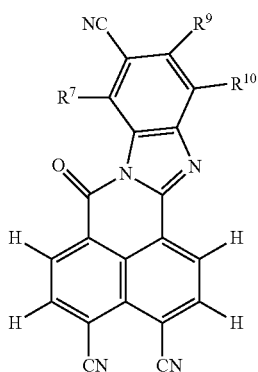

(I-Ad')

in which
one or two of the radicals $R^7$, $R^8$, $R^9$ and $R^{10}$ are each independently, phenyl, 4-cyanophenyl or phenyl which carries 1, 2 or 3 substituents selected from $C_1$-$C_{10}$-alkyl and the other radicals $R^7$, $R^8$, $R^9$ and $R^{10}$ are hydrogen.

Particular preference is given to compounds of the formula I-A in which
$R^3$ is cyano,
$R^4$, $R^8$ and $R^{10}$ are phenyl, and
$R^7$ and $R^9$ are hydrogen;
or
$R^3$ is cyano,
$R^4$, $R^7$ and $R^9$ are phenyl and
$R^8$ and $R^{10}$ are hydrogen
and mixtures thereof.

Particular preference is also given to compounds of the formula I-A in which
$R^4$ is cyano,
$R^3$, $R^8$ and $R^{10}$ are phenyl, and
$R^7$ and $R^9$ are hydrogen;
or
$R^4$ is cyano,
$R^3$, $R^7$ and $R^9$ are phenyl, and
$R^8$ and $R^{10}$ are hydrogen;
and mixtures thereof.

Particular preference is also given to compounds of the formula I-A in which
$R^3$ and $R^4$ are cyano,
$R^8$ and $R^{10}$ are phenyl, and
$R^7$ and $R^9$ are hydrogen;
or
$R^3$ and $R^4$ are cyano,
$R^4$, $R^7$ and $R^9$ are phenyl, and
$R^8$ and $R^{10}$ are hydrogen;
and mixtures thereof.

Particular preference is also given to compounds of the formula I-A in which
$R^3$ is cyano,
$R^4$ is phenyl, and
$R^7$, $R^8$, $R^9$ and $R^{10}$ are hydrogen
or
$R^3$ is phenyl
$R^4$ is cyano, and
$R^7$, $R^8$, $R^9$ and $R^{10}$ are hydrogen
and mixtures thereof.

Particular preference is also given to compounds of the formula I-Aa in which
$R^4$ is phenyl which is unsubstituted or carries 1 substituents selected from $C_1$-$C_{10}$-alkyl, and
$R^8$ and $R^{10}$ are independently of each other phenyl which is unsubstituted or carries 1 or 2 substituents selected from $C_1$-$C_{10}$-alkyl; and
$R^7$ and $R^9$ are hydrogen;

Particular preference is also given to compounds of the formula I-Aa in which
$R^4$ is phenyl which is unsubstituted or carries 1 substituents selected from $C_1$-$C_{10}$-alkyl, and
$R^7$ and $R^9$ are independently of each other phenyl which is unsubstituted or carries 1 or 2 substituents selected from $C_1$-$C_{10}$-alkyl; and $R^8$ and $R^{10}$ are hydrogen.

Particular preference is also given to compounds of the formula I-Aa in which
$R^4$ is phenyl which is unsubstituted or carries 1 substituents selected from $C_1$-$C_{10}$-alkyl, and
$R^8$ and $R^9$ are independently of each other phenyl which is unsubstituted or carries 1 or 2 substituents selected from $C_1$-$C_{10}$-alkyl; and $R^7$ and $R^{10}$ are hydrogen.

Particular preference is also given to compounds of the formula I-Aa in which
$R^4$ is phenyl which is unsubstituted or carries 1 substituents selected from $C_1$-$C_{10}$-alkyl, and
$R^7$ and $R^{10}$ are independently of each other phenyl which is unsubstituted or carries 1 or 2 substituents selected from $C_1$-$C_{10}$-alkyl; and
$R^8$ and $R^9$ are hydrogen.

Particular preference is also given to compounds of the formula I-Ab in which
$R^4$ is phenyl which is unsubstituted or carries 1 substituents selected from $C_1$-$C_{10}$-alkyl, and
one of the radicals $R^7$, $R^8$ and $R^{10}$ is phenyl which is unsubstituted or carries 1 or 2 substituents selected from $C_1$-$C_{10}$-alkyl; and the other radicals $R^7$, $R^8$ and $R^{10}$ are hydrogen.

Particular preference is also given to compounds of the formula I-Ab in which
$R^4$ is phenyl which is unsubstituted or carries 1 substituents selected from $C_1$-$C_{10}$-alkyl, and
two of the radicals $R^7$, $R^8$ and $R^{10}$ are phenyl which is unsubstituted or carries 1 or 2 substituents selected from $C_1$-$C_{10}$-alkyl; and the other radicals $R^7$, $R^8$ and $R^{10}$ are hydrogen.

Particular preference is also given to compounds of the formula I-Ab' in which
$R^4$ is phenyl which is unsubstituted or carries 1 substituents selected from $C_1$-$C_{10}$-alkyl, and
one of the radicals $R^7$, $R^9$ and $R^{10}$ is phenyl which is unsubstituted or carries 1 or 2 substituents selected from $C_1$-$C_{10}$-alkyl; and the other radicals $R^7$, $R^9$ and $R^{10}$ are hydrogen.

Particular preference is also given to compounds of the formula I-Ab' in which
$R^4$ is phenyl which is unsubstituted or carries 1 substituents selected from $C_1$-$C_{10}$-alkyl, and
two of the radicals $R^7$, $R^9$ and $R^{10}$ are phenyl which is unsubstituted or carries 1 or 2 substituents selected from $C_1$-$C_{10}$-alkyl; and the other radicals $R^7$, $R^9$ and $R^{10}$ are hydrogen.

The compounds of the formula I and mixtures thereof can be prepared by processes known to those skilled in the art or as described in the experimental section which follows. One process comprises the condensation of 1,8-naphthalic anhydride with a 1,2-diamino-substituted aromatic which optionally already bears the desired substituents of the end product, the bromination of the condensation product and the subsequent substitution of the bromine atoms for optionally substituted aryl and/or cyano.

A further process comprises the condensation of 4,5-dihalo-1,8-naphthalic anhydride with a 1,2-diamino-substituted aromatic which optionally already bears the desired substituents of the end product, and subsequent substitution of the halogen atoms for optionally substituted aryl and/or cyano.

A further process comprises the condensation of 4,5-dihalo-1,8-naphthalic anhydride with a 1,2-diamino-substituted aromatic which optionally already bears the desired substituents of the end product, the bromination of the condensation product and subsequent substitution of the halogen atoms and bromine atoms for optionally substituted aryl and/or cyano.

A further process comprises the condensation of 4,5-dichloro-1,8-naphthalic anhydride with a 1,2-diamino-substituted aromatic which optionally already bears the desired substituents of the end product, the bromination of the condensation product and subsequent substitution of one chlorine atom and a part of the bromine atoms for substituted aryl, followed by substitution of the remaining chlorine atom by cyano.

For preparation of pure compounds of the formula I or of product mixtures enriched in one or more compounds of the formula I, it may be advantageous to undertake a partial or full separation of the isomers formed at one or more reaction stages, and to use the fully or partly separated isomers as the reactant in the next reaction stage.

The present invention provides a cyanated naphthalenebenzimidazole compound of the formula I

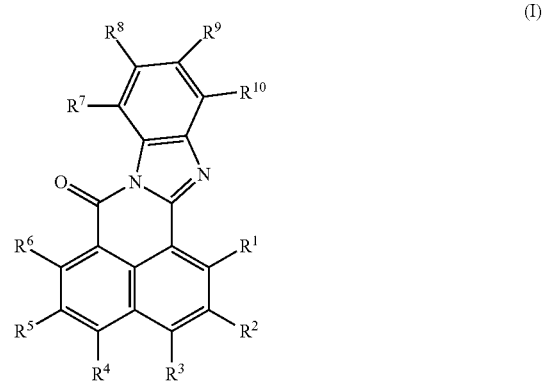

(I)

or a mixture of these,
where $R^1$, $R^2$, $R^3$, $R^4$, $R^5$, $R^6$, $R^7$, $R^8$, $R^9$ and $R^{10}$ are as defined as above
obtainable by a process in which
1.1) 1,8-naphthalic anhydride is reacted with a diamine of the formula (i)

(i)

where
each R* is independently cyano or aryl which is unsubstituted or has one or more identical or different substituents $R^{Ar}$, where $R^{Ar}$ is as defined above
k is 0, 1 or 2,
to obtain a compound of the formula (ii)

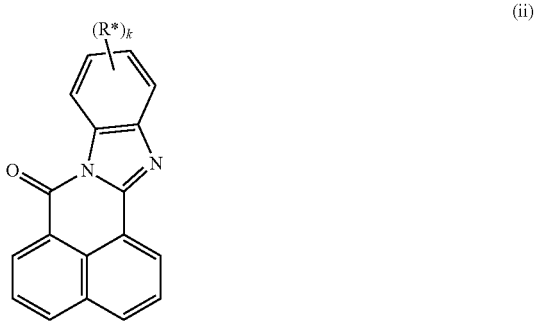

(ii)

1.2) the compound of the formula (ii) obtained in step 1.1) is subjected to a bromination to obtain a compound of the formula (iii)

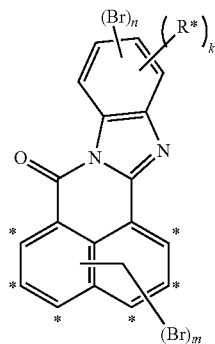

(iii)

in which n is 1 or 2;

m is 1 or 2, where (Br), radicals are at one or more of the positions indicated by *;

1.3) the compound of the formula (iii) obtained in step 1.2) is subjected to a substitution of bromine to aryl which is unsubstituted or has one or more identical or different substituents $R^{Ar}$, where $R^{Ar}$ is as defined above by cross-coupling with an organometallic compound of the formula iv Ar-Met (iv)

in which

Ar is aryl which is mono- or polysubstituted by $R^{Ar}$; and

Met is $B(OH)_2$, $B(OR')(OR'')$, Zn—R''' or $Sn(R^*)_3$, in which

R' and R'' are each independently hydrogen, $C_1$-$C_{30}$-alkyl, $C_5$-$C_8$-cycloalkyl, $C_6$-$C_{14}$-aryl or heteroaryl, or R' and R'' together are $C_2$-$C_4$-alkylene which optionally bears 1, 2, 3, 4, 5, 6, 7 or 8 substituents selected from $C_1$-$C_4$-alkyl, $C_5$-$C_8$-cycloalkyl, $C_6$-$C_{14}$-aryl and heteroaryl, R''' is $C_1$-$C_8$-alkyl or phenyl and R* is $C_1$-$C_8$-alkyl or phenyl, in the presence of a transition metal catalyst to obtain the compound of the formula I

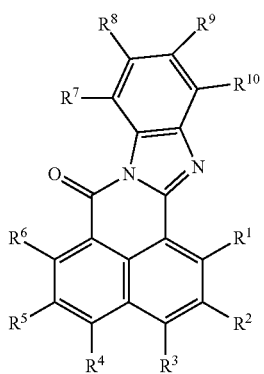

(I)

where 1 or 2 of the radicals $R^1$, $R^2$, $R^3$, $R^4$, $R^5$ or $R^6$ are aryl, which is unsubstituted or has one or more identical or different substituents $R^{Ar}$, and the other radicals $R^1$, $R^2$, $R^3$, $R^4$, $R^5$ or $R^6$ are hydrogen and one or two of the radicals $R^7$, $R^8$, $R^9$ or $R^{10}$ are aryl, which is unsubstituted or has one or more identical or different substituents $R^{Ar}$, and the other radicals $R^7$, $R^8$, $R^9$ or $R^{10}$ are hydrogen, cyano or aryl which is unsubstituted or has one or more identical or different substituents $R^{Ar}$ 1.4) the compound(s) obtained in step 1.3) are optionally subjected to at least one separation and/or purification step;

or 2.1) 1,8-dihalonaphthalic anhydride of the formula (v)

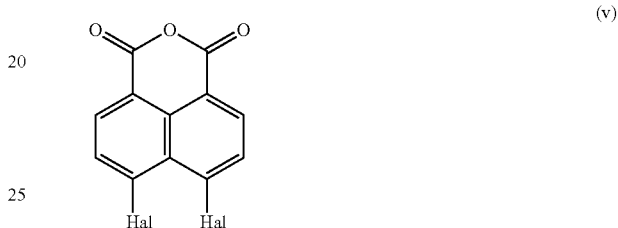

(v)

where Hal is chlorine or bromine is reacted with a diamine of the formula (i)

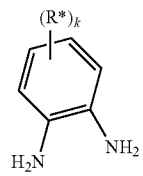

(i)

where each R* is independently cyano or aryl which is unsubstituted or has one or more identical or different substituents $R^{Ar}$, where $R^{Ar}$ is as defined above;

k is 0, 1 or 2;

to obtain a compound of the formula (vi)

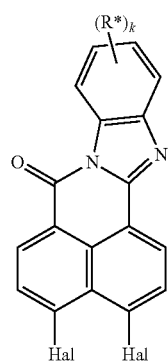

(vi)

2.2) the compound of the formula (vi) obtained in step 2.1) is subjected to a bromination to obtain a compound of the formula (vii)

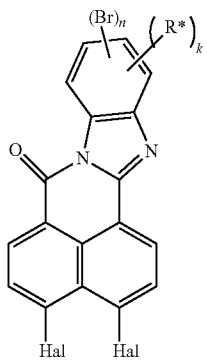

in which
n is 1 or 2;

2.3) the compound of the formula (vii) obtained in step 2.2) is subjected to a substitution reaction, wherein each Hal and each bromine atom is substituted by aryl which is unsubstituted or has one or more identical or different substituents $R^{Ar}$, where $R^{Ar}$ is as defined above, or the compounds of the formula (vii) obtained in step 2.2) is subjected to a substitution reaction, wherein each Hal is substituted by aryl, and a part of the bromine atoms attached to the benzene ring of the benzimidazole moiety are substituted by aryl and the other bromine atoms that are not substituted by aryl, are substituted by hydrogen, where aryl is unsubstituted or has one or more identical or different substituents $R^{Ar}$, where $R^{Ar}$ is as defined above by cross-coupling with an organometallic compound of the formula iv Ar-Met (iv)

in which Ar and Met are as defined above
in the presence of a transition metal catalyst to obtain the compound of the formula I

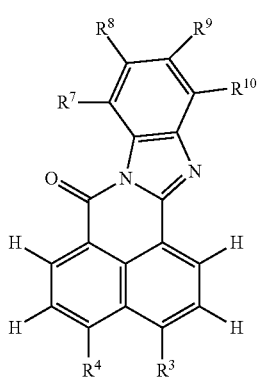

where
$R^3$ and $R^4$ are aryl, which is unsubstituted or has one or more identical or different substituents $R^{Ar}$,
zero, one or two of the radicals $R^7$, $R^8$, $R^9$ or $R^{10}$ are aryl, which is unsubstituted or has one or more identical or different substituents $R^{Ar}$, and the other radicals $R^7$, $R^8$, $R^9$ or $R^{10}$ are hydrogen, cyano or aryl which is unsubstituted or has one or more identical or different substituents $R^{Ar}$, 2.4) the compound(s) obtained in step 2.3) are optionally subjected to at least one separation and/or purification step;

or 3.1a) the compound of the formula (vii) obtained in step 2.2), wherein each Hal is chlorine, is subjected to a substitution reaction, where one of the Hal is substituted by aryl, and all or a part of the bromine atoms attached to the benzene ring of the benzimidazole moiety are substituted by aryl and the other bromine atoms that are not substituted by aryl, are substituted by hydrogen, where aryl is unsubstituted or has one or more identical or different substituents $R^{Ar}$, where $R^{Ar}$ is as defined in claim 1 by cross-coupling with an organometallic compound of the formula IV

Ar-Met (IV)

in which Ar and Met are as defined above in the presence of a transition metal catalyst to obtain the compound of the formula (viiia) and (viiib)

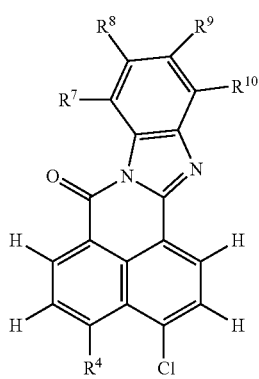

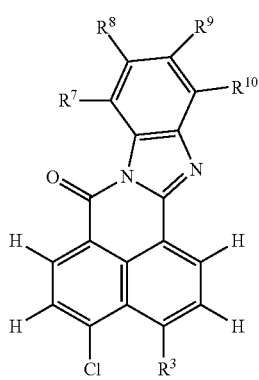

where
$R^3$, if present, is aryl, which is unsubstituted or has one or more identical or different substituents $R^{Ar}$;
$R^4$, if present, is aryl, which is unsubstituted or has one or more identical or different substituents $R^{Ar}$;
zero, one or two of the radicals $R^7$, $R^8$, $R^9$ or $R^{10}$ are aryl, which is unsubstituted or has one or more identical or different substituents $R^{Ar}$, and the other radicals $R^7$, $R^8$, $R^9$ or $R^{10}$ are hydrogen, cyano or aryl which is unsubstituted or has one or more identical or different substituents $R^{Ar}$ 3.2a) if appropriate, the compounds of formulae (viiia) and (viiib) are subjected to at least one purification and/or separation step;

3.3a) the compound(s) obtained in step 3.1) or 3.2) is reacted with a metal cyanide to obtain compound(s) of the formula I,

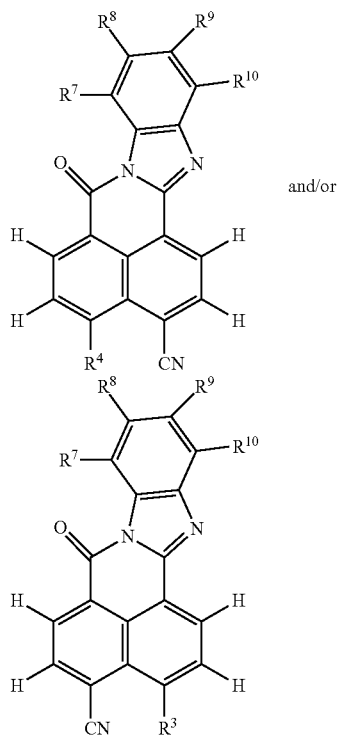

and/or where
R$^3$, if present, is aryl which is unsubstituted or mono- or polysubstituted by R$^{Ar}$;
R$^4$, if present, is aryl which is unsubstituted or mono- or polysubstituted by R$^{Ar}$;
zero, one or two of the radicals R$^7$, R$^8$, R$^9$ or R$^{10}$ are aryl, which is unsubstituted or has one or more identical or different substituents R$^{Ar}$, and the other radicals R$^7$, R$^8$, R$^9$ or R$^{10}$ are hydrogen, cyano or aryl which is unsubstituted or has one or more identical or different substituents R$^{Ar}$ 3.4a) the compound(s) obtained in step 3.3a) is optionally subjected to at least one separation and/or purification step;
or
3.1b1) the compounds of the formula (vi) obtained in step 2.1) is reacted with a metal cyanide to obtain compounds of the formulae (ixa) and (ixb)

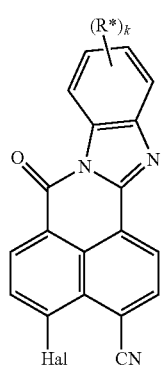

(ixa)

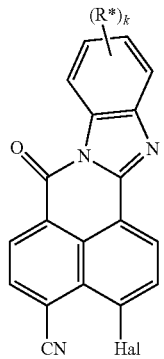

(ixb)

where (R*)$_k$ and Hal are as defined above;
3.1b2) the compounds of the formula (ixa) and (ixb) obtained in step 3.1b1) are subjected to a cross-coupling with an organometallic compound of the formula iv Ar-Met    (iv)

where Ar and Met are as defined above,
in the presence of a transition metal catalyst to give compounds of the formula I

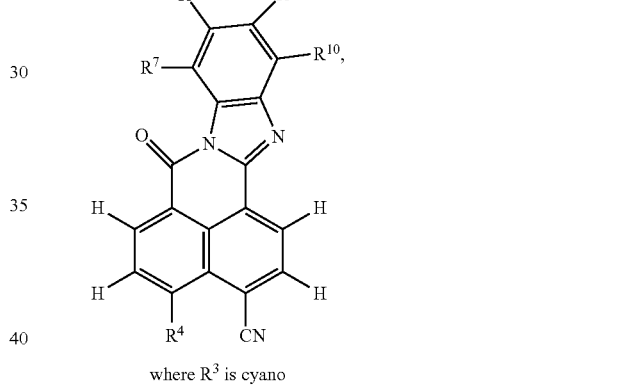

(I)

where R$^3$ is cyano

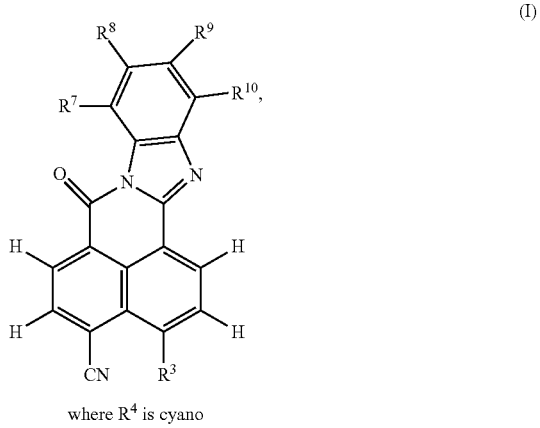

(I)

where R$^4$ is cyano where
R$^3$, if present, is aryl which is unsubstituted or mono- or polysubstituted by R$^{Ar}$,
R$^4$, if present, is aryl which is unsubstituted or mono- or polysubstituted by R$^{Ar}$,
zero, one or two of the radicals R$^7$, R$^8$, R$^9$ or R$^{10}$ are cyano or aryl which is unsubstituted or has one or more identical or different substituents R$^{Ar}$ and the remaining radicals R$^7$, R$^8$, R$^9$ or R$^{10}$ are hydrogen;

3.1b3) the compound(s) of formula I are optionally subjected to at least one separation and/or purification step;
or
3.2b1) the compound of the formula (vi) obtained in step 2.1) is first reacted with a compound of the formula (IV)

Ar-Met (iv)

where Ar and Met are as defined above,
in the presence of a transition metal catalyst to give a compound of the formula (xa) and (xb)

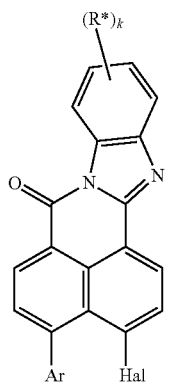
(xa)

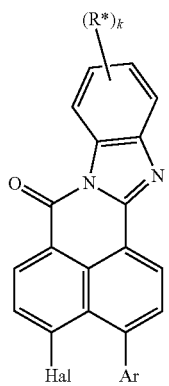
(xb)

with a metal cyanide to obtain compounds of the formulae and then treated with a metal cyanide
3.2b2) the compounds of the formulae (xa) and (xb) obtained in step 3.2b1) is reacted with a metal cyanide to obtain compounds of the formulae;

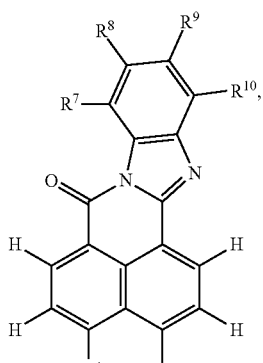
(I)

where $R^3$ is cyano

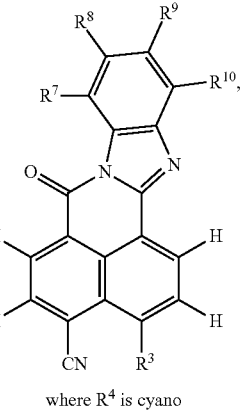
(I)

where $R^4$ is cyano where
$R^3$, if present, is aryl which is unsubstituted or mono- or polysubstituted by $R^{Ar}$;
$R^4$, if present, is aryl which is unsubstituted or mono- or polysubstituted by $R^{Ar}$;
zero, one or two of the radicals $R^7$, $R^8$, $R^9$ or $R^{10}$ are cyano or aryl which is unsubstituted or has one or more identical or different substituents $R^{Ar}$ and the remaining radicals $R^7$, $R^8$, $R^9$ or $R^{10}$ are hydrogen;
3.2b3) the compound(s) obtained in step 3.2b2) is optionally subjected to at least one separation and/or purification step;
or
4.1) the compounds of the formula (vi) obtained in step 2.1) is reacted with a metal cyanide to obtain a compound of the formula (I)

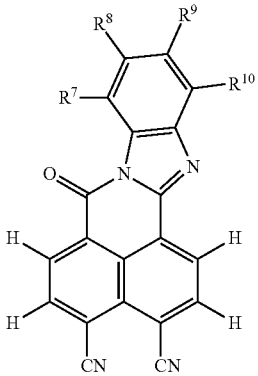

where
zero, one or two of the radicals $R^7$, $R^8$, $R^9$ or $R^{10}$ are cyano or aryl which is unsubstituted or has one or more identical or different substituents $R^{Ar}$ and the remaining radicals $R^7$, $R^8$, $R^9$ or $R^{10}$ are hydrogen;
4.2) the compound(s) of formula I is optionally subjected to at least one separation and/or purification step.
In terms of the process, the procedure of steps 1.1), 1.2), 1.3) and 1.4) is as described in steps a1), a2), a3) and a4) described below.
In terms of the process, the procedure of steps 2.1), 2.2), 2.3) and 2.4) is as described in steps b1), b2), b3) and b4) described below.
In terms of the process, the procedure of steps 3.1a), 3.2a), 3.3a) and 3.4a) is as described in steps c2), c3), c4) and c5) described below.
In terms of the process, the procedure of steps 3.1b1), 3.1b2), 3.1b3), and 3.2b1), 3.2b2), 3.2b3), is as described in steps c2a), c3a) and c5) described below.

In terms of the process, the procedure of steps 4.1), 4.2), is as described in steps d1) and d2) described below.

It is obvious that the above reaction sequences can be changed and that the compounds obtained in any step may be subjected to at least one separation step and/or purification step.

The present invention further provides a cyanated naphthalenebenzimidazole compound of the formula I or a mixture of these, which corresponds to compounds of the formulae Ia and Ib

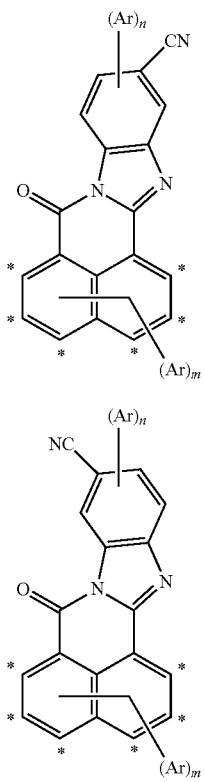

(Ia)

(Ib)

and mixtures thereof,
in which
Ar is aryl which is optionally mono- or polysubstituted by $R^{Ar}$, where $R^{Ar}$ is as defined above;
n is 1 or 2, and
m is 1 or 2, and where $(Ar)_m$ are at one of the positions indicated with *;
obtainable by a process in which
a1) 1,8-naphthalic anhydride is reacted with 3,4-diaminobenzonitrile to obtain compounds of the formulae IIa and IIb;

(IIa)

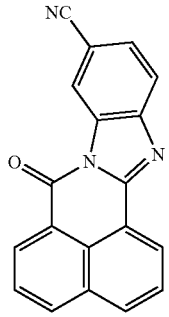

(IIb)

a2) the compounds of the formulae IIa and IIb obtained in step a1) are subjected to a bromination to obtain compounds of the formulae IIIa and IIIb

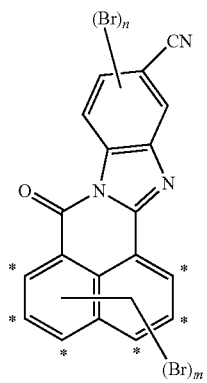

(IIIa)

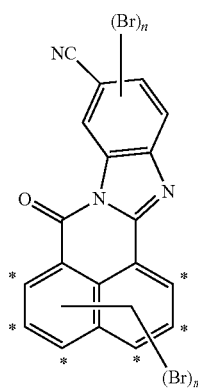

(IIIb)

in which
n is 1 or 2,
m is 1 or 2, and where $(Br)_m$ are at one of the positions indicated with *;
a3) the compounds of the formulae IIIa and IIIb obtained in step a2) are subjected to a cross-coupling with an organometallic compound of the formula IV Ar-Met  (IV)

in which
Ar is aryl which is mono- or polysubstituted by $R^{Ar}$; and
Met is $B(OH)_2$, $B(OR')(OR'')$, Zn—R''' or $Sn(R^*)_3$,
in which
R' and R'' are each independently hydrogen, $C_1$-$C_{30}$-alkyl, $C_5$-$C_8$-cycloalkyl, $C_6$-$C_{14}$-aryl or heteroaryl, or R' and R'' together are $C_2$-$C_4$-alkylene which optionally bears 1, 2, 3, 4, 5, 6, 7 or 8 substituents selected from $C_1$-$C_4$-alkyl, $C_5$-$C_8$-cycloalkyl, $C_5$-$C_8$-aryl and heteroaryl, R''' is $C_1$-$C_8$-alkyl or phenyl and
R* is $C_1$-$C_8$-alkyl or phenyl,
in the presence of a transition metal catalyst to obtain the compounds of the formulae Ia and Ib,
and
a4) the compounds of the formulae Ia and Ib obtained in step a3) are optionally subjected to at least one separation and/or purification step.

Step a1)

The imidation of the carboxylic anhydride groups in reaction step a1) is known in principle. Preference is given to reacting 1,8-naphthalic anhydride with 3,4-diaminobenzonitrile in the presence of a polar aprotic solvent. Suitable polar aprotic solvents are nitrogen heterocycles such as pyridine, pyrimidine, quinoline, isoquinoline, quinaldine, N-methylpiperidine, N-methylpiperidone and N-methylpyrrolidone.

The reaction is advantageously effected in the presence of an imidation catalyst. Suitable imidation catalysts are organic and inorganic acids, for example formic acid, acetic acid, propionic acid and phosphoric acid. Suitable imidation catalysts are additionally organic and inorganic salts of transition metals, such as zinc, iron, copper and magnesium. Examples of these include zinc acetate, zinc propionate, zinc oxide, iron(II) acetate, iron(III) chloride, iron(II) sulfate, copper(II) acetate, copper(II) oxide and magnesium acetate. The molar ratio of anhydride to imidation catalyst is generally 1.2:1 to 1:1.2, preferably 1:1.

The reaction temperature is generally ambient temperature to 200° C., preferably 120° C. to 160° C.

1,8-Naphthalic anhydride and 3,4-diaminobenzonitrile are commercially available.

The imides of the formulae IIa and IIb obtained in reaction step a1) are generally used for the subsequent reaction without further purification.

Step a2)

The compounds of the formulae IIa and IIb are typically brominated with elemental bromine in a solvent. Further suitable brominating agents are N-bromosuccinimide and dibromoisocyanuric acid. Suitable solvents are water or aliphatic monocarboxylic acids, and chlorinated hydrocarbons such as chlorobenzene and chloroform. Suitable aliphatic monocarboxylic acids are those having 2 to 6 carbon atoms, such as acetic acid, propionic acid, butyric acid, pentanecarboxylic acid and hexanecarboxylic acid, and mixtures thereof. When an aliphatic monocarboxylic acid is used as a solvent, it may be advantageous to use iodine as a catalyst.

Typically, bromine is used in a large excess, based on the compounds of the formulae IIa and IIb. The molar amount of bromine depends on the desired halogenation level of the compounds of the formulae IIIa and IIIb. If a di-, tri- and tetrabromination of the compounds of the formulae IIa and IIb is intended, the molar ratio of bromine to compounds of the formulae IIa and IIb is preferably 20:1 to 3:1, more preferably 10:1 to 5:1.

The imides of the formulae IIIa and IIIb obtained in reaction step a2) are generally used for the subsequent reaction without further purification.

Step a3)

In the reaction in step a3), the compounds of the formulae IIIa and IIIb obtained in step a2) are subjected to a cross-coupling with an organometallic compound of the formula IV.

Preference is given to effecting the reaction in the presence of catalytically active amounts of a transition metal of transition group VIII of the Periodic Table (group 10 according to IUPAC), for example nickel, palladium or platinum, especially in the presence of a palladium catalyst. Suitable catalysts are, for example, palladium-phosphine complexes such as tetrakis(triphenylphosphine)palladium(0), $PdCl_2$(o-tolyl$_3$P)$_2$, bis(triphenylphosphine)palladium(II) chloride, the [1,1'-bis(diphenyl-phosphino)ferrocene]palladium(II) chloride-dichloromethane complex, bis[1,2-bis(diphenylphosphino)ethane]palladium(0) and [1,4-bis(diphenylphosphino)-butane]palladium(II) chloride, palladium on activated carbon in the presence of phosphine compounds, and palladium(II) compounds such as palladium(II) chloride or bis(acetonitrile)palladium(II) chloride in the presence of phosphine compounds such as triphenylphosphine, 1,1'-bis(diphenylphosphino)ferrocene, 1,2-bis(diphenylphosphino)-ethane, 1,3-bis(diphenylphosphino)propane and 1,4-bis(diphenylphosphino)butane. The amount of catalyst is typically 10 to 150 mol %, based on the compounds of the formulae IIIa and IIb.

Especially suitable organometallic compounds IV are an appropriately substituted arylboronic acid and arylboronic esters (compounds IV where Met=B(OH)$_2$ or B(OR')(OR'') where R', R''=$C_1$-$C_4$-alkyl, or R' and R'' together are $C_2$-$C_4$-alkylene optionally bearing 1, 2, 3 or 4 substituents selected from $C_1$-$C_4$-alkyl).

The reaction is effected under the conditions of a Suzuki coupling, as known, for example, from Suzuki et al., Chem. Rev., 1995, 95, 2457-2483 and the literature cited therein. The arylboronic acids and esters thereof are known from the literature, commercially available, or can be prepared from the corresponding arylmagnesium compounds by reaction with appropriate boric esters.

Suitable organometallic compounds IV are especially also arylstannanes (compounds IV where Met=Sn(R*)$_3$ where R*=$C_1$-$C_4$-alkyl). In that case, the reaction is effected under the conditions of a Stille coupling, as known, for example, from D. Milstein, J. K. Stille, J. Am. Chem. Soc. 1978, 100, P. 3636-3638 or V. Farina, V. Krishnamurthy, W. J. Scott, Org. React. 1997, 50, 1-652. Arylstannanes IV can be prepared in analogy to known processes by reaction of aryllithium compounds with (R*)$_3$SnCl.

Suitable organometallic compounds IV are additionally organozinc compounds (compounds IV where Met=Zn-Hal where Hal=Cl, Br, especially Br). In that case, the reaction is effected under the conditions of a Negishi coupling, as known, for example, from A. Lützen, M. Hapke, Eur. J. Org. Chem., 2002, 2292-2297. Arylzinc compounds can be prepared in a manner known per se from the aryllithium compounds or from the arylmagnesium compounds by reaction with zinc salts such as zinc chloride.

The reaction of IIIa and IIIb with the organometallic compound IV, especially in the case of the Suzuki coupling, is effected under basic conditions. Suitable bases are alkali metal carbonates and alkali metal hydrogencarbonates such as sodium carbonate, potassium carbonate, cesium carbonate, sodium hydrogencarbonate, alkaline earth metal carbonates and alkaline earth metal hydrogencarbonates such as magnesium carbonate or magnesium hydrogencarbonate, or tertiary amines such as triethylamine, trimethylamine, triisopropylamine or N-ethyl-N-diisopropylamine.

Typically, the coupling of the compounds IIIa and IIIb with the compound IV is effected in a solvent. Suitable solvents are organic solvents such as aromatics, e.g. toluene, ethers, e.g. 1,2-dimethoxyethane, cyclic ethers such as tetrahydrofuran or 1,4-dioxane, polyalkylene glycols such as diethylene glycol, carbonitriles such as acetonitrile, propionitrile, carboxamides such as dimethylformamide or dimethylacetamide. In the Suzuki coupling, the aforementioned solvents can also be used in a mixture with water; for example, the ratio of organic solvent to water may be in the range from 5:1 to 1:5.

At least one mole of the organometallic compound IV is used per mole of bromine atom to be exchanged. It may be advantageous to use a 5 to 30% molar excess of organometallic compound of the formula IV per mole of bromine atom to be exchanged.

Step a4)

The separation and/or purification in step a4) can be effected by customary processes known to those skilled in the art, such as extraction, distillation, recrystallization, separation on suitable stationary phases, and a combination of these measures.

It may be advantageous to undertake a partial or full separation of the isomers obtained after reaction step a1) and/or a2).

The present invention further provides a cyanated naphthalenebenzimidazole compound of the formula I or a mixture of these, which corresponds to compounds of the formulae Ic and Id

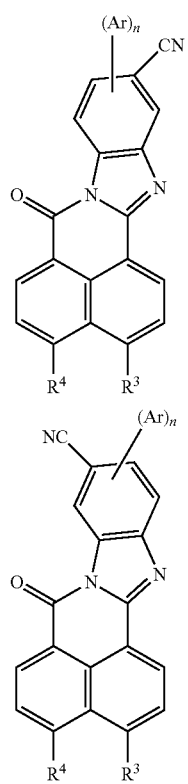

and mixtures thereof,
in which
R³ is aryl which is unsubstituted or mono- or polysubstituted by $R^{Ar}$;
R⁴ is aryl which is unsubstituted or mono- or polysubstituted by $R^{Ar}$;
Ar is aryl which is unsubstituted or mono- or polysubstituted by $R^{Ar}$;
$R^{Ar}$ is as defined above; and
n is 1 or 2,
obtainable by a process in which
b1) 4,5-dihalonaphthalic anhydride of the formula V

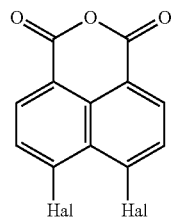

in which
Hal is bromine or chlorine is reacted with 3,4-diaminobenzonitrile to obtain compounds of the formulae VIa and VIb;

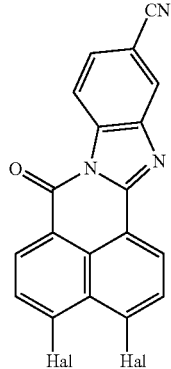

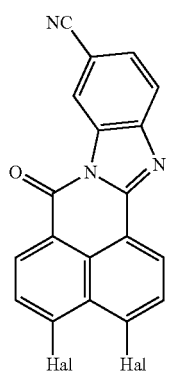

b2) the compounds of the formulae VIa and VIb obtained in step b1) are subjected to a bromination to obtain compounds of the formulae VIIa and VIIb

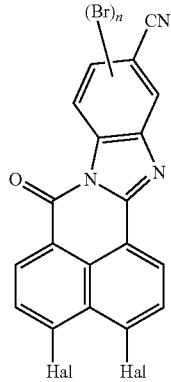

in which n is 1 or 2, b3) the compounds of the formulae VIIa and VIIb obtained in step b2) are subjected to a cross-coupling with an organometallic compound of the formula IV Ar-Met (IV)

in which

Ar is aryl which is mono- or polysubstituted by $R^{Ar}$; and

Met is $B(OH)_2$, $B(OR')(OR'')$, $Zn—R'''$ or $Sn(R^*)_3$, in which

R' and R" are each independently hydrogen, $C_1$-$C_{30}$-alkyl, $C_5$-$C_8$-cycloalkyl, $C_6$-$C_{14}$-aryl or hetaryl, or R' and R" together are $C_2$-$C_4$-alkylene which optionally bears 1, 2, 3, 4, 5, 6, 7 or 8 substituents selected from $C_1$-$C_4$-alkyl, $C_5$-$C_8$-cycloalkyl, $C_5$-$C_8$-aryl and heteroaryl, R''' is $C_1$-$C_8$-alkyl or phenyl and R* is $C_1$-$C_8$-alkyl or phenyl, in the presence of a transition metal catalyst to obtain compounds of the formulae Ic and Id, b4) the compounds of the formulae Ic and Id obtained in step b3) are optionally subjected to at least one separation and/or purification step.

Step b1)

In terms of the process, the procedure in step b1) is as described in step a1). 1,2-Diamino-3,5-diphenylbenzene is known from WO 2012/168395. 4,5-Dichloronaphthalic anhydride is known from Ukrainskii Khimicheskii Zhurnal (Russian Edition), 1952, vol. 18, p. 504, 507. 4,5-Dibromonaphthalic anhydride is known from Tesmer, Markus; Vahrenkamp, Heinrich; European Journal of Inorganic Chemistry, 2001, #5 p. 1183-1188.

Steps b2), b3) and b4)

In terms of the process, the procedure is as described in steps a2), a3) and a4).

It may be advantageous to undertake a partial or full separation of the isomers obtained after reaction step b1) and/or b2).

The present invention further provides a cyanated naphthalenebenzimidazole compound of the formula I or a mixture of these, which corresponds to a compound of the formulae Ie and/or If (Ie)

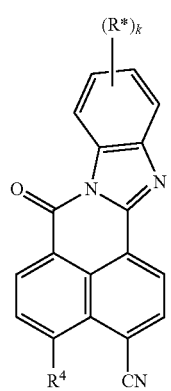

(If)

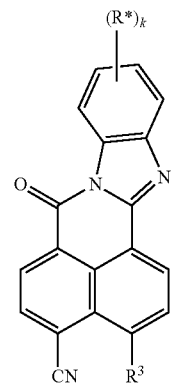

and mixtures thereof, in which $R^3$, if present, is aryl which is unsubstituted or mono- or polysubstituted by $R^{Ar}$;

$R^4$, if present, is aryl which is unsubstituted or mono- or polysubstituted by $R^{Ar}$;

each R* is independently cyano or aryl which is unsubstituted or has one or more identical or different substituents $R^{Ar}$, $R^{Ar}$ is as defined above; and k is 0, 1 or 2;

obtainable by a process in which c1) 4,5-dihalonaphthalic anhydride of the formula V (V)

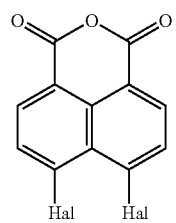

in which Hal is bromine or chlorine is reacted with a compound of the formula VIII (VIII)

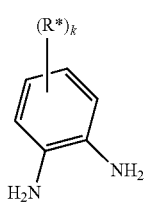

in which R* is as defined above; and k is 0, 1 or 2 to obtain compound of the formula IX (IX)

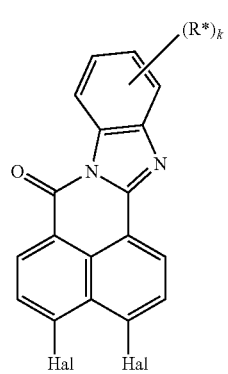

c2) the compound of the formula IX obtained in step c1) is subjected to a cross-coupling with an organometallic compound of the formula IV Ar-Met  (IV)

in which
Ar is aryl which is mono- or polysubstituted by $R^{Ar}$; and
Met is $B(OH)_2$, $B(OR')(OR'')$, $Zn-R'''$ or $Sn(R^*)_3$, in which
R' and R" are each independently hydrogen, $C_1$-$C_{30}$-alkyl, $C_5$-$C_8$-cycloalkyl, $C_6$-$C_{14}$-aryl or hetaryl, or R' and R" together are $C_2$-$C_4$-alkylene which optionally bears 1, 2, 3, 4, 5, 6, 7 or 8 substituents selected from $C_1$-$C_4$-alkyl, $C_5$-$C_8$-cycloalkyl, $C_5$-$C_8$-aryl and heteroaryl,
R''' is $C_1$-$C_8$-alkyl or phenyl and
R* is $C_1$-$C_8$-alkyl or phenyl,
in the presence of a transition metal catalyst to obtain compound(s) of the formulae Xa and/or Xb

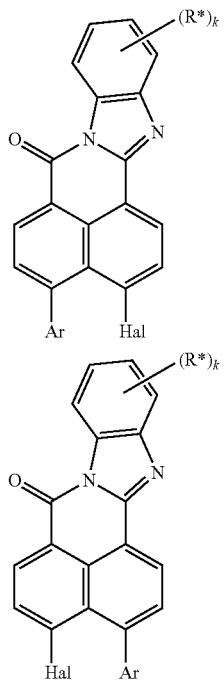

(Xa)

(Xb)

c3) if appropriate, the compounds of the formulae Xa and/or Xb obtained in step c2) are separated;
c4) the compound(s) of the formulae Xa and/or Xb obtained in step c2) or c3) are reacted with a metal cyanide to obtain compounds of the formulae Ie and/or If or
c2a) the compound of the formula IX obtained in step c1) is reacted with a metal cyanide to obtain compound(s) of the formula(e) XIa and/or XIb

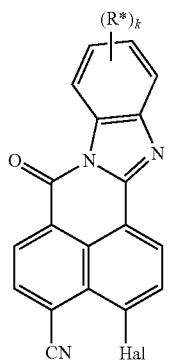

(XIa)

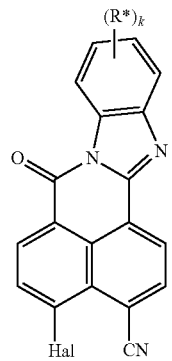

(XIb)

which is (are) optionally subjected to at least one separation and/or
c3a) the compound(s) of the formula(e) XIa and/are XIb obtained in step c2a) are subjected to a cross-coupling with an organometallic compound of the formula IV Ar-Met  (IV)

in which
Ar is aryl which is mono- or polysubstituted by $R^{Ar}$; and
Met is $B(OH)_2$, $B(OR')(OR'')$, $Zn-R'''$ or $Sn(R^*)_3$, in which
R' and R" are each independently hydrogen, $C_1$-$C_{30}$-alkyl, $C_5$-$C_8$-cycloalkyl, $C_6$-$C_{14}$-aryl or hetaryl, or R' and R" together are $C_2$-$C_4$-alkylene which optionally bears 1, 2, 3, 4, 5, 6, 7 or 8 substituents selected from $C_1$-$C_4$-alkyl, $C_5$-$C_8$-cycloalkyl, $C_5$-$C_8$-aryl and heteroaryl,
R''' is $C_1$-$C_8$-alkyl or phenyl and
R* is $C_1$-$C_8$-alkyl or phenyl,
in the presence of a transition metal catalyst to obtain compound(s) of the formula(e) Ie and/or If,
c5) the compound(s) of the formula(e) Ie and/or If obtained in step c4) or c3a) are optionally subjected to at least one separation and/or purification step.

Step c1)
In terms of the process, the procedure is as described in step b1). It will be appreciated that, when compounds of the formula VIII in which o is 1, 2 or 3 are used, 2 isomeric compounds of the formula IX are formed. In a preferred embodiment, the diamine of the formula VIII used is o-phenylenediamine or 3,4-diaminobenzonitrile.

Steps c2) and c3a)
In terms of the process, the procedure is as described in step b3).

Step c3)
The compounds of the formulae Xa and Xb may be separated by washing the precipitate with a $C_1$-$C_4$-alkanol and subsequently optionally with hot water to retain the compound of formula X in the filter, and the compound of formula Xb in the filtrate.

Steps c4) and c2a)
Suitable process conditions for cyano-dehalogenation are described in J. March, Advanced Organic Chemistry, 4th edition, John Wiley & Sons Publishers (1992), p. 660-661, and in WO 2004/029028. One example of these is reaction with copper cyanide. Additionally suitable are alkali metal cyanides such as KCN and NaCN, and also zinc cyanide. Typically, the cyanide source is used in excess. It may be advantageous to perform the reaction in the presence of zinc The reaction is generally effected in polar aprotic solvents in the presence of transition metals such as Pd(II) salts or Pd complexes, copper complexes or nickel complexes. The palladium catalyst can be prepared in situ from Pd(0) complexes such as tris(dibenzylideneacetone)-dipalladium (0) and 1,1'-bis(diphenylphosphino)ferrocene. Preferred polar aprotic solvents are dimethylformamide, N-methylpyrrolidone, $(CH_3)_2SO$, dimethyl sulfone and sulfolane. The reaction is performed typically at temperatures of 80 to 160° C., preferably 100 to 140° C., especially preferably 130 to 150° C. The molar ratio of halogen atom to be exchanged to zinc cyanide is typically 1:1 to 1:3, preferably 1.5:2.5. Alternatively, it is also possible to use CuCN in N-methylpyrrolidone or sulfolane in the absence of a catalyst.

Step c5)

In terms of the process, the procedure is as described in step a4).

It may be advantageous to undertake an early partial or full separation of the isomers obtained after reaction step c1) and/or c2). It may likewise be advantageous to undertake an early partial or full separation of the isomers obtained after reaction step c1) and/or c2a).

The present invention further provides a cyanated naphthalenebenzimidazole compound of the formula I or a mixture of these, which corresponds to a compound of the formula Ig

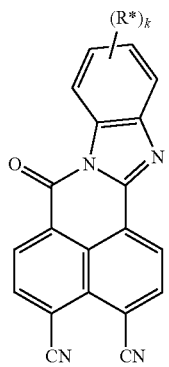

(Ig)

and mixtures thereof,
in which
R* is independently cyano or aryl which is unsubstituted or has one or more identical or different substituents $R^{Ar}$, where $R^{Ar}$ is as defined above; and
k is 0, 1 or 2;
obtainable by a process in which
d1) a compound of the formula IX

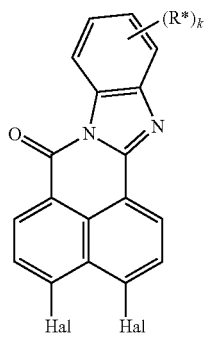

(IX)

in which
each R* is independently cyano or aryl which is unsubstituted or has one or more identical or different substituents $R^{Ar}$, where $R^{Ar}$ is as defined above;
k is 0, 1 or 2
is reacted with a metal cyanide to obtain a compound of the formula Ig,
and
d2) the compounds of the formula Ig obtained in step d1) are optionally subjected to at least one separation and/or purification step.

Step d1)

In terms of the process, the procedure is as described in step c4) or c2a).

Step d2)

In terms of the process, the procedure is as described in step a4).

The present invention further provides a cyanated naphthalenebenzimidazole compound of the formula I or a mixture of these, which corresponds to a compound Ih, Ii, Ik or Im

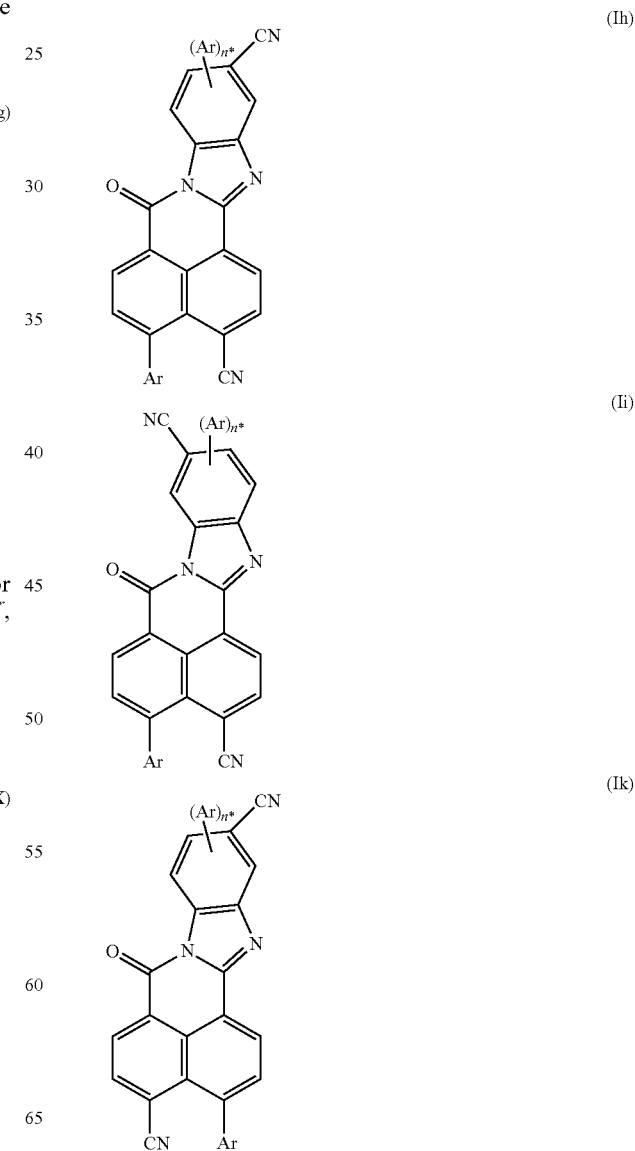

-continued

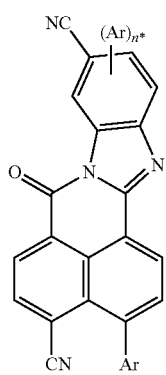
(Im)

or a mixture of these,
in which
Ar is aryl which is unsubstituted or mono- or polysubstituted by $R^{Ar}$ and $R^{Ar}$ is as defined above; and
n* is 0, 1 or 2;
obtainable by a process in which
e1) the compounds of the formulae VIIa and VIIb

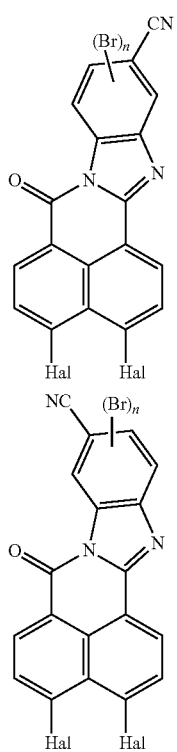
(VIIa)

(VIIb)

in which
n is 1 or 2,
are subjected to a substitution reaction, wherein one Hal and each bromine atom is substituted by aryl which is unsubstituted or has one or more identical or different substituents $R^{Ar}$, where $R^{Ar}$ is as defined defined above,
or
the compounds of the formulae (VIIa) and (VIIb) are subjected to a substitution reaction, wherein one Hal is substituted by aryl, and a part of the bromine atoms attached to the benzene ring of the benzimidazole moiety are substituted by aryl and the other bromine atoms that are not substituted by aryl, are substituted by hydrogen, where aryl is unsubstituted or has one or more identical or different substituents $R^{Ar}$, where $R^{Ar}$ is as defined above.

by cross-coupling with an organometallic compound of the formula IV $$\text{Ar-Met} \quad \quad (IV)$$

in which
Ar and Met are as defined above
in the presence of a transition metal catalyst to obtain compounds of the formulae XIIa, XIIb, XIIc and XIId

(XIIa)

(XIIb)

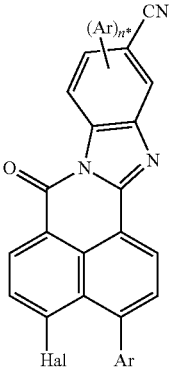
(XIIc)

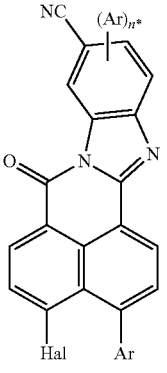
(XIId)

where n* is 0, 1 or 2; and

Ar is as defined above;

e2) if appropriate, the compounds of the formulae (XIIa), (XIIb), (XIIc) and (XIId) are separated to obtain a mixture of the compounds of formulae (XIIa) and (XIIb) and a mixture of the compounds of the formulae (XIIc) and (XIId);

e3) the compounds obtained in step e1) or e2) is (are) reacted with a metal cyanide to obtain compounds of the formulae Ih, Ii, and/or Ik and Im;

e4) the compound(s) of the formula(e) Ih, Ii and/or Ik or Im obtained in step e3) are optionally subjected to at least one separation and/or purification step.

Step e1)

In terms of the process, the procedure is as described in step c2)

Step e2)

In terms of the process, the procedure is as described in step c3).

Step e3)

In terms of the process, the procedure is as described in step c4).

Step e4)

In terms of the process, the procedure is as described in step c5)

Starting materials, if not commercially available, may be prepared by procedures selected from standard organic chemical techniques, techniques that are analogous to the synthesis of known, structurally similar compounds, or techniques that are analogous to the above described schemes or the procedures described in the synthetic examples section.

Other inventive compounds not described above may be prepared in analogy to the methods described herein.

The present invention further provides color converters comprising at least one polymer as a matrix material and at least one cyanated naphthalenebenzimidazole compound of the formula I or mixtures thereof as defined above as a fluorescent dye.

Suitable polymers are in principle all polymers capable of dissolving or homogeneously distributing the at least one cyanated naphthalenebenzimidazole compound of the formula I or mixtures in a sufficient amount.

Suitable polymers may be inorganic polymers or organic polymers.

Suitable inorganic polymers are, for example, silicates or silicon dioxide. A prerequisite for the use of inorganic polymers is that the at least one cyanated naphthalenebenzimidazole compound of the formula I or mixtures thereof can be dissolved or homogeneously distributed therein without decomposition. In the case of silicates or silicon dioxide, for example, this can be accomplished by deposition of the polymer from a waterglass solution.

In a preferred embodiment, the organic polymers consist essentially of polystyrene, polycarbonate, polymethylmethacrylate, polyvinylpyrrolidone, polymethacrylate, polyvinyl acetate, polyvinyl chloride, polybutene, silicone, polyacrylate, epoxy resin, polyvinyl alcohol, polyacrylonitrile, polyvinylidene chloride (PVDC), polystyreneacrylonitrile (SAN), polybutylene terephthalate (PBT), polyethylene terephthalate (PET), polyvinyl butyrate (PVB), polyvinyl chloride (PVC), polyamides, polyoxymethylenes, polyimides, polyetherimide or mixtures thereof.

Preferably, the at least one polymer consists essentially of polystyrene (PS), polycarbonate (PC), polymethylmethacrylate (PMMA), polyethylene terephthalate (PET) or mixtures thereof.

Most preferably, the at least one polymer consists essentially of polyethylene terephthalate, polystyrene or polycarbonate.

Polyethylene terephthalate is obtainable by condensation of ethylene glycol with terephthalic acid.

Polystyrene is understood here to mean, inter alia, all homo- or copolymers which result from polymerization of styrene and/or derivatives of styrene. Derivatives of styrene are, for example, alkylstyrenes such as alpha-methylstyrene, ortho-, meta-, para-methylstyrene, para-butylstyrene, especially para-tert-butylstyrene, alkoxystyrene such as para-methoxystyrene, para-butoxystyrene, para-tert-butoxystyrene.

In general, suitable polystyrenes have a mean molar mass $M_n$ of 10 000 to 1 000 000 g/mol (determined by GPC), preferably 20 000 to 750 000 g/mol, more preferably 30 000 to 500 000 g/mol.

In a preferred embodiment, the matrix of the color converter consists essentially or completely of a homopolymer of styrene or styrene derivatives.

In further preferred embodiments of the invention, the matrix consists essentially or completely of a styrene copolymer, which are likewise regarded as polystyrene in the context of this application. Styrene copolymers may comprise, as further constituents, for example, butadiene, acrylonitrile, maleic anhydride, vinylcarbazole or esters of acrylic, methacrylic or itaconic acid as monomers. Suitable styrene copolymers generally comprise at least 20% by weight of styrene, preferably at least 40% and more preferably at least 60% by weight of styrene. In another embodiment, they comprise at least 90% by weight of styrene.

Preferred styrene copolymers are styrene-acrylonitrile copolymers (SAN) and acrylonitrile-butadiene-styrene copolymers (ABS), styrene-1,1'-diphenylethene copolymers, acrylic ester-styrene-acrylonitrile copolymers (ASA), methyl methacrylate-acrylonitrile-butadiene-styrene copolymers (MABS).

A further preferred polymer is alpha-methylstyrene-acrylonitrile copolymer (AMSAN).

The styrene homo- or copolymers can be prepared, for example, by free-radical polymerization, cationic polymerization, anionic polymerization or under the influence of organometallic catalysts (for example Ziegler-Natta catalysis). This can lead to isotactic, syndiotactic or atactic polystyrene or copolymers. They are preferably prepared by free-radical polymerization. The polymerization can be performed as a suspension polymerization, emulsion polymerization, solution polymerization or bulk polymerization.

The preparation of suitable polystyrenes is described, for example, in Oscar Nuyken, Polystyrenes and Other Aromatic Polyvinyl Compounds, in Kricheldorf, Nuyken, Swift, New York 2005, p. 73-150 and references cited therein; and in Elias, Macromolecules, Weinheim 2007, p. 269-275.

Polycarbonates are polyesters of carbonic acid with aromatic or aliphatic dihydroxyl compounds. Preferred dihydroxyl compounds are, for example, methylenediphenylenedihydroxyl compounds, for example bisphenol A.

One means of preparing polycarbonates is the reaction of suitable dihydroxyl compounds with phosgene in an interfacial polymerization. Another means is the reaction with diesters of carbonic acid such as diphenyl carbonate in a condensation polymerization.

The preparation of suitable polycarbonates is described, for example, in Elias, Macromolecules, Weinheim 2007, p. 343-347.

In a preferred embodiment, polymers which have been polymerized with exclusion of oxygen are used. Preferably, the monomers during the polymerization comprised a total of not more than 1000 ppm of oxygen, more preferably not more than 100 ppm and especially preferably not more than 10 ppm.

Suitable polymers may comprise, as further constituents, additives such as flame retardants, antioxidants, light stabilizers, UV absorbers, free-radical scavengers, antistats. Stabilizers of this kind are known to those skilled in the art.

Suitable antioxidants or free-radical scavengers are, for example, phenols, especially sterically hindered phenols such as butylhydroxyanisole (BHA) or butylhydroxytoluene (BHT), or sterically hindered amines (HALS). Stabilizers of this kind are sold, for example, by BASF under the Irganox® trade name. In some cases, antioxidants and free-radical scavengers can be supplemented by secondary stabilizers such as phosphites or phosphonites, as sold, for example, by BASF under the Irgafos® trade name.

Suitable UV absorbers are, for example, benzotriazoles such as 2-(2-hydroxyphenyl)-2H-benzotriazole (BTZ), triazines such as (2-hydroxyphenyl)-s-triazine (HPT), hydroxybenzophenones (BP) or oxalanilides. UV absorbers of this kind are sold, for example, by BASF under the Uvinul® trade name.

In a preferred embodiment, TiO$_2$ is used as the sole UV absorber.

In a preferred embodiment of the invention, suitable polymers do not comprise any antioxidants or free-radical scavengers.

In a further embodiment of the invention, suitable polymers are transparent polymers.

In another embodiment, suitable polymers are opaque polymers.

The polymers mentioned serve as matrix material for suitable organic fluorescent dyes.

Especially preferably, the at least one cyanated naphthalenebenzimidazole compound of the formula I is selected from the compounds of the formulae (1) to (54) and mixtures thereof

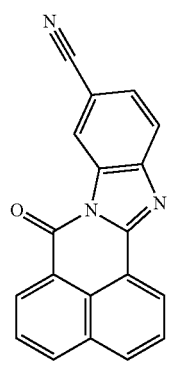

(1)

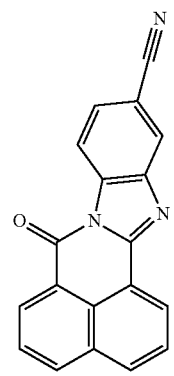

(2)

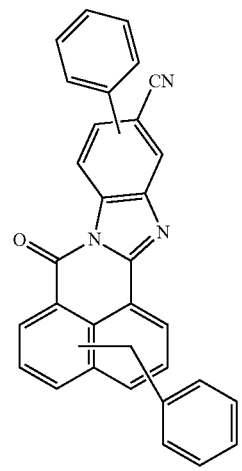

(3)

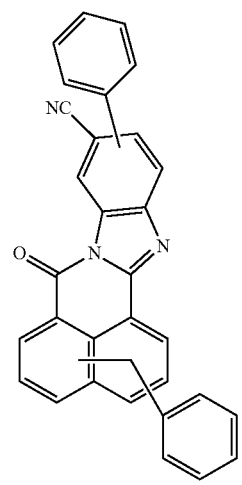

(4)

(5)
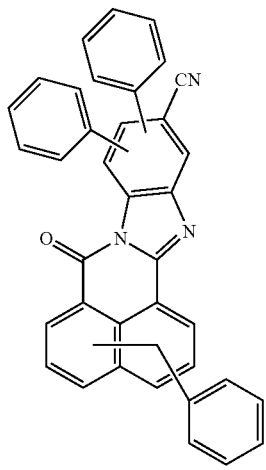
(6)
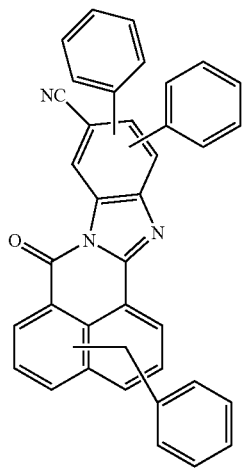
(7)
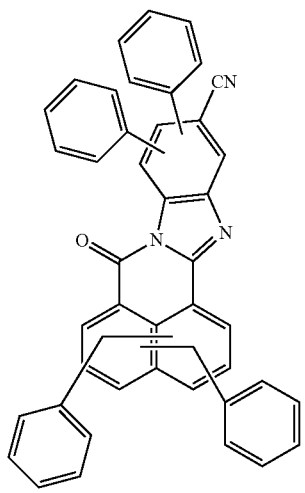
(8)
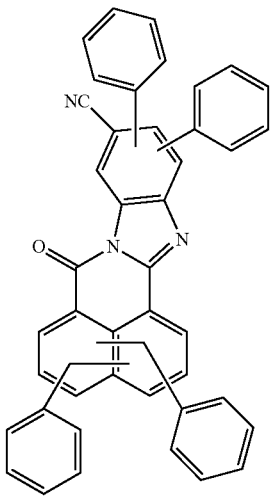
(9)
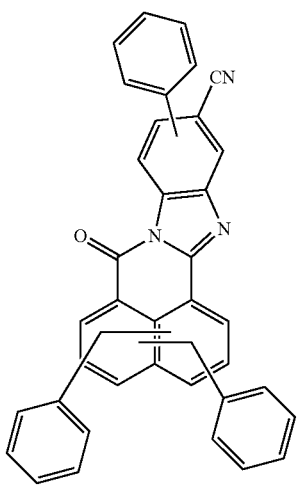
(10)
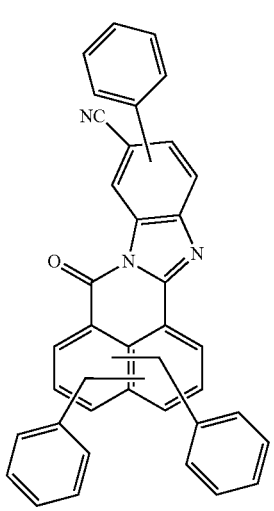

(11) 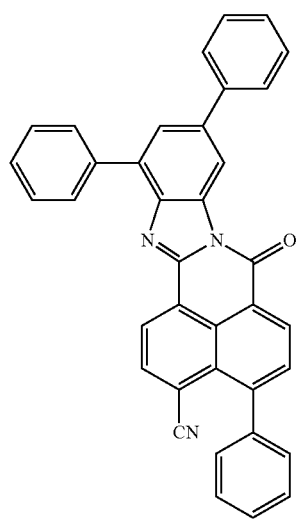
(12) 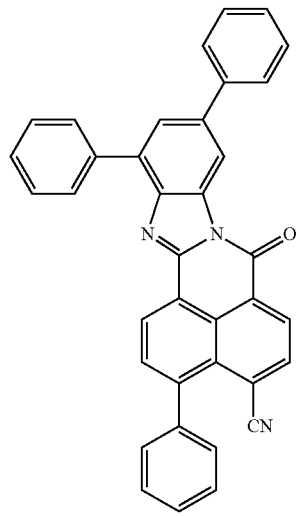
(13)
(14) 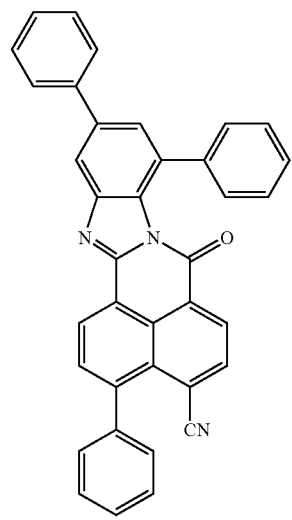
(15) 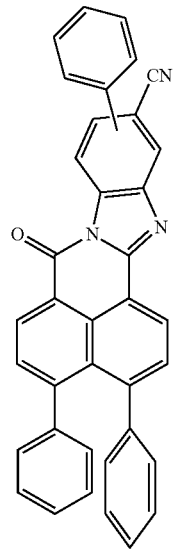
(16) 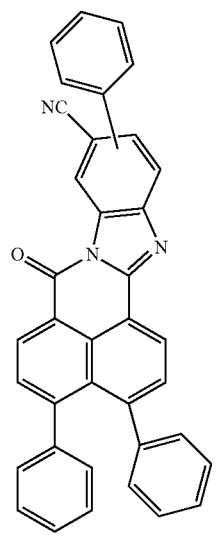

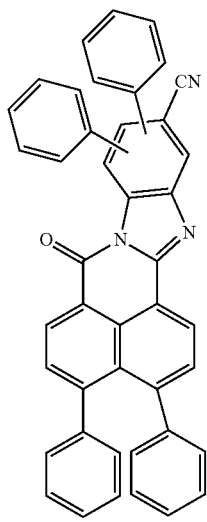 (17)
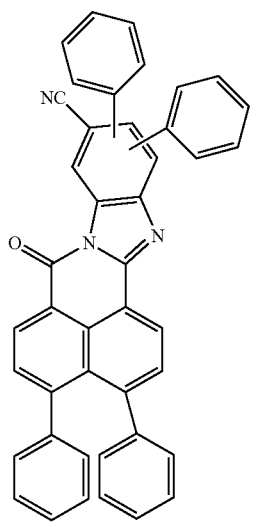 (18)
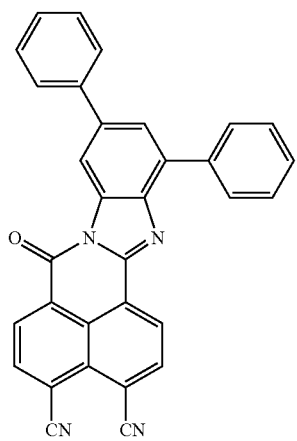 (19)
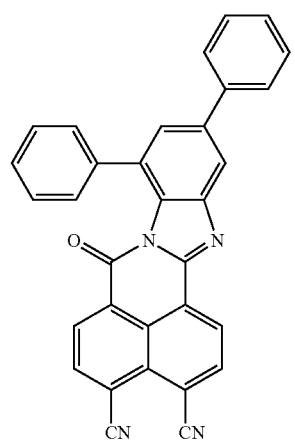 (20)
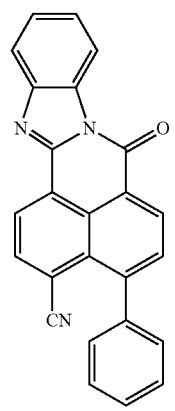 (21)
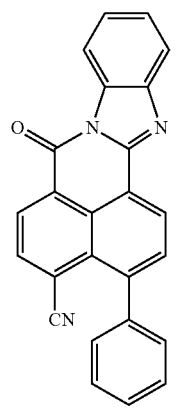 (22)

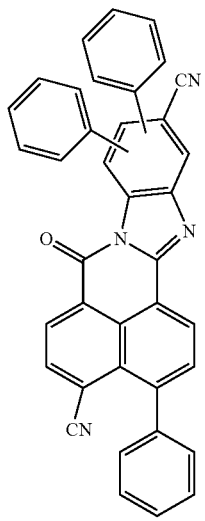
(23)
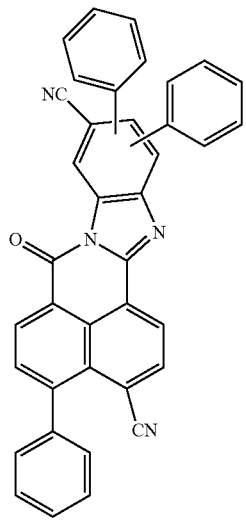
(24)
(25)
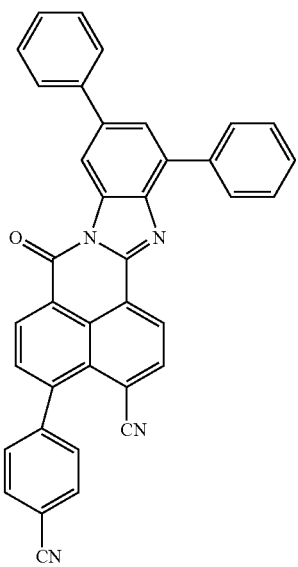
(26)
(27)
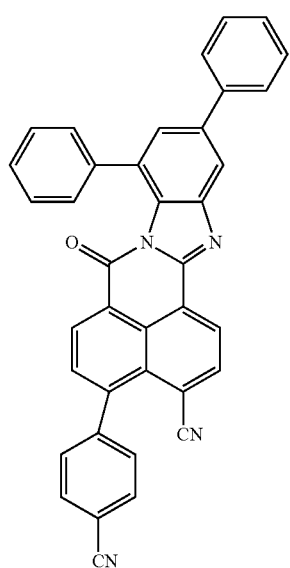
(28)

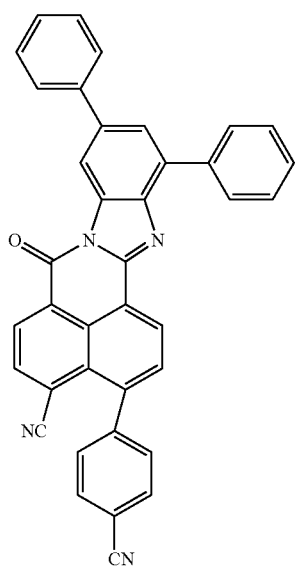 (29)
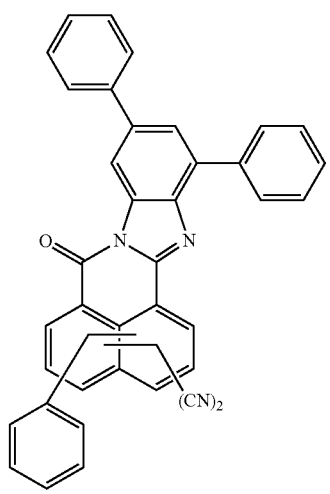 (32)
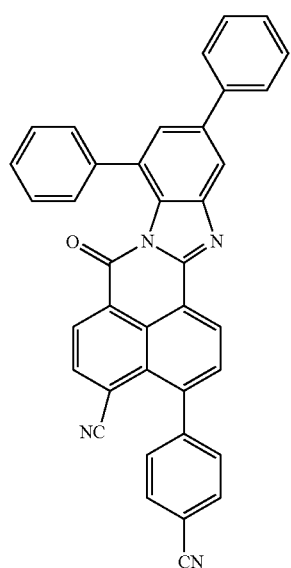 (30)
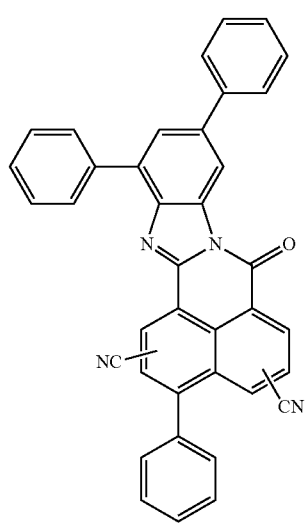 (33)
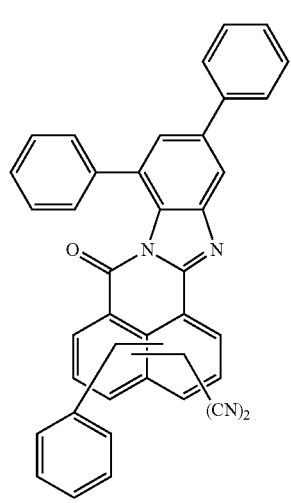 (31)
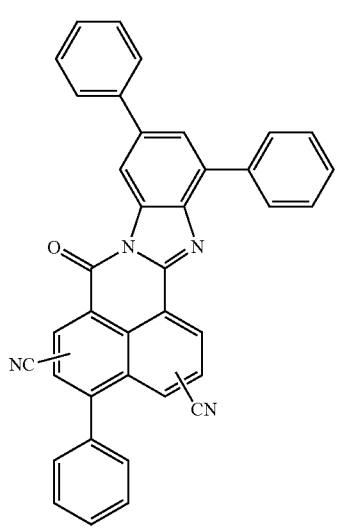 (34)

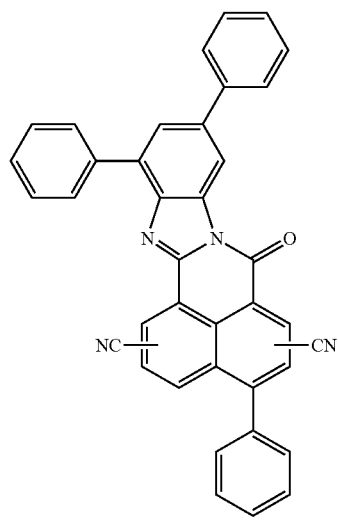
(35)
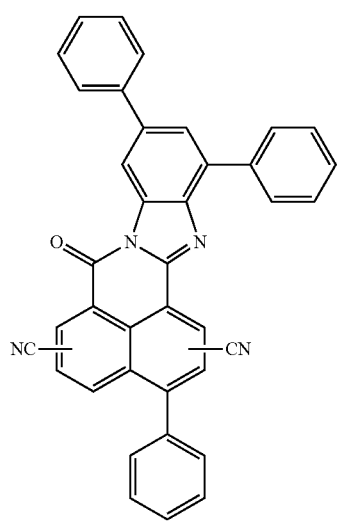
(36)
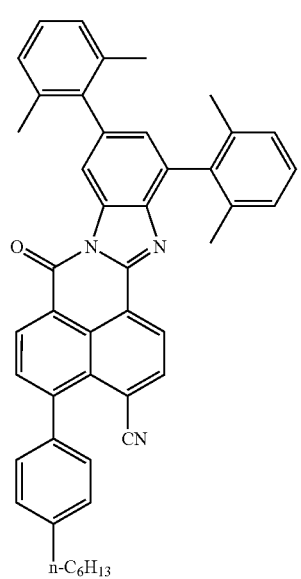
(37)
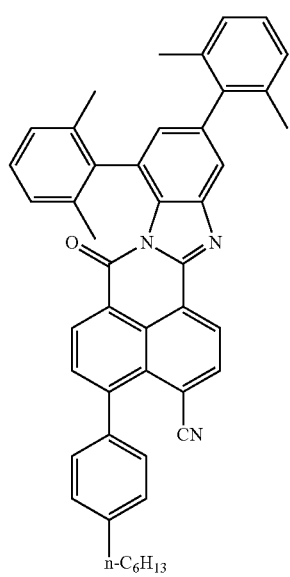
(38)
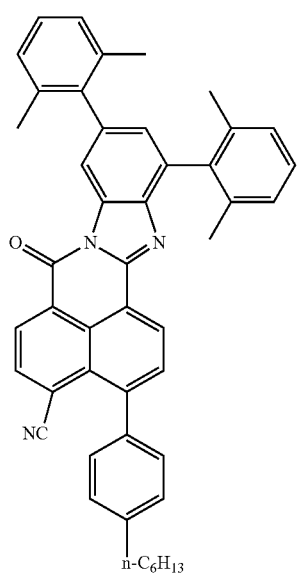
(39)

(40)
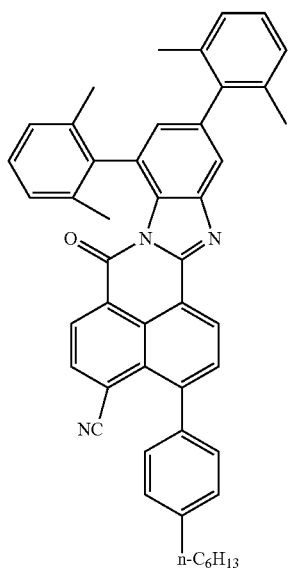
(41)
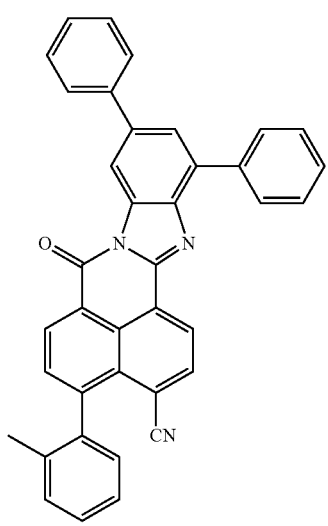
(42)
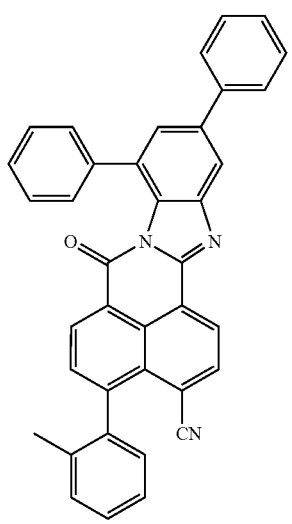
(43)
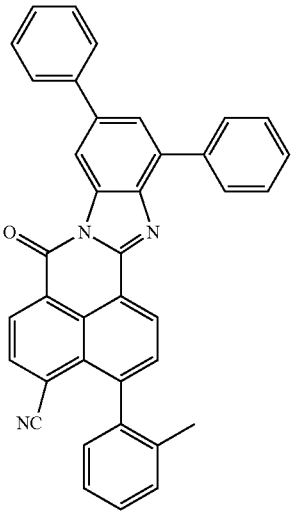
(44)
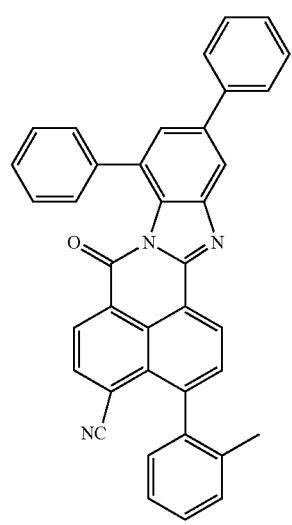
(49)
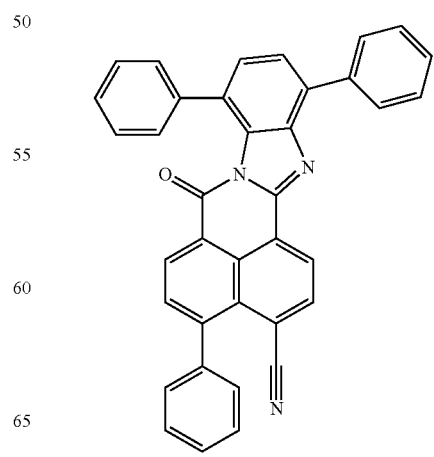

(50) 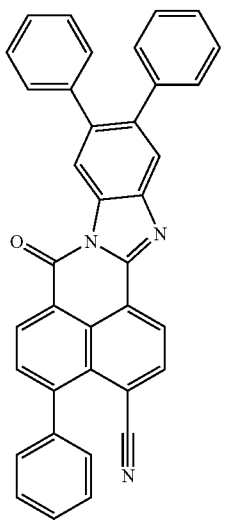

(51) 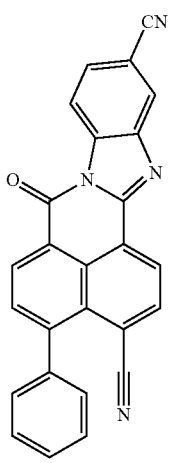

(52) 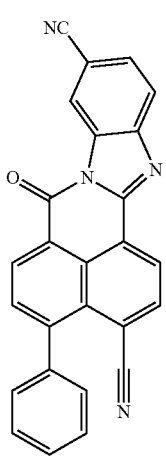

(53) 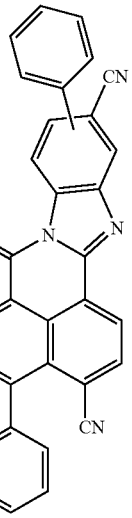

(54) 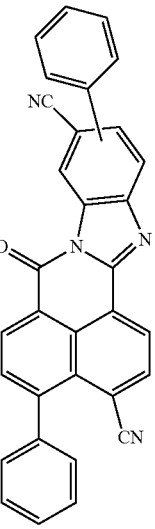

The inventive fluorescent dyes, i.e. the cyanated naphthalenebenzimidazole compounds of the formula I and mixtures thereof, may either be dissolved in the polymer or may be in the form of a homogeneously distributed mixture. The fluorescent dyes are preferably dissolved in the polymer.

In a preferred embodiment, color converters comprise, as well as the at least one inventive fluorescent dye of the compound of the formula I or mixtures thereof, further fluorescent colorants. For example, the at least one inventive organic fluorescent dye can be combined with a red-fluorescing fluorescent colorant. In many cases, fluorescent colorants are combined with one another such that color converters which can convert blue light to white light with good color rendering are obtained.

Suitable further fluorescent colorants are, for example, inorganic fluorescent colorants. Particularly preferred among these are those from the class of the rare earth-doped aluminates, silicates, nitrides and garnets. Further inorganic lighting colorants are, for example, those mentioned in "Luminescence—from Theory to Applications", Cees Ronda [ed.], Wiley-VCH, 2008, Chapter 7, "Luminescent Materials for Phosphor-Converted LEDs", Th. Jüstel, pages 179-190.

Garnets are compounds of the general formula $X_3Y_2[ZO_4]_3$ in which Z is a divalent cation such as Ca, Mg, Fe, Mn, Y is a trivalent cation such as Al, Fe, Cr, rare earths, and Z is Si, Al, $Fe^{3+}$, $Ga^{3+}$. The garnet is preferably yttrium aluminum garnet $Y_3Al_5O_{12}$ doped with $Ce^{3+}$, $Gd^{3+}$, $Sm^{3+}$, $Eu^{2+}$, $Eu^{3+}$, $Dy^{3+}$, $Tb^{3+}$ or mixtures thereof.

Suitable nitrides are described, for example, in U.S. Pat. No. 8,274,215. Suitable silicates are described, for example, in U.S. Pat. No. 7,906,041 and U.S. Pat. No. 7,311,858.

Suitable aluminates are described, for example, in U.S. Pat. No. 7,755,276.

Suitable aluminate phosphors of the formula $SrLu_{2-x}Al_4O_{12}:Ce_x$ in which x is a value from the range from 0.01 to 0.15 are known from WO2012010244. Luminophores of the composition $MLn_2QR_4O_{12}$ where M is at least one of the elements Mg, Ca, Sr or Ba, Ln is at least one of the elements Sc, Y, La, Ce, Pr, Nd, Sm, Eu, Gd, Tb, Dy, Ho, Er, Tm, Yb and Lu; Q is one of the elements Si, Ge, Sn, and Pb, and R, finally, is at least one of the elements B, Al, Ga, In and Tl are known from US 2004/0062699.

In addition, all organic red or pink fluorescent dyes are particularly suitable. In another embodiment, further fluorescent colorants comprise further orange- or yellow-fluorescing fluorescent dyes. Suitable organic fluorescent red dyes have, for example, the general formula

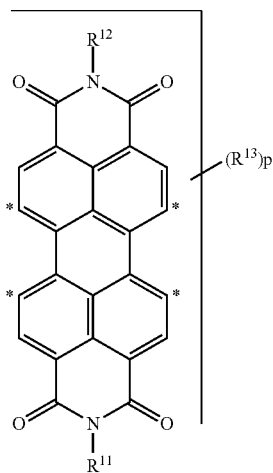

(XIV)

where
p is 1 to 4,
$R^{11}$, $R^{12}$ are each independently $C_1$-$C_{30}$-alkyl, $C_3$-$C_8$-cycloalkyl, aryl, hetaryl, aryl-$C_1$-$C_{10}$-alkylene, where the aromatic ring in the three latter radicals is unsubstituted or mono- or polysubstituted by $C_1$-$C_{10}$-alkyl, and
$R^{13}$ is $C_1$-$C_{30}$-alkoxy or aryloxy which is unsubstituted or mono- or polysubstituted by $C_1$-$C_{10}$-alkoxy, where the $R^{13}$ radicals are at one or more of the positions indicated by *.

Preferably, $R^{11}$ and $R^{12}$ are each independently selected from $C_1$-$C_{10}$-alkyl, 2,6-di($C_1$-$C_{10}$-alkyl)aryl and 2,4-di($C_1$-$C_{10}$-alkyl)aryl. More preferably, $R^{11}$ and $R^{12}$ are identical. Very particularly, $R^{11}$ and $R^{12}$ are each 2,6-diisopropylphenyl or 2,4-di-tert-butylphenyl.

$R^{13}$ is preferably phenoxy, or $C_1$-$C_{10}$-alkylphenoxy, more preferably 2,6-dialkylphenoxy, 2,4-dialkylphenoxy. Especially preferably $R^{13}$ is phenoxy, 2,6-diisopropylphenoxy, 2,4-di-tert-butylphenoxy or 4-tert-octylphenoxy.

More particularly, suitable further organic fluorescent dyes are selected from the compounds of the formulae XIV-1, XIV-2 and XIV-3

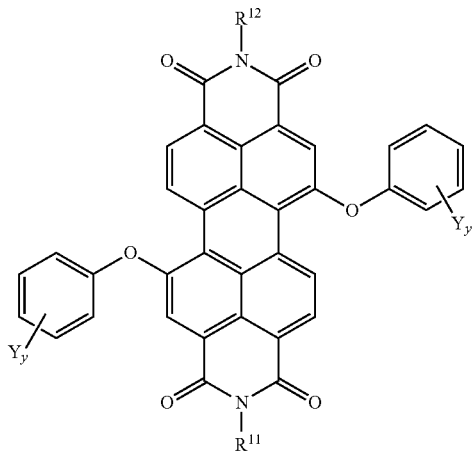

(XIV-1)

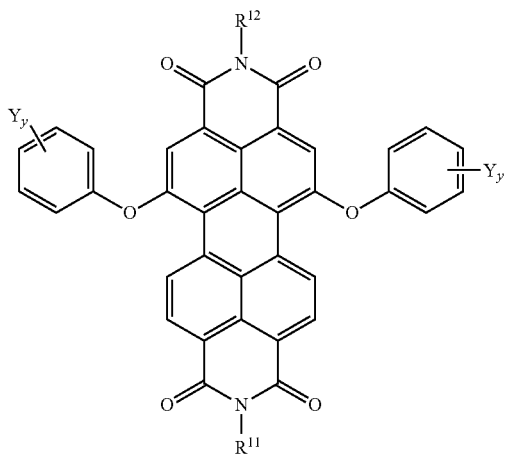

(XIV-2)

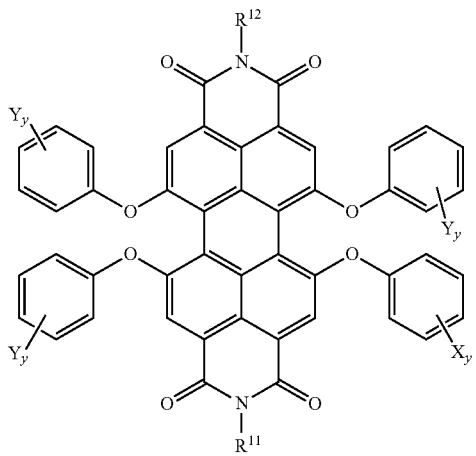

(XIV-3)

in which
$R^{11}$ and $R^{12}$ are each as defined above and especially as defined above with preference,
Y is linear or branched $C_1$-$C_{10}$-alkyl; and
y is 0, 1, 2, or 3.

Further examples of particularly suitable further organic fluorescent dyes are the perylene derivatives specified in WO2007/006717 at page 1 line 5 to page 22 line 6.

Particularly suitable further organic fluorescent dyes are N,N'-bis(2,6-diisopropylphenyl)-1,6,7,12-tetraphenoxyperylene-3,4;9,10-tetracarboximide, N,N'-bis(2,6-diisopropylphenyl)-1,7-di(2,6-diisopropylphenoxy)perylene-3,4;9,10-tetracarboximide, N,N'-bis(2,6-diisopropylphenyl)-1,6-di(2,6-diisopropylphenoxy)perylene-3,4;9,10-tetracarboximide, N,N'-bis(2,6-diisopropylphenyl)-1,7-di(p-tert-octylphenoxy)perylene-3,4;9,10-tetracarboximide, N,N'-bis(2,6-diisopropylphenyl)-1,6-di(p-tert-octylphenoxy)perylene-3,4;9,10-tetracarboximide, N,N'-bis(2,6-diisopropylphenyl)-1,7-diphenoxyperylene-3,4;9,10-tetracarboximide, N,N'-bis(2,6-diisopropylphenyl)-1,6-diphenoxyperylene-3,4;9,10-tetracarboximide. Preferably, the further organic fluorescent dye is selected from N,N'-bis(2,6-diisopropylphenyl)-1,7-di(2,6-diisopropylphenoxy)perylene-3,4;9,10-tetracarboximide, N,N'-bis(2,6-diisopropylphenyl)-1,6-di(2,6-diisopropylphenoxy)perylene-3,4;9,10-tetracarboximide and mixtures thereof.

In a further embodiment, inventive color converters additionally comprise at least one further organic fluorescent dye of the formula

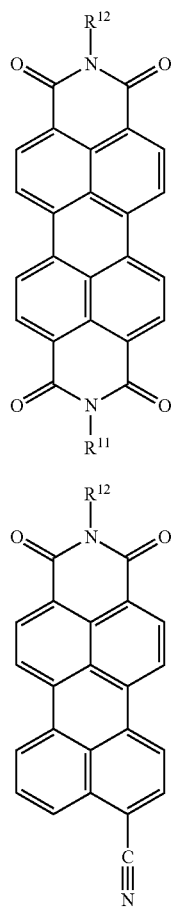

(XV)

(XVI)

where $R^{11}$ and $R^{12}$ are each as defined above.

In one embodiment of the invention, inventive color converters have a laminate structure. They may either have a monolayer structure or a multilayer structure, generally composed of a plurality of polymer layers comprising one or more fluorescent colorants and/or scattering bodies.

In one embodiment, the color converters consist of a plurality of polymer layers which have been laminated together to form a composite and wherein the various fluorescent colorants and/or scattering bodies may be present in different polymer layers.

If inventive color converters comprise more than one fluorescent colorant, it is possible in one embodiment of the invention for a plurality of fluorescent colorants to be present alongside one another in one layer.

In another embodiment, the various fluorescent colorants are present in various layers. In a preferred embodiment, inventive color converters comprise, as well as the at least one organic fluorescent dye present in accordance with the invention, at least one further organic fluorescent dye of formula (XIV), scattering bodies based on $TiO_2$ and at least one polymer consisting essentially of polystyrene, polyethylene terephthalate (PET) or polycarbonate.

In a further preferred embodiment, inventive color converters comprise, as well as the at least one organic fluorescent dye present in accordance with the invention, at least one further organic fluorescent dye of formula (XIV) and at least one further organic fluorescent dye of formula (XV) or (XVI), scattering bodies based on $TiO_2$ and at least one polymer consisting essentially of polystyrene, polyethylene terephthalate (PET) or polycarbonate.

In a particularly preferred embodiment, inventive color converters comprise, as well as the at least one organic fluorescent dye present in accordance with the invention, at least one further red organic fluorescent dye selected from N,N'-bis(2,6-diisopropylphenyl)-1,6,7,12-tetraphenoxyperylene-3,4;9,10-tetracarboximide, N,N'-bis(2,6-diisopropylphenyl)-1,7-di(2,6-diisopropylphenoxy)perylene-3,4;9,10-tetracarboximide, N,N'-bis(2,6-diisopropylphenyl)-1,6-di(2,6-diisopropylphenoxy)perylene-3,4;9,10-tetracarboximide, and at least one further organic fluorescent dye selected from N,N'-bis(2,6-diisopropylphenyl)perylene-3,4;9,10-tetracarboximide or N'-(2,6-diisopropylphenyl) perylene-9-cyano-3,4-dicarboximide, a scattering body based on $TiO_2$ and at least one polymer consisting essentially of polystyrene, polyethylene terephthalate or polycarbonate.

Typically, the concentration of inventive organic fluorescent dye of the formula I is 0.001 to 0.5% by weight, preferably 0.005 to 0.2% by weight, most preferably 0.01 to 0.1% by weight, based in each case on the amount of polymer used. Typically, the concentration of the red organic fluorescent dye is 0.0001 to 0.5% by weight, preferably 0.002 to 0.1% by weight, most preferably 0.005 to 0.05% by weight, based on the amount of the polymer used.

The ratio of at least one inventive organic fluorescent dye to at least one further red organic fluorescent dye is typically in the range from 4:1 to 25:1, preferably 6:1 to 20:1.

In a very particularly preferred embodiment, inventive color converters comprise compounds of the formula I selected from compounds of the formulae 3, 4, 5, 6, 7, 8, 9, 10, 11, 12, 13, 14, 21, 22, 25, 26, 37, 41, 45, 49, 50, 51, 52, 53, 54 and mixtures thereof as the inventive organic fluorescent dye, N,N'-bis(2,6-diisopropylphenyl)-1,7-di(2,6-diisopropylphenoxy)perylene-3,4;9,10-tetracarboximide, N,N'-bis(2,6-diisopropylphenyl)-1,6-di(2,6-diisopropylphenoxy)perylene-3,4;9,10-tetracarboximide as the red organic fluorescent dye, scattering bodies based on $TiO_2$, and at least one polymer consisting essentially of polystyrene.

In a very particularly preferred embodiment, inventive color converters comprise compounds of the formula I selected from compounds of the formulae 3, 4, 5, 6, 7, 8, 9, 10, 11, 12, 13, 14, 21, 22, 25, 26, 37, 41, 45, 49, 50, 51, 52, 53, 54 and mixtures thereof as the inventive organic fluorescent dye, N,N'-bis(2,6-diisopropylphenyl)-1,7-di(2,6-diisopropylphenoxy)perylene-3,4;9,10-tetracarboximide, N,N'-bis(2,6-diisopropylphenyl)-1,6-di(2,6-diisopropylphenoxy)perylene-3,4;9,10-tetracarboximide as the red organic fluorescent dye, scattering bodies based on $TiO_2$, and at least one polymer consisting essentially of PET.

In a very particularly preferred embodiment, inventive color converters comprise compounds of the formula I selected from compounds of the formulae 3, 4, 5, 6, 7, 8, 9, 10, 11, 12, 13, 14, 21, 22, 25, 26, 37, 41, 45, 49, 50, 51, 52, 53, 54 and mixtures thereof as the inventive organic fluorescent dye, N,N'-bis(2,6-diisopropylphenyl)-1,7-di(2,6-diisopropylphenoxy)perylene-3,4;9,10-tetracarboximide, N,N'-bis(2,6-diisopropylphenyl)-1,6-di(2,6-diisopropylphenoxy)perylene-3,4;9,10-tetracarboximide as the red organic fluorescent dye, scattering bodies based on $TiO_2$, and at least one polymer consisting essentially of polycarbonate.

If the color converter has a multilayer structure, in one embodiment, one layer comprises at least one red fluorescent dye and another layer at least one inventive fluorescent dye of the formula I or mixtures thereof.

In one embodiment, the at least one red organic fluorescent dye is in the layer of the color converter facing the LED. In another embodiment, the at least one green or green/yellow fluorescent dye is in the layer of the color converter facing the LED.

In a further embodiment, a scattering body is present in the layer facing the LED, above that a color converter and above that in turn optionally a further layer containing a scattering body.

In a preferred embodiment, the color converter has a bilayer structure with a red-fluorescing layer and a green/yellow-fluorescing layer comprising at least one fluorescent dye present in accordance with the invention, with the red layer facing the blue light source. In this embodiment, both layers comprise $TiO_2$ as a scattering body.

A further preferred embodiment of color converters has a monolayer structure, with at least one yellow fluorescent dye present in accordance with the invention and at least one red fluorescent dye of formula (XVI) and scattering bodies encompassed in one layer. The scattering body is preferably titanium dioxide. In this embodiment, the polymer preferably consists of polystyrene, PET or polycarbonate.

In one embodiment, at least one polymer layer of the color converter has been mechanically reinforced with glass fibers.

Inventive color converters may be in any desired geometric arrangement. The color converters may, for example, be in the form of films, sheets or plaques. Equally, the matrix containing organic fluorescent colorants may be in droplet form or hemispherical form or in the form of lenses with convex and/or concave, flat or spherical surfaces.

"Casting" refers to the embodiment where LEDs or components comprising LEDs are cast or enveloped fully with a polymer comprising organic fluorescent dye.

In one embodiment of the invention, the polymer layers (matrices) comprising organic fluorescent dye are 25 to 250 micrometers thick, preferably 35 to 200 μm and particularly 50 to 160 μm.

In another embodiment, the polymer layers comprising organic fluorescent dye are 0.2 to 5 millimeters thick, preferably 0.3 to 3 mm and more preferably 0.4 to 1 mm.

If the color converters consist of one layer or they have a laminate structure, the individual layers, in a preferred embodiment, are continuous and do not have any holes or interruptions.

The concentration of the organic fluorescent dyes in the polymer is set as a function of the thickness of the color converter and the type of polymer. If a thin polymer layer is used, the concentration of the organic fluorescent dye is generally higher than in the case of a thick polymer layer.

In a preferred embodiment, at least one of the layers or matrices comprising fluorescent dye comprises scattering bodies for light.

In a further preferred embodiment of the multilayer structure, a plurality of layers comprising fluorescent dye and one or more layers comprising scattering bodies without fluorescent dye are present.

Suitable scattering bodies are inorganic white pigments, for example titanium dioxide, barium sulfate, lithopone, zinc oxide, zinc sulfide, calcium carbonate having a mean particle size to DIN 13320 of 0.01 to 10 μm, preferably 0.1 to 1 μm, more preferably 0.15 to 0.4 μm.

Scattering bodies are typically present in an amount of 0.01 to 4.0% by weight, preferably 0.05 to 2% by weight, more preferably 0.1 to 1% by weight, based in each case on the polymer in the layer comprising scattering bodies.

Inventive color converters may optionally comprise further constituents such as a backing layer.

Backing layers serve to impart mechanical stability to the color converter. The type of material for the backing layers is not crucial, provided that it is transparent and has the desired mechanical strength. Suitable materials for backing layers are, for example, glass or transparent rigid organic polymers such as polycarbonate, polystyrene or polymethacrylates or polymethylmethacrylates.

Backing layers generally have a thickness of 0.1 mm to 10 mm, preferably 0.3 mm to 5 mm, more preferably 0.5 mm to 2 mm.

In one embodiment of the invention, inventive color converters have at least one barrier layer against oxygen and/or water, as disclosed in WO 2012/152812. Examples of suitable barrier materials for barrier layers are, for example, glass, quartz, metal oxides, $SiO_2$, a multilayer system composed of alternating layers of $Al_2O_3$ and $SiO_2$ layers, titanium nitride, $SiO_2$/metal oxide multilayer materials, polyvinyl alcohol, polyacrylonitrile, polyvinylidene chloride (PVDC), liquid crystal polymers (LCP), polystyrene-acrylonitrile (SAN), polybutylene terephthalate (PBT), polybutylene naphthalate (PBN), polyethylene terephthalate (PET), polyethylene naphthalate (PEN), polyvinyl butyrate (PVB), polyvinyl chloride (PVC), polyamides, polyoxymethylenes, polyimides, polyetherimides, epoxy resins, polymers which derive from ethylene-vinyl acetate (EVA) and polymers which derive from ethylene-vinyl alcohol (EVOH).

A preferred material for barrier layers is glass or a multilayer system composed of alternating layers of $Al_2O_3$ and $SiO_2$ layers.

Preferably, suitable barrier layers have low permeability for oxygen.

More preferably, suitable barrier layers have low permeability for oxygen and water.

Inventive color converters are especially suitable for the conversion of blue light to green/yellow light.

More particularly, they are suitable for conversion of light emitted by blue LEDs. Suitable LEDs are, for example, those based on gallium nitride (GaN) or indium gallium nitride (InGaN). Likewise possible is use for conversion of light produced by mercury lamps, by organic light-emitting diodes (OLEDs) or by UV LEDs.

Inventive color converters are also especially suitable for the conversion of green or white light to a more red-rich spectrum.

More particularly, they are suitable for conversion of light emitted by green LEDs. Suitable LEDs are, for example, those based on GaInNAs, such as Te-doped GaInNAs and Mg-doped GaInNAs. More particularly, they are suitable for conversion of light emitted by white LEDs to pleasant light with good color rendering.

They are additionally suitable for applications as a light-collecting system (fluorescence collector) in photovoltaics and in fluorescence conversion solar cells.

In a further embodiment, the inventive color converters are used for the conversion of blue light.

In a further embodiment, the color converter is used for conversion of light which has been produced by a blue diode, using at least one compound of the formula I or mixtures thereof as a fluorescent dye rather than Ce:YAG as a radiation converter. Preferably, the color converter comprises, as fluorescent dye, in addition to the inventive compound of the formula I or mixtures thereof, a red organic fluorescent dye. The red organic fluorescent dye is preferably selected from the compounds of the formulae XIV, XV and XVI. In this embodiment, the blue LED and the color converter are in a remote phosphor arrangement. The color rendering of such an LED meets high demands.

In a further embodiment, the color converter is used for conversion of light which has been produced by a blue diode, using at least one compound of the formula I or mixtures thereof as a fluorescent dye in combination with at least one inorganic fluorescent colorant selected from rare earth-doped aluminates, silicates, nitrides and garnets, especially cerium-doped yttrium aluminum garnet. In this embodiment, the blue LED and the color converter are in a remote phosphor arrangement.

Inventive color converters on irradiation with light, especially with blue LED light, exhibit a high quantum yield. In addition, they have a high photostability on illumination with blue light. Moreover, they are stable toward oxygen and water. They emit pleasant light with good color rendering. A further advantage is that the color converters comprising no rare earths can be provided. Inventive color converters comprising cyanated compounds of the formula I or mixtures thereof together with rare earth-doped inorganic fluorescers improve the color rendering value of a lighting device which has been produced with a blue LED and comprises Ce:YAG as converter material.

Inventive color converters can be produced by different processes.

In one embodiment, the process for producing inventive color converters comprises the dissolution of the at least one polymer and the at least one organic fluorescent dye in a solvent and subsequent removal of the solvent.

In another embodiment, the process for producing inventive color converters comprises the extrusion of the at least one organic fluorescent dye with the at least one polymer.

The invention further provides lighting devices comprising at least one LED and at least one inventive color converter. The at least one LED is preferably blue and emits light preferably within a wavelength range from 400 to 500 nm, preferably 420 to 480 nm, more preferably 440 to 470 nm, most preferably at 445 to 460 nm.

In one embodiment, inventive lighting devices comprise exactly one LED. In another embodiment, inventive lighting devices comprise two or more LEDs.

In one embodiment, inventive lighting devices comprise a plurality of LEDs, all of which are blue. In another embodiment, inventive lighting devices comprise a plurality of LEDs, at least one LED being blue and at least one LED not being blue but emitting light in another color, for example red.

Furthermore, the type of LED used is not crucial for the inventive lighting devices. In a preferred embodiment, the power density of the LED used is less than 100 mW/cm$^2$, preferably less than 60 mW/cm$^2$. The use of LEDs of higher power densities, such as 150 or 200 mW/cm$^2$, is likewise possible. However, a higher power density of the LED can reduce the lifetime of the fluorescent dyes and the color converters.

Inventive color converters can be used in combination with LEDs in virtually any geometric form and irrespective of the construction of the lighting device.

In one embodiment, color converter and LED are in a phosphor on a chip arrangement.

Preferably, inventive color converters are used in a remote phosphor setup. In this case, the color converter is spatially separated from the LED. In general, the distance between LED and color converter is from 0.1 cm to 50 cm, preferably 0.2 to 10 cm and most preferably 0.5 to 2 cm. Between color converter and LED may be different media such as air, noble gases, nitrogen or other gases or mixtures thereof.

The color converter may, for example, be arranged concentrically around the LED or have a planar geometry. It may take the form, for example, of a plaque, sheet or film, be in droplet form or take the form of a casting.

Inventive lighting devices are suitable for lighting in interiors, outdoors, of offices, of vehicles, in torches, games consoles, streetlights, traffic signs.

Inventive lighting devices exhibit a high quantum yield. In addition, they have a long lifetime, especially a high photostability on illumination with blue light. They emit pleasant light with good color rendering.

The present invention further provides a device producing electric power upon illumination comprising a photovoltaic cell (solar cell) and the color converter as defined above, where at least a part of the light not absorbed by the photovoltaic cell (solar cell) is absorbed by the color converter. The color converter is usually on top of the photovoltaic cell. The color converter is used to modify the spectrum such that UV and visible light are converted to a more bathochromic spectrum that is converted at higher efficiency by the solar cell.

EXAMPLES

Various fluorescent dyes were synthesized. The fluorescent dyes produced according to the examples were used to produce color converters. For this purpose, these were incorporated as described hereinafter into a matrix composed of a polymer. The polymer used was PMMA (Plexiglas® 6N from Evonik), polystyrene (PS168 N from BASF) and PC (Macrolon® 2808 from Bayer).

Production of the Color Converters for Testing of the Dyes:

About 2.5 g of polymer and 0.02% by weight of dye were dissolved in about 5 ml of methylene chloride, and 0.5% by weight of TiO$_2$ was dispersed therein, based in each case on the amount of polymer used. The solution/dispersion obtained was coated onto a glass surface using an applicator frame (wet film thickness 400 µm). After the solvent had dried off, the film was detached from the glass and dried in a vacuum drying cabinet at 50° C. overnight. Two circular film pieces having a diameter of 15 mm were punched out of each film of thickness 80 to 85 µm, and these served as analysis samples.

Fluorescence quantum yields (FQY) of the analysis samples were measured with the C9920-02 quantum yield measuring system (from Hamamatsu). This was done by illuminating each of the samples with light of 450 to 455 nm in an integration sphere (Ulbricht sphere). By comparison with the reference measurement in the Ulbricht sphere without sample, the unabsorbed fraction of the excitation light and the fluorescent light emitted by the sample are determined by means of a CCD spectrometer. Integration of the intensities over the spectrum of the unabsorbed excitation light or over that of the emitted fluorescent light gives the degree of absorption or fluorescence intensity or fluorescence quantum yield of each sample.

Example 1: Preparation of

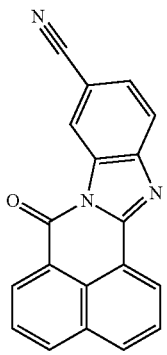

(1)

(2)

A mixture of 5.4 g (27 mmol) of 1,8-naphthalic anhydride, 4.05 g (30 mmol) of 3,4-diaminobenzonitrile, 4.95 g (27 mmol) of zinc acetate and 150 ml of quinoline was heated to 145° C. for 1 hour. Subsequently, 10 ml of ethanol were added, and the precipitate was filtered off and washed with ethanol and water. This gave the title compound as a yellowish precipitate (4.92 g, 62%).

Example 2: Preparation of

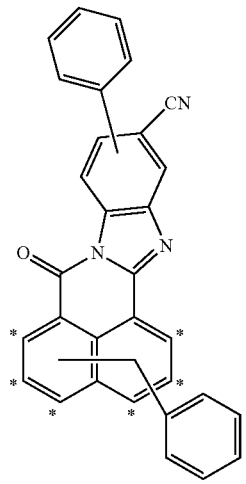

(3)

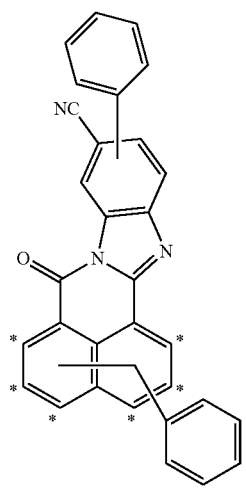

(4)

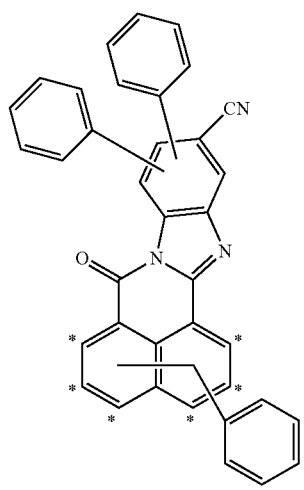

(5)

(6)

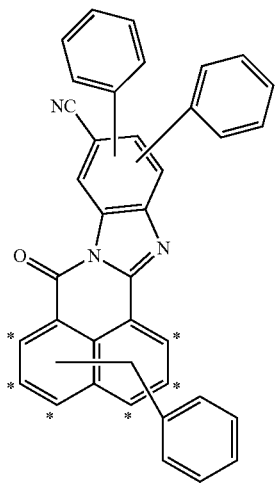

where phenyl attached to the naphthalene moiety is at one of the positions indicated by *

2.1 Preparation of

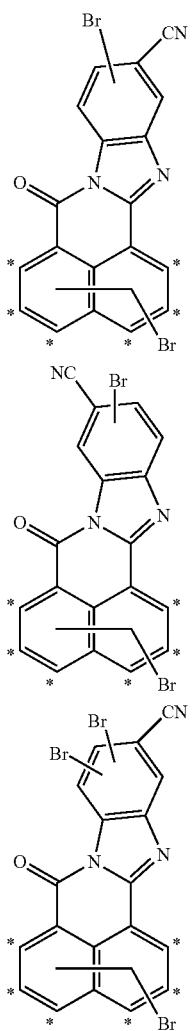

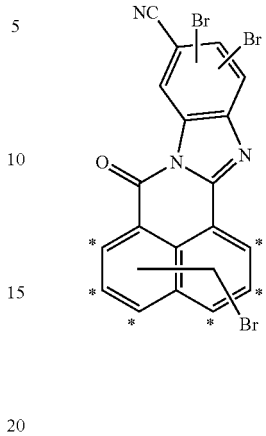

where Br attached to the naphthalene moiety is at one of the positions indicated by *

A mixture of 3.0 g (6.6 mmol) of the compounds from example 1, 8.0 g (100 mmol) of bromine and 150 ml of water was heated to reflux (55° C.) for three hours. Subsequently, the bromine was blown out, and the residue was filtered off and washed with hot water. This gave a mixture of dibrominated and tribrominated compounds.

2.2 Preparation of Compounds (3), (4), (5) and (6)

2.0 g (4.9 mmol) of the compounds from example 2.1, 3.6 g (29.4 mmol) of phenylboronic acid, 2.8 g (20 mmol) of potassium carbonate and 0.6 g (4.9 mmol) of tetrakistriphenylphosphinepalladium were heated in 100 ml of toluene to 90° C. for two hours. The reaction mixture was cooled, filtered, washed with toluene and worked up by column chromatography with silica gel and toluene. This gave 0.928 g of product which, according to mass spectroscopy analysis, consists of diphenylated and triphenylated title compounds (3), (4), (5) and (6).

Rf (toluene/ethyl acetate 10:1)=0.59

Emission: $\lambda_{max}$ (PS): 501 nm;

Emission: $\lambda_{max}$ (PC): 501 nm

FQY (polystyrene): 92%

The compound thus has a higher fluorescence quantum yield than the comparative compound from example 7 below.

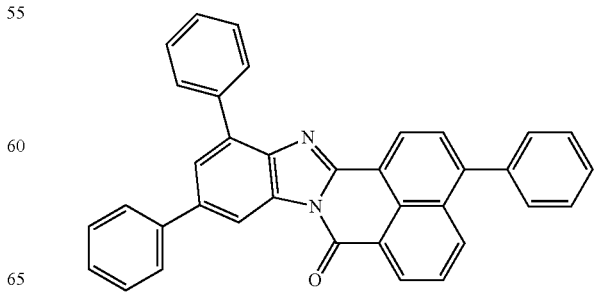

Example 3: Preparation of

(11)
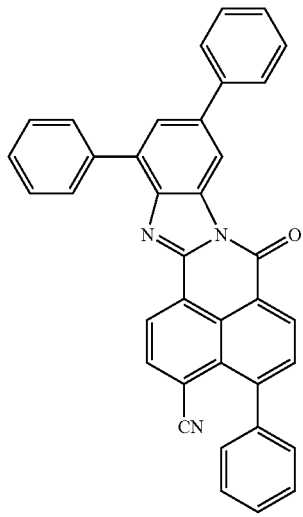

(12)
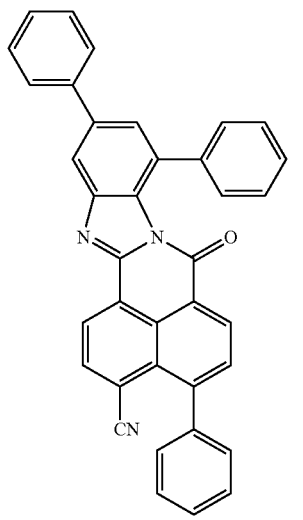

(13)
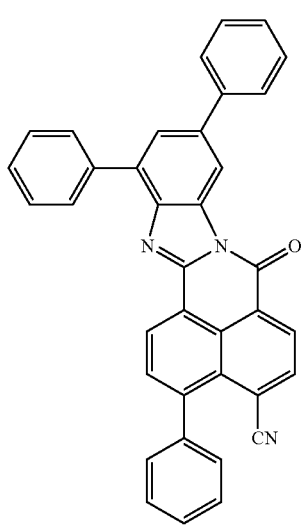

(14)
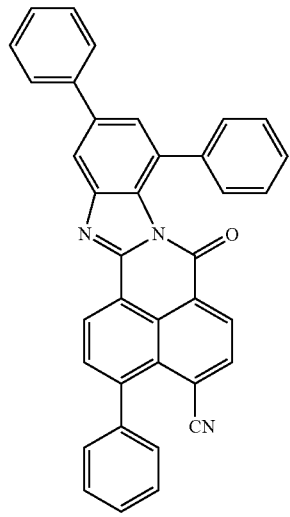

3.1 Preparation of

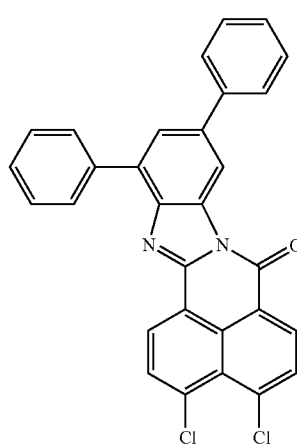

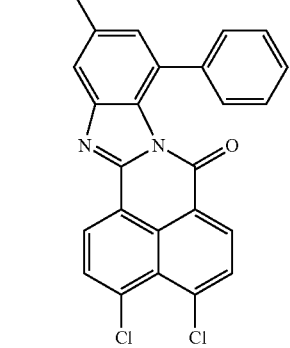

A mixture of 30 ml of quinoline, 2.69 g (10 mmol) of 4,5-dichloronaphthalic anhydride, 3.25 g (12.5 mmol) of 1,2-diamino-3,5-diphenylbenzene (obtainable as described in WO 2012/168395) and 1.83 g (10 mmol) of zinc acetate was heated to 145° C. for one hour. Subsequently, the reaction mixture was cooled and diluted with methanol. This gave 4.2 g (85%) of a yellow solid which consists of the two isomers described above.

3.2 Preparation of

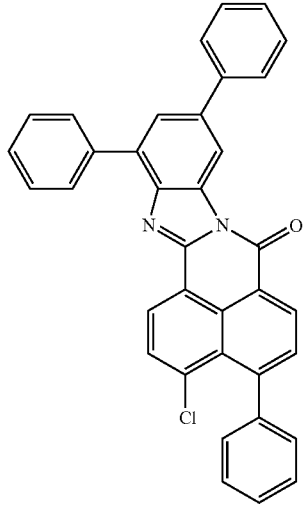
(B)

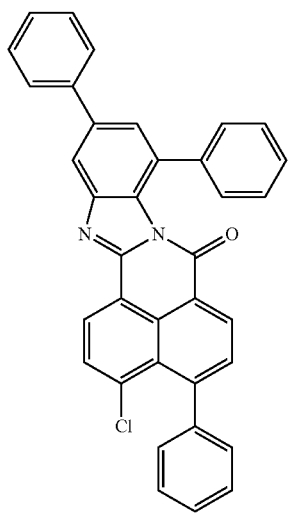
(C)

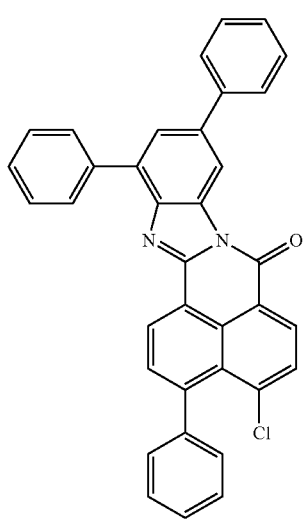
(D)

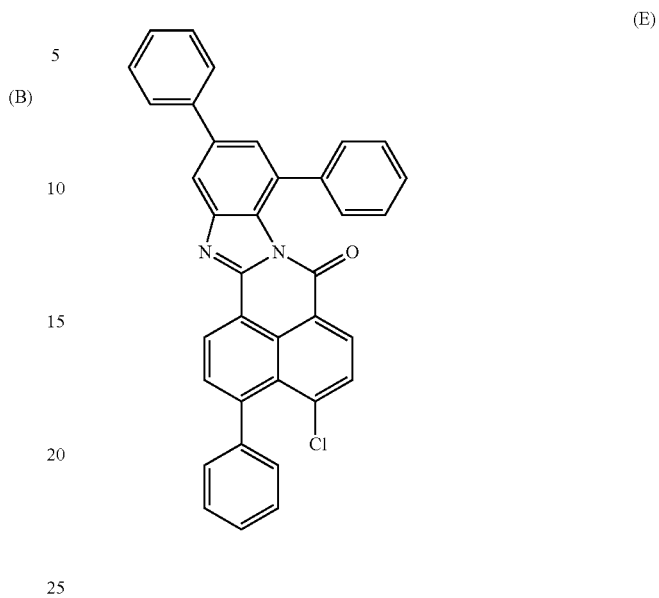
(E)

0.98 g (2 mmol) of the compounds from example 3.1, 0.24 g (2 mmol) of phenylboronic acid, 0.85 g (6 mmol) of potassium carbonate and 0.03 g (0.02 mmol) of tetrakistriphenylphosphinepalladium were heated in 25 ml of toluene to 90° C. for one hour. The reaction mixture was cooled and filtered. The filtrate was shaken with water against dichloromethane and isolated. Purification was effected on silica gel with toluene. This gave 0.738 g (70%) of a solid which, according to $^{13}$C NMR, consists of the isomers (B) and (D) and (C) and (E) in a ratio of 83:17.

Isomers (B) and (D): Rf (toluene)=0.56;

Isomers (C) and (E): Rf (toluene)=0.18.

3.3 Preparation of Isomers (11) and (13)

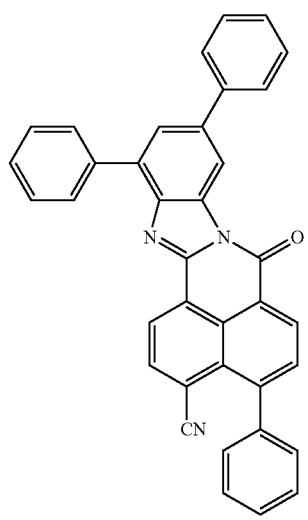
(11)

(13)

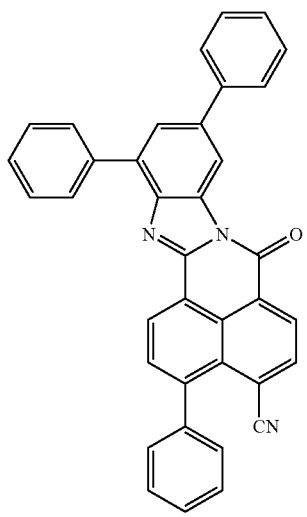

(14)

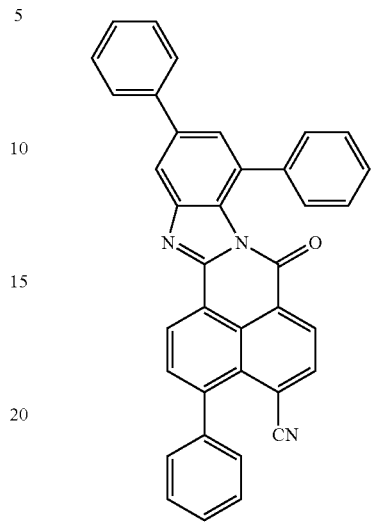

A mixture of 0.2 g (0.37 mmol) of the abovementioned compound (B) and (D) with Rf (toluene)=0.56, 0.087 g (0.07 mmol) of zinc cyanide, 0.3 g of tris(dibenzylidene-acetone)dipalladium and 0.1 g of 1,1'-bis(diphenylphosphino)ferrocene was heated in 10 ml of DMF to 150° C. for 2 hours. The reaction mixture was cooled, filtered and washed with water. The residue was purified with toluene on silica gel. This gives 61 mg (31%) of a yellow compound which, according to $^{13}C$ NMR, consists predominantly of isomer 11.

Rf (toluene)=0.55

Emission: $\lambda_{max}$ (PS): 551 nm

Emission: $\lambda_{max}$ (PC): 551 nm

FQY (polystyrene): 87%

Photostability lifetime T80 (80 mW/cm$^2$)=65 days in polycarbonate.

3.4 Preparation of Isomers (12) and (14)

The process described in example 3.3 was repeated, except that isomers (C) and (E) with Rf (toluene)=0.18 were used rather than isomers (B) and (D). This gave the title compounds as yellow-fluorescing compounds.

Rf (toluene/ethyl acetate 10:1)=0.51.

Emission: $\lambda_{max}$ (PS): 547 nm

Emission: $\lambda_{max}$ (PC): 547 nm

Example 4: Preparation of (12)

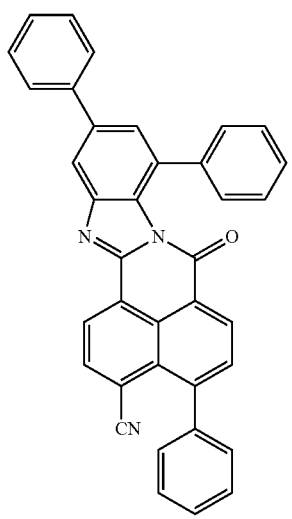

(15)

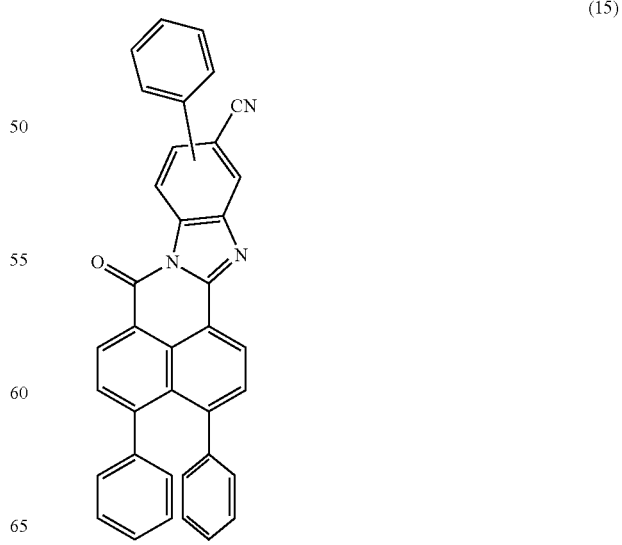

-continued

(16)
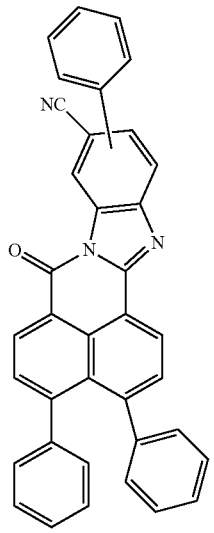

(17)
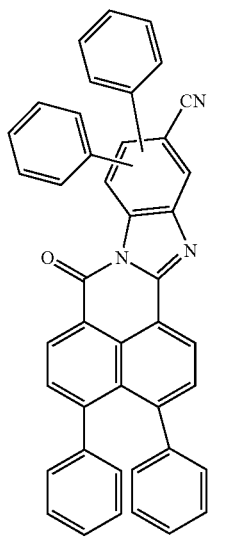

(18)
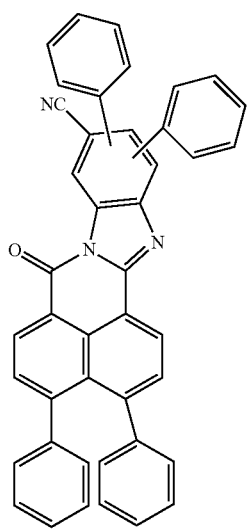

4.1 Preparation of

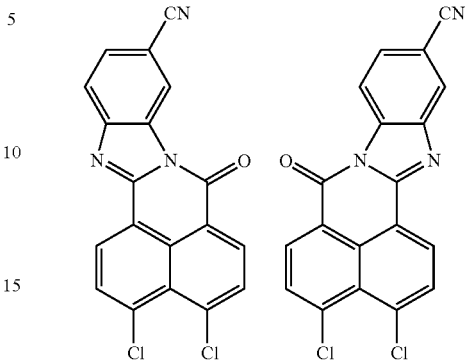

A mixture of 5.38 g (20 mmol) of 4,5-dichloronaphthalic anhydride, 2.7 g (25 mmol) of 3,4-diaminobenzonitrile, 3.66 g (20 mmol) of zinc acetate and 60 ml of quinoline was heated to 145° C. for two hours. Subsequently, the mixture was cooled to room temperature and methanol was added. The mixture was filtered and the solids obtained were washed with methanol and water. This gave 6.37 g (88%) of the title compound as a yellowish solid.

4.2 Preparation of

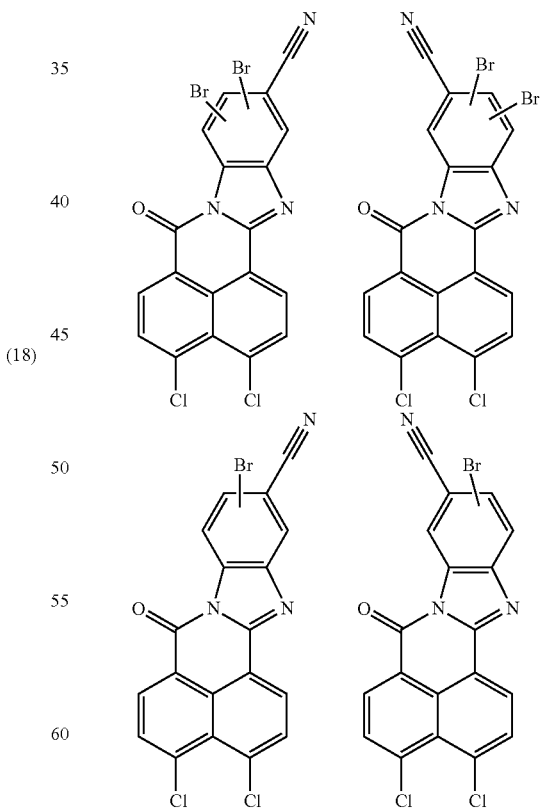

A mixture of 1.82 g (5 mmol) of the compounds from example 4.1, 1.6 g (20 mmol) of bromine and 120 ml of water is heated to reflux for three hours. A further 1.6 g (20 mmol) of bromine were added and the mixture was kept at reflux for a further 9 hours. Excess bromine was outgassed. The reaction mixture was filtered and the residue was washed with hot water. This gave 2.37 g of the title compounds, which are purified by column chromatography. According to mass spectroscopy analysis, the product consists of a mixture of monobrominated and dibrominated compounds.

4.3 Preparation of Compounds (15), (16), (17) and (18)

0.3 g of the mixture from example 4.2, 0.28 g (2.3 mmol) of phenylboronic acid, 0.23 g (1.7 mmol) of potassium carbonate, 30 mg (0.02 mmol) of tetrakistriphenylphosphine-palladium, 3 ml of water and 10 ml of toluene were heated to 90° C. for one hour. The mixture was cooled to room temperature and diluted with toluene, and the phases were separated. Purification was effected on silica gel with toluene. This gave 340 mg of the title compounds which, according to mass spectroscopy analysis, consist of a mixture of tri- and tetraphenylated title compounds (15), (16), (17) and (18). FQY (dichloromethane): 100%

Example 5: Preparation of

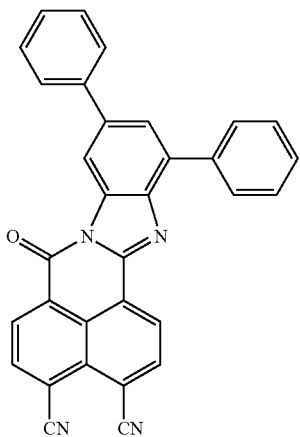
(19)

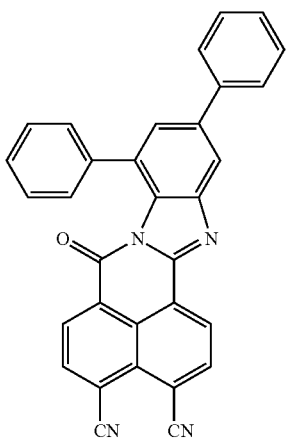
(20)

A mixture of 1.8 g (3.7 mmol) of the compounds from example 3.1, 1.74 g (14.8 mmol) of zinc cyanide, 1.5 g of tris(dibenzylideneacetone)dipalladium and 0.5 g of 1,1-bis-diphenylphosphinoferrocene was heated to 150° C. for two hours. The product was precipitated by addition of aqueous ammonia, filtered, washed with water and dried. Purification was effected on silica gel with toluene. Two products were isolated with Rf (toluene) values of 0.30 and 0.46.

Example 6: Preparation of

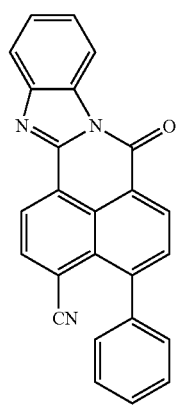
(21)

(22)

6.1 Preparation of

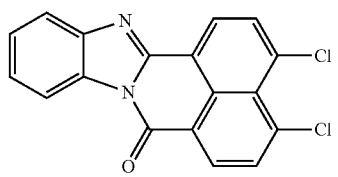 [SMILES: O=c1c2ccc(Cl)c3c(Cl)ccc(c32)c2nc3ccccc3n12]

A mixture of 5.38 g (20 mmol) of 4,5-dichloronaphthalic anhydride and 2.7 g (25 mmol) of o-phenylenediamine, 100 ml of quinoline, 3.66 g (20 mmol) of zinc acetate was heated to 145° C. for four hours. Subsequently, the mixture was cooled, filtered and washed with water. This gave 5.9 g (87%) of the title compound as a yellowish solid.

6.2 Preparation of

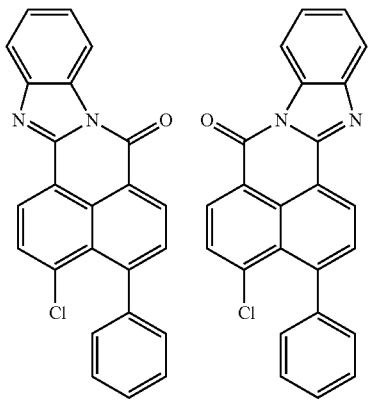

A mixture of 50 ml of toluene, 0.67 g (2 mmol) of the compound from example 6.1, 0.24 g (2 mmol) of phenylboronic acid, 0.85 g (6 mmol) of K2CO3, 5 ml of water, and 30 mg (0.02 mmol) of tetrakistriphenylphosphinepalladium was heated to 90° C. for two hours. Subsequently, the mixture was cooled to room temperature, filtered and washed with methanol. This gave 0.7 g (92%) of the title compounds as a yellow solid.

6.3 Preparation of

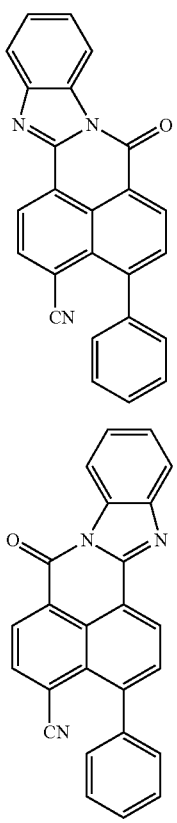

(21)

(22)

A mixture of 25 ml of dimethylformamide, 0.6 g (1.6 mmol) of the compounds from example 6.2, 0.87 g (7.4 mmol) of zinc cyanide, 0.75 g of tris(dibenzylideneacetone)-dipalladium (0.8 mmol) and 0.25 g (0.4 mmol) of 1,1'-bisdiphenylphosphinoferrocene was heated to 160° C. for two hours. Subsequently, another 0.2 g (0.5 mmol) of zinc cyanide was added thereto and the mixture was heated to 160° C. for a further two hours. The reaction mixture was cooled, admixed with aqueous ammonia and filtered, and washed with water. The residue was chromatographed with toluene on silica gel. This gave 115 mg of the title compounds (21) and (22) as yellow-fluorescing compounds.

Rf (toluene/ethyl acetate 40:1)=0.38.

Example 7: Comparative Example (Example 10 from WO 2012/168395)

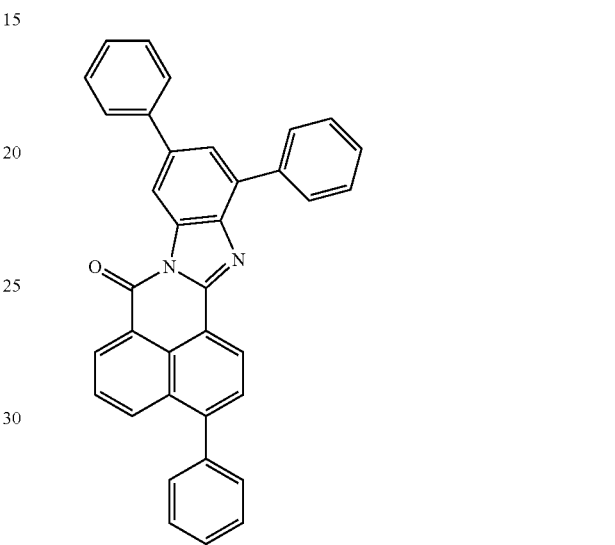

FQY (polystyrene) 86%
Photostability lifetime T80 (80 mW/cm$^2$) 12 days (polystyrene), 19 days (polycarbonate)

Example 8: Preparation of

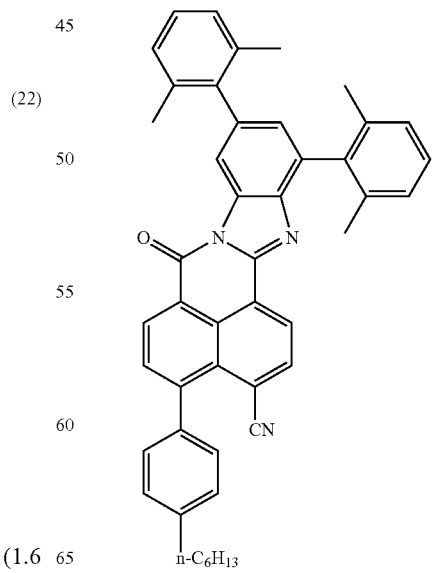

8.1 Preparation 2,4-bis(2,6-dimethylphenyl)-6-nitro-aniline

A mixture of 200 ml of toluene, 20 ml of 2-methyl-2-butanol, 5.4 g (18.4 mmol) of 2,4-dibromo-6-nitroaniline, 5.5 g (36.8 mmol) of 2,6-dimethylphenylboronic acid, 9.7 g (45.9 mmol) of potassium phosphate, 10 ml of water, 0.2 g (0.218 mmol) of tris(dibenzylidenacetone)dipalladium and 0.34 g (0.828 mmol) of S Phos (2-dicyclohexylphosphino-2',6'-dimethoxybiphenyl) were heated under nitrogen at 80° C. for 6 h and then at 90° C. for 16 h. After evaporation of the solvent, the residue was crystallized from petrol ether having a temperature of 40° C. This gave 6.44 g (quant.) of a solid having a HPLC purity of 89%.

Rf (toluene)=0.57

8.2 Preparation of 3,5-bis(2,6-dimethylphenyl)benzene-1,2-diamine

A mixture of 3.46 g (0.01 mol) of the compound of example 8.1, 90 ml of ethanol, 7.58 g (0.04 mol) of SnCl$_2$ were heated under reflux for 2 h. Then, further 2.0 g (0.01 mol) of SnCl$_2$ were added and the mixture was heated under reflux for 16 h. The solvent was removed under reduced pressure; the residue was taken up in dichloromethane and extracted with dichloromethane. This gave 1.36 g (43%) of the title compound.

Rf (toluene)=0.24

8.3 Preparation of

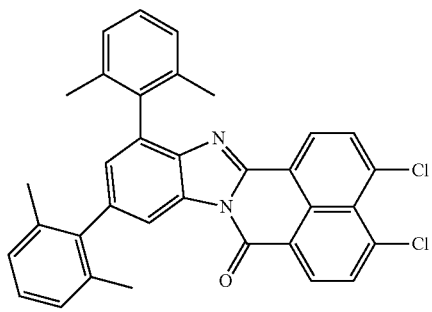

A mixture of 20 ml of quinoline, 1.04 g (3.8 mmol) of 4,5-dichloronaphthalic anhydride, 1.2 g (3.8 mmol) of the compound of example 8.2 and 0.7 g (3.8 mmol) of zinc(II) acetate was heated to 100° C. for 2 h. The reaction mixture was cooled to room temperature, filtered and the residue obtained was washed with 20 ml of methanol, subsequently with 0.5 l of hot water and dried under reduced pressure to give 1.44 g (69%) of a yellow solid.

Rf (toluene:ethyl acetate=10:1)=0.85

8.4 Preparation of

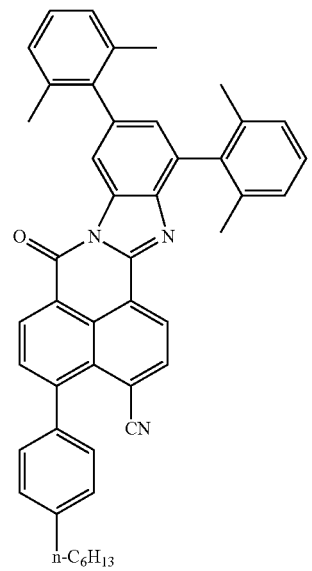

A mixture of 12 ml of toluene, 0.6 g (1.1 mmol) of the compound of example 8.3, 227 mg (0.001 mmol) of n-hexylphenylboronic acid, 0.44 g of potassium carbonate and 1.27 mg of tetrakistriphenylphosphinepalladium was heated to 80° C. for 2 h. The reaction mixture was concentrated; 6 ml of petrol ether were added and then the mixture was stirred for 2 h. The mixture was filtered and washed with 10 ml of methanol followed by 0.5 l of hot water to give 0.87 g of a yellow mixture comprising 52% of the title compound having a Rf (toluene) of 0.72 and 43% of a biphenylated compound according to HPLC.

8.5 Preparation of

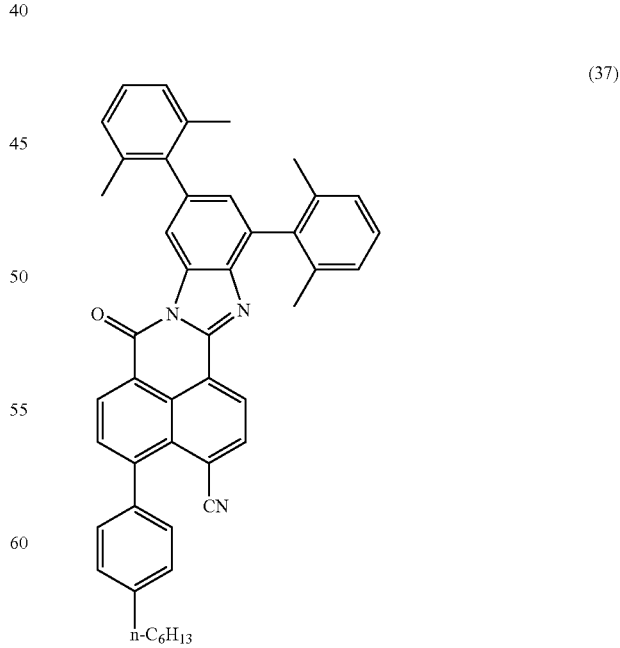

(37)

20 ml of dimethylformamide (DMF), 1.28 g (1.9 mmol) of the compound of example 8.4 with R$_f$ (toluene)=0.72, 0.18 g (1.6 mmol) of zinc(II) cyanide, 0.08 g of zinc, 0.25 g (0.3 mmol) tris(dibenzylidenacetone)dipalladium and 0.16 g (0.3 mmol) 1,1'-bis(diphenyl-phosphino)ferrocen were heated to 60° C. for two hours. Subsequently, further 0.18 g (1.6 mmol) of zinc cyanide were added and the mixture was heated to 60° C. for further 5 h. The mixture was cooled, diluted with water and filtrated to give 1.29 g of the crude title compound which was purified with toluene on silica gel. This gave 0.376 g (29%) of the title compound. Rf (toluene)=0.17

$\lambda_{max}$ (dichloromethane): 423 nm

Example 9: Preparation of

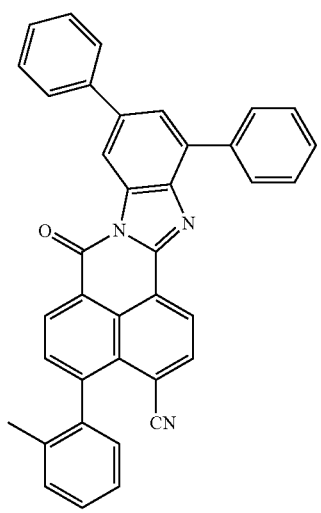

(41)

9.1 Preparation of

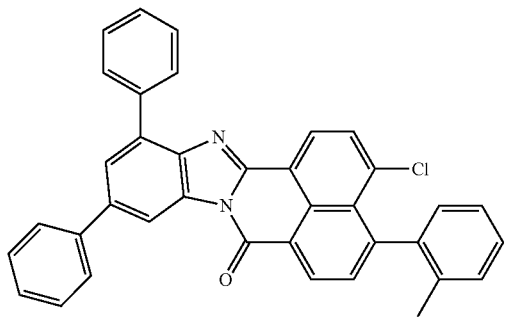

A mixture of 1.12 g (2.3 mmol) of the compounds of example 3.1, 50 ml of N-methyl-2-pyrrolidone (NMP), 2.5 ml of 2-methyl-2-butanol, 0.31 g (2.3 mmol) of 2-methyl-phenylboronic acid, a solution of 1.21 g of potassium phosphate in 1.5 ml of water, 0.025 g of tris(dibenzylideneacetone)dipalladium and 0.043 g of S-Phos were heated to 65° C. for 14 h. Then, the same amount of catalyst (tris(dibenzylidene-acetone)dipalladium) and ligand (S-Phos) was added and the mixture was stirred for further 3 h, followed by the addition of the same amount of catalyst and further stirring to 65° C. for further 60 h to give 0.85 g of the crude title product which was purified by column chromatography on silica gel to give 0.19 g (15%) of the title compound.

Rf (toluene: petrol ether=4:1)=0.44.

9.2 Preparation of

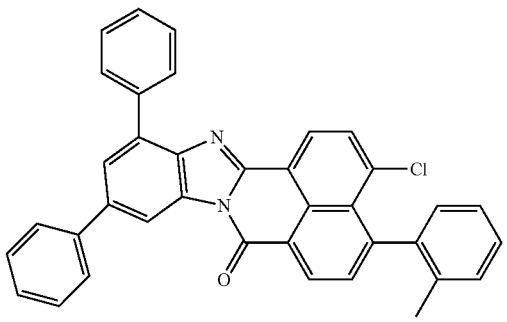 [SMILES: Cc1ccccc1-c1ccc2c(=O)n3c4cc(-c5ccccc5)cc(-c5ccccc5)c4nc3c3ccc(Cl)c1c23]

(41)

A mixture of 10 ml of DMF, 0.15 g (0.27 mmol) of the compound of example 9.1, 0.05 g (0.42 mmol) of zinc cyanide, 0.022 g of zinc (0.33 mmol), 0.07 g of tris(dibenzylideneacetone)dipalladium and 0.044 g of 1,1' bis(diphenylphosphino-ferrocene) was stirred at 60° C. for 2 hours. Then, the same amount of zinc cyanide was added and the mixture was heated to 60° C. for 3 hours. Water was added, the mixture was filtrated, the residue was washed and dried to give 300 mg of the crude title product, which was purified on silica gel (eluent: toluene petrol ether 4:1) and crystallized with toluene.

Rf (toluene etrol ether 4:1)=0.34

Example 10: Preparation of

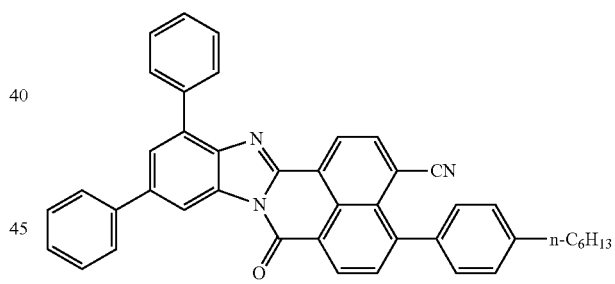

(45)

10.1 Preparation of

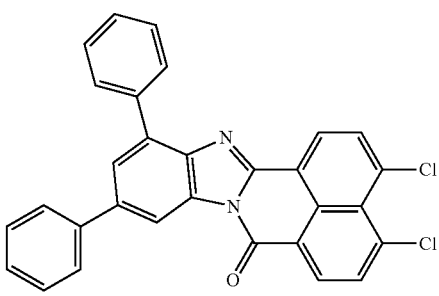 [SMILES: O=c1c2ccc(Cl)c3c(Cl)ccc(c32)c2nc3c(-c4ccccc4)cc(-c4ccccc4)cc3n12]

A mixture of 280 ml of quinoline, 18.28 g (68 mmol) of 4,5-dichloronaphthalic anhydride, 19.34 g (68 mmol) of 1,2-diamino-3,5-diphenylbenzene and 12.44 g (68 mmol) of zinc acetate was heated to 100° C. for 2 h. The reaction mixture was cooled to room temperature and filtered. The obtained residue was washed with 200 ml of methanol and 2 l of hot water followed by 120 ml of ethanol to give 20.57 g (62%) of the yellow title compound with a purity of 99% according to HPLC.

Rf (toluene)=0.66

10.2 Preparation of

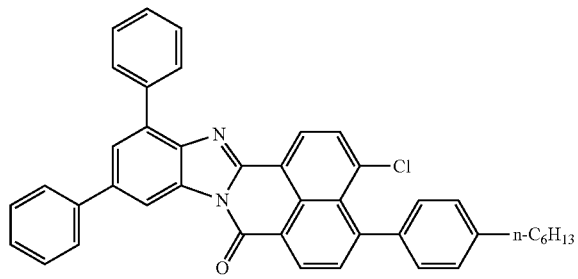

A mixture of 60 ml of toluene, 2.35 g (4.8 mmol) of the compound of example 10.1, 0.99 g (4.8 mmol) of n-hexylphenylboronic acid, a solution of 2.15 g of potassium carbonate in 15 ml of water and 6 mg of tetrakistriphenylphosphinepalladium were heated to 70° C. for 10 h. The reaction mixture was concentrated to a volume of ca. 15 ml, 80 ml of petrol ether were added and the residue was washed with 50 ml of methanol and 0.5 l of hot water to give 1.98 g (67%) of a yellow solid having a purity of 91% according to HPLC.

Rf (toluene)=0.75

10.3 Preparation of (45)

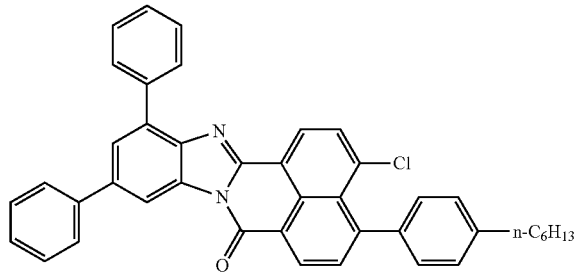

A mixture of 47 ml of DMF, 1.9 g (3.1 mmol) of the compound of example 10.2, 0.55 g (4.65 mmol) of zinc cyanide, 0.73 g of tris(dibenzylideneacetone)dipalladium and 0.48 g of 1,1'-bis(diphenylphosphinoferrocene were heated to 120° C. for 2 h. The mixture was cooled to room temperature, filtered and the residue was washed with 100 ml of DMF, 100 ml of methanol and subsequently with hot water to give 1.85 g of a yellow solid. The solid was purified on 260 g of silica gel to give 1.32 g (70%) of the title compound as yellow solid.

Rf (toluene)=0.37

$\lambda_{max}$ (PC)=548 nm; FQA=88.10%

Photostability lifetime T 80 (80 mW/cm$^2$)=53 days in polycarbonate

Example 11: Preparation of (49)

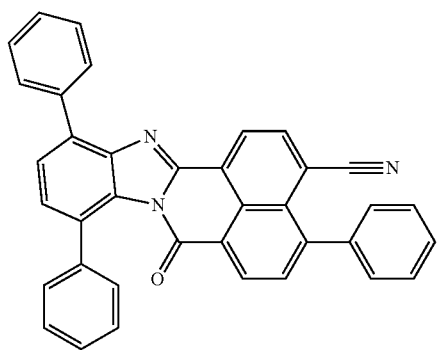

11.1 3,6-Dibromo-1,2-diamine

To a solution of 11.8 g (0.04 mol) of 4,7-dibromo-2,1,3-benzothiadiazole (prepared as described in Macromolecules 2005, 38, 244-253) in 380 ml of ethanol was added 28.0 g (0.74 mol) of sodium borohydride at 0° C. The mixture was warmed to room temperature and the solvent was evaporated. The residue was taken up in diethyl ether and water. The organic phase was separated. After evaporation of the solvent, 8.86 g (83%) of a bright yellow solid was obtained.

11.2 Preparation of

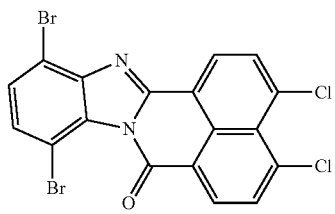 [SMILES: O=c1c2ccc(Cl)c3c(Cl)ccc(c32)c2nc3c(Br)ccc(Br)c3n12]

A mixture of 60 ml of quinoline, 3.1 g (11 mmol) of 4,5-dichlorophthalic anhydride, 3.0 g (11 mmol) of the compound of example 11.1 and 2.1 g (11 mmol) of zinc acetate was heated to 180° C. for 4 h. The mixture was cooled to room temperature and the precipitate was sucked off, washed with petrol ether and water and finally dried to give 1.64 g (29%) of the title compound.

11.3 Preparation of

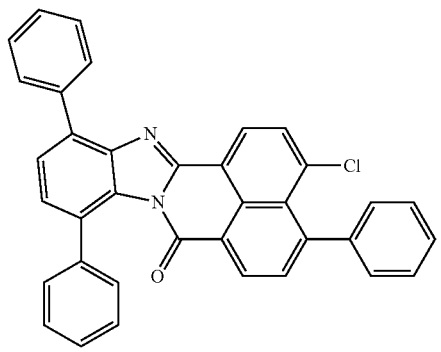 [SMILES: O=c1c2ccc(-c3ccccc3)c3c(Cl)ccc(c32)c2nc3c(-c4ccccc4)ccc(-c4ccccc4)c3n12]

A mixture of 45 ml of toluene, 1.5 g (3 mmol) of the compound of example 11.2, 1.1 g (9 mmol) of phenylboronic acid, 1.35 g (10 mmol) of potassium carbonate, 15 ml of water, 4 mg of tetrakistriphenylphosphinepalladium was heated to 90° C. for 5 hours. The mixture was cooled to room temperature, phases were separated and the organic phase was evaporated. The resulting residue was purified by column chromatography on toluene to give 479 mg (30%) of the title compound.

11.4 Preparation of (49)

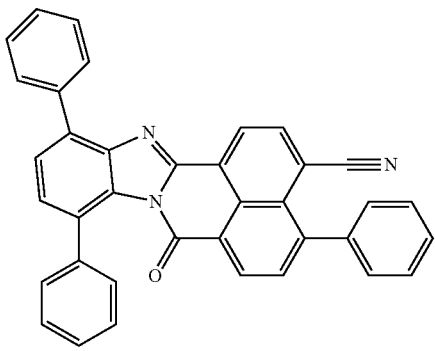

9 ml of DMF, 0.35 g (0.6 mmol) of the compound of example 11.3, 0.10 g (0.9 mmol) of zinc cyanide, 0.14 g (0.15 mmol) trisdibenzylidenacetonedipalladium and 0.095 g (0.15 mmol) of 1,1'-bis(dipehnylphosphino)ferrocene were heated to 130° C. The reaction mixture was cooled and filtered to give 0.3 g of a crude product. This material was further purified by column chromatography (toluene) to give 0.088 g (28%).

Example 12: Preparation of (50)

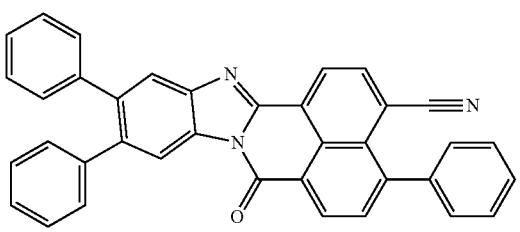

12.1 Preparation of 4-methyl-N-[2-(p-tolylsulfonylamino)phenyl]benzenesulfonamide A mixture of 1000 ml of pyridine and 416 g (2.16 mol) of 4-toluenesulfonyl chloride was cooled to −10° C. 117.4 g (1.08 mol) of 1,2-phenylenediamine were added portionwise under nitrogen and the mixture was stirred for 28 h at room temperature. Then hydrochloric acid (15%) was added, the precipitate obtained was sucked off and washed with ice water. The solid was mixed with 2800 ml of ethanol and refluxed. Then, 100 ml of methanol were added. The mixture was refluxed for a further hour and then cooled to room temperature. The precipitate formed was filtered and dried to give 390.8 g (82.5%) of the title compound having a HPLC purity (area %) of 100% (purity according to $^1$H-NMR>95%).

12.2 Preparation of N-[4,5-dibromo-2-(p-tolylsulfonylamino)phenyl]-4-methyl-benzenesulfonamide To a mixture of 75 g (0.17 mol) of the compound of 12.1, 300 ml of glacial acetic acid and 28.1 g (0.34 mol) of sodium acetate were added 61.5 g (0.77 mol) of bromine at 15° C. After completion of the addition, the mixture was heated at 110° C. for 1.5 h. The obtained suspension was poured into ice water and ethanol was added. The mixture was stirred for 1 h at 0-5° C., the precipitate obtained was filtered and washed with cold ethanol to give 86.2 g (79%) of the title compound having a HPLC purity (area) of 90%.

12.3 Preparation of 4,5-dibromobenzene-1,2-diamine

A mixture of 70 ml of sulfuric acid and 35.2 g (0.058 mol) of the compound of example 12.2 were heated to 110° C. for 15 min. The mixture was cooled to room temperature, poured onto ice water and neutralized with 50% aqueous sodium hydroxide solution. The precipitate formed was filtered, washed with 300 ml of water and dried to give 14.3 g (91%) of the title compound having a HPLC purity (area) of 97%.

12.4 Preparation of 4,5-diphenylbenzene-1,2-diamine

A mixture of 100 ml of toluene, 10 g (0.036 mol) of the compound of example 12.3, 9.65 g (0.079 mol) of phenylboronic acid, 10 g of potassium carbonate and 1.05 g of tetrakistriphenylphosphinepalladium was heated at 70° C. for 5 h. Then, the reaction mixture was mixed with water. The phases were separated to give 10.7 g of a crude product which was purified by column chromatography (toluene) to give 8.1 g (79%) of the title compound having a HPLC purity (area %) of 91.5%.

12.5 Preparation of

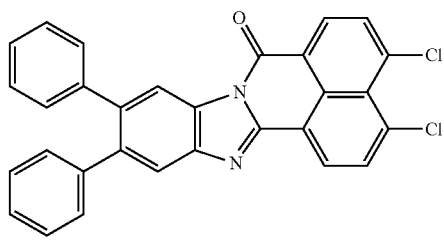 [SMILES: O=c1c2ccc(Cl)c3c(Cl)ccc(c32)c2nc3cc(-c4ccccc4)c(-c4ccccc4)cc3n12]

A mixture of 160 ml of quinoline, 10.2 g (0.036 mol) of the compound of example 12.4, 9.6 g (0.036 mol) of 4,5-dichloronaphthalic anhydride and 6.6 g (0.036 mol) of zinc acetate was heated to 100° C. for 8 h. Subsequently, the reaction mixture was cooled to room temperature and the precipitate was filtered. The precipitate was washed with 150 ml of methanol, 900 ml of hot water and 90 ml of ethanol to give 12.8 g of the crude title compound which was stirred with 50 ml of methanol. The solid was filtered and washed with ethanol and methanol to give 2.5 g (71%) of the title compound with a HPLC purity (area %) of 97%.

12.6 Preparation of

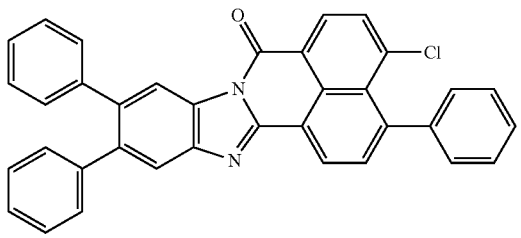 [SMILES: O=c1c2ccc(Cl)c3c(-c4ccccc4)ccc(c32)c2nc3cc(-c4ccccc4)c(-c4ccccc4)cc3n12]

A mixture of 50 ml of THF, 1.5 g (0.003 mol) of the compound of example 12.5, 0.36 g (0.003 mol) of phenylboronic acid, 1.3 g of potassium carbonate and 0.34 g of tetrakistriphenylphosphinepalladium was heated to 70° C. for 8 h. The solvent was evaporated under reduced pressure. The residue was taken up in toluene and extracted with water. The organic phase was concentrated and the crude product was stirred with methanol to give 1.1 g (62.5%) of the title compound having a HPLC purity (area %) of 90%.

12.7 Preparation of the Compound of (50)

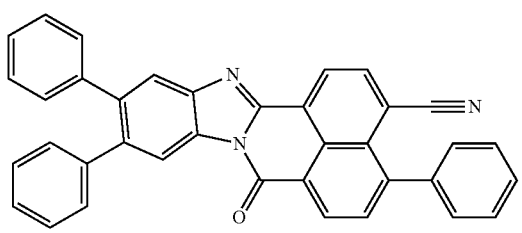

18 ml of DMF, 0.7 g (1.2 mmol) of the compound of example 12.6, 0.21 g (1.8 mmol) of zinc cyanide, 0.28 g (0.3 mmol) of tris(dibenzylidenacetone)dipalladium and 0.19 g (0.3 mmol) of 1,1'-bis(diphenylphosphino)ferrocene were heated to 120° C. for 12 h. The mixture was cooled and filtered to give 0.6 g of the crude title compound, which was purified by column chromatography using toluene to give 0.35 g (56%) of the title compound having a HPLC purity (area %) of 99.6%.

Example 13: Preparation of (25)

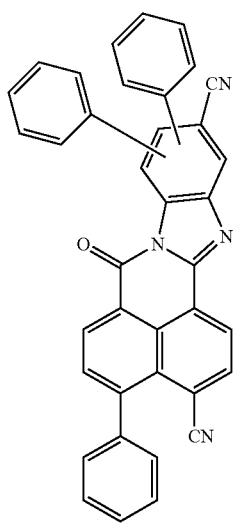

(26)

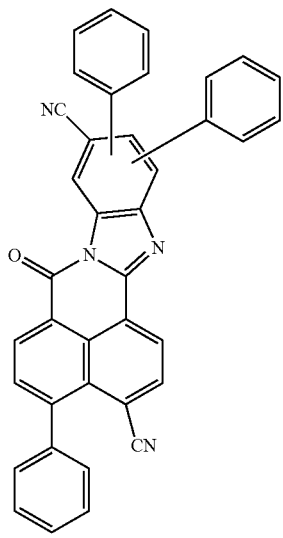

(51)

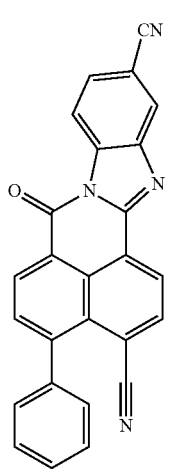

(52)

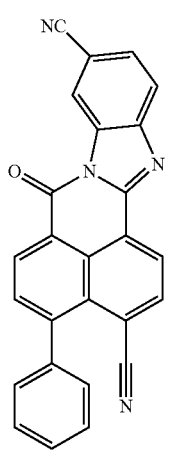

(53)

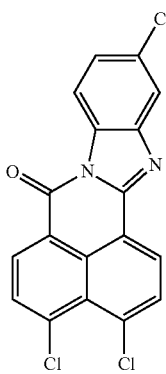

A mixture of 60 ml of quinoline, 5.38 g (0.02 mol) of 4,5-dichloronaphthalic anhydride, 2.7 g (0.025 mol) of 3,4 diaminobenzonitrile and 3.66 g of zinc acetate was heated to 145° C. for 2 hours. The reaction mixture was diluted with a small amount of methanol, filtered, washed with water and dried to give 6.37 g (88%) of the title compounds as yellow mixtures.

Rf (toluene: ethyl acetate 10:1)=0.33, 0.44

13.2 Preparation of

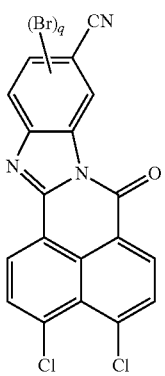

where q is 1 or 2

A mixture of 240 ml of water, 3.64 g (0.01 mol) of the compounds of 13.1, 3.2 g of bromine (0.04 mol) was refluxed for 3 hours. Then, further 9.6 g (0.12 mol) of bromine were added and the mixture was refluxed overnight. Subsequently, the bromine was blown out with nitrogen to give 4.64 g (89%) of a yellow product which was separated by column chromatography using toluene to give a fraction having a Rf 0.65 which were 1.57 g of the title compounds.

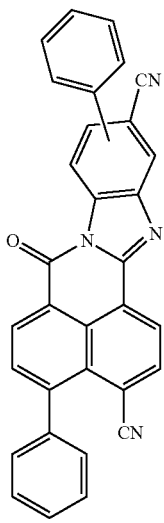

(54)

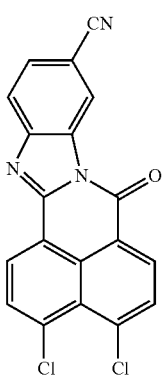

13.1 Preparation of 13.3 Preparation of

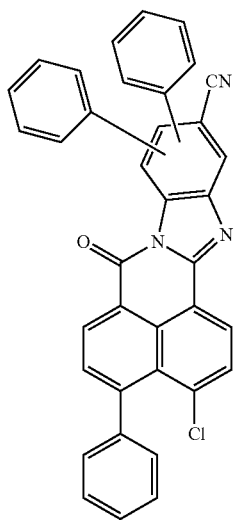

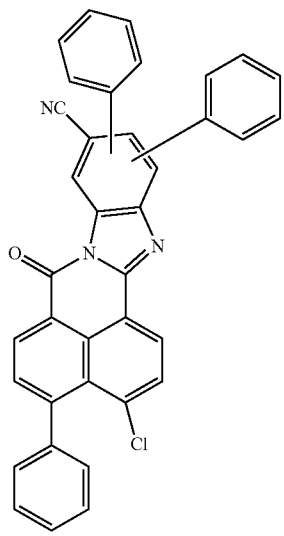

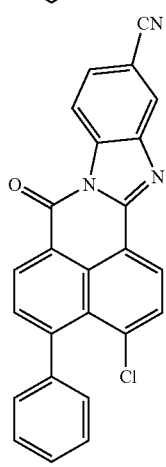

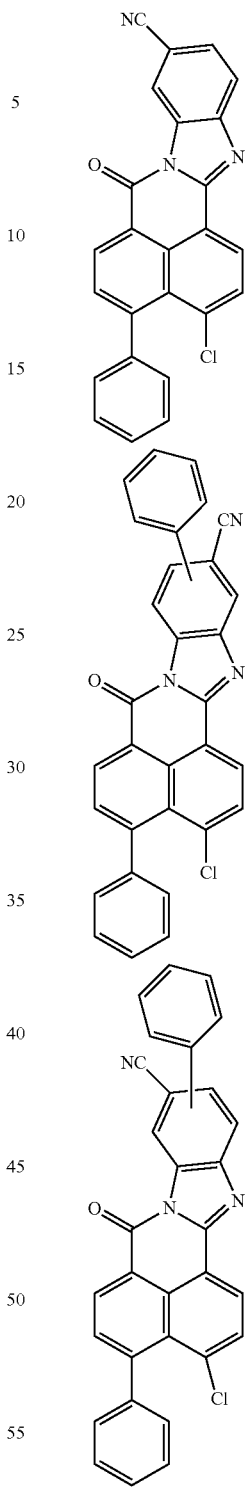

A mixture of 30 ml of toluene, 1.0 g (2 mmol) of the compounds of example 13.2, 0.24 g (2 mmol) of phenylboronic acid, 0.9 g of potassium carbonate and 2.4 mg of tetrakistriphenylphosphinepalladium were heated to 60° C. for 2 hours. Further 9.6 mg of tetrakistriphenylphosphinepalladium and further 0.24 g (2 mmol) of phenylboronic acid were added and the mixture was heated to 85° C. for 6 hours and to 100° C. for 2 days. After cooling to room temperature, the title compounds were precipitated with petrol ether, filtered and washed with water to give 0.98 g of a crude product, which was purified by chromatography using toluene. The fraction having Rf (toluene:ethyl acetate=10:1)=0.75 was concentrated to give 0.32 g (33%) of the title compounds.

13.4 Preparation of Compounds (25), (26), (51), (52), (53) and (54)

A mixture of 20 ml of DMF, 0.3 g (0.6 mmol) of the compounds of example 13.3, 0.11 g (0.9 mmol) of zinc cyanide, 0.066 g zinc, 0.16 g of tris(dibenzylideneacetone)-dipalladium), 89 mg of 1,1'-bis(diphenylphosphino)ferrocene was stirred for 2 hours at 60° C. Further 110 mg of zinc cyanide were added and the mixture was stirred overnight at 60° C. The title compounds were precipitated by addition of water and purified by chromatography using toluene to give 70 mg of the title compounds.
Rf (toluene)=0.5).

Example 14: Application Example of Color Converter Devices

In order to show applicability of the inventive cyanated naphthalenebenzimidazole compounds, compound (11) was used for building several color converters.

Inventive color converter, which convert blue LED light into white light with different color temperatures (correlated color temperature CCT), consist of polymer foils consisting of polycarbonate, which contain the novel yellow fluorescent compound 11 and the known red fluorescent dye N,N'-bis(2,6-diisopropylphenyl)-1,6,7,12-tetraphenoxyperylene-3,4;9,10-tetracarboxylic acid diimide (DPI) and the scattering agent $TiO_2$ (Kronos 2233).

14.0 g of polycarbonate Makrolon 2808, (Bayer) was used together with 6-8 mg of the inventive yellow fluorescent compound (11) from example 3.3 (according to CCT) and 0.3 to 1 mg (according to CCT) of the red fluorescent dye DPI and 112 mg of $TiO_2$. To this mixture, 36.4 ml of dichlormethane were added and stirred in a sealed vessel for 16 hours. The resulting dispersion was then doctor bladed onto a glass plate using a doctor blade (Vierfach-Filmziehrahmen, Erichsen, Modell 360, slit height of 800 µm). The wet films were dried under air for one hour, then detached from the glass and dried under vacuum at 50° C. for at least three hours. Polycarbonate foils with thicknesses of ca 135 µm are resulting from this process. From these films test specimens with a diameter auf 23 and 61.5 mm were made by stamping.

For the comparative examples the yellow compound from example 7 and the red fluorescent dye DPI instead of the inventive compound (11) and the red fluorescent dye DPI were used.

Characterization:

Quantum efficiencies of fluorescence were measured using the absolute quantum-efficiency measurement system (Fa. Hamamatsu, Model C9920-02) and the quantum efficiencies refer to complete fluorescence (yellow and red fluorescence) upon excitation at 450 nm.

Applicability as color converters was tested using the 61.5 mm test specimen by shining light of a series of blue LEDs (450 nm) from below. These LEDs were placed in a highly reflecting mixing chamber. The white light emitted from the top of the converter was measured with an 50 cm integrating sphere (Modell ISP 500, Instrument Systems) equipped with a spectral radiometer (CAS 140 CT-156, Instrument Systems, München). Coloristic data (color point CIE-x, CIE-y, CCT, deviation from Planck curve duv, color rendition index CRI) were calculated from the emitted spectra. Energy conversion efficiency was calculated from the ratio of the energy integral of the white light (measured with the color converter) and the energy integral of the blue LEDs (measured without color converter). Table 1 shows the composition of the color converter. The results are summarized in table 2 below.

TABLE 1

| Sample | Yellow Fluorescent compound | % yellow fluorescent dye [% by wt.][#] | % DPI [% by wt.][#] | $TiO_2$ [% by wt][#] | average thickness of foil (µm) |
|---|---|---|---|---|---|
| V1 | compound (11) | 0.0949% | 0.0048% | 0.80% | 140.3 |
| V2 | compound (11) | 0.0871% | 0.0044% | 0.80% | 133.7 |
| V3 | compound (11) | 0.0682% | 0.0034% | 0.80% | 136.8 |
| V4 | compound (11) | 0.0599% | 0.0030% | 0.80% | 134.2 |
| V5 | compound (11) | 0.0550% | 0.0028% | 0.80% | 132.9 |
| V6 | compound (11) | 0.0579% | 0.0029% | 0.80% | 134.3 |
| C1 | compound from example 7 | 0.1446% | 0.0099% | 0.80% | 142 |
| C2 | compound from example 7 | 0.1392% | 0.0097% | 0.80% | 132 |
| C3 | compound from example 7 | 0.1178% | 0.0081% | 0.80% | 139 |
| C4 | compound from example 7 | 0.1000% | 0.0068% | 0.80% | 141 |
| C5 | compound from example 7 | 0.1065% | 0.0075% | 0.80% | 134 |
| C6 | compound from example 7 | 0.1029% | 0.0072% | 0.80% | 132 |
| C7 | compound from example 7 | 0.1047% | 0.0064% | 0.80% | 133 |
| C8 | compound from example 7 | 0.0858% | 0.0058% | 0.80% | 142 |
| C9 | compound from example 7 | 0.0900% | 0.0056% | 0.80% | 133 |

[#]based on polycarbonate

TABLE 2

| Sample | CIE-x | CIE-y | CCT (K) | Planck deviation duv | CRI | Conversion efficiency (energy) | Luminous efficiency (Lumen/Watt) | Fluorescence Quantum yield (%) |
|---|---|---|---|---|---|---|---|---|
| V1 | 0.4367 | 0.4116 | 3064 | 3.01E−03 | 76.88 | 59.10% | 195.92 | 87.9 |
| V2 | 0.4174 | 0.3913 | 3252 | −2.17E−03 | 77.97 | 60.41% | 196.10 | 87.6 |
| V3 | 0.4013 | 0.3887 | 3573 | −2.37E−06 | 76.93 | 60.88% | 200.16 | 88.0 |
| V4 | 0.3899 | 0.3791 | 3770 | −1.51E−03 | 76.01 | 62.81% | 206.55 | 87.6 |
| V5 | 0.3695 | 0.3593 | 4190 | −5.05E−03 | 77.40 | 62.40% | 199.68 | 87.2 |
| V6 | 0.3619 | 0.3505 | 4380 | −6.94E−03 | 78.98 | 64.43% | 202.18 | 87.8 |
| C1 | 0.4457 | 0.4192 | 2978 | 4.73E−03 | 93.20 | 55.07% | 165.18 | 85.1 |
| C2 | 0.4263 | 0.3977 | 3134 | −9.95E−04 | 92.55 | 55.76% | 163.78 | 84.7 |
| C3 | 0.4197 | 0.4017 | 3293 | 1.80E−03 | 94.93 | 57.79% | 176.81 | 84.7 |
| C4 | 0.3999 | 0.3965 | 3665 | 3.75E−03 | 95.35 | 57.60% | 176.76 | 85.2 |
| C5 | 0.3901 | 0.3788 | 3762 | −1.72E−03 | 94.66 | 57.77% | 171.80 | 84.6 |
| C6 | 0.3804 | 0.3693 | 3945 | −3.49E−03 | 94.73 | 59.78% | 178.17 | 84.7 |
| C7 | 0.3780 | 0.3773 | 4072 | 9.92E−04 | 94.79 | 59.92% | 182.58 | 85.4 |
| C8 | 0.3702 | 0.3782 | 4298 | 3.81E−03 | 94.34 | 58.94% | 180.81 | 84.9 |
| C9 | 0.3664 | 0.3723 | 4375 | 2.27E−03 | 93.66 | 60.39% | 185.11 | 85.0 |

FIG. 1 shows that the inventive compound (11) and the comparative example 7 can be used to produce color converting foils, which convert blue LED light into high quality white light for a wide range of color temperatures close to the Planck curve and with high CRI. However, converters containing the inventive compound 11 show higher conversion efficiencies compared to converters containing the dye 7 (comparative example).

The invention claimed is:

1. A cyanated naphthalenebenzimidazole compound of the formula I

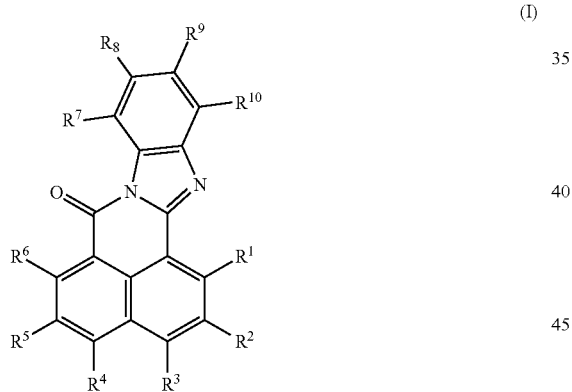

(I)

or mixture of these,
in which
$R^1$, $R^2$, $R^3$, $R^4$, $R^5$, $R^6$, $R^7$, $R^8$, $R^9$ and $R^{10}$ are each independently hydrogen, cyano or aryl which is unsubstituted or has one or more identical or different substituents $R^{Ar}$, where
each $R^{Ar}$ is independently selected from the group consisting of cyano, hydroxyl, mercapto, halogen, $C_1$-$C_{20}$-alkoxy, $C_1$-$C_{20}$-alkylthio, nitro, —$NR^{Ar2}R^{Ar3}$, —$NR^{Ar2}COR^{Ar3}$, —$CONR^{Ar2}R^{Ar3}$, $SO_2NR^{Ar2}R^{Ar3}$, —$COOR^{Ar2}$, —$SO_3R^{Ar2}$,
$C_1$-$C_{30}$-alkyl, $C_2$-$C_{30}$-alkenyl, $C_2$-$C_{30}$-alkynyl, where the three latter radicals are unsubstituted or bear one or more $R^a$ groups,
$C_3$-$C_8$-cycloalkyl, 3- to 8-membered heterocyclyl, where the two latter radicals are unsubstituted or bear one or more $R^b$ groups,
aryl, U-aryl, heteroaryl and U-heteroaryl, where the four latter radicals are unsubstituted or bear one or more $R^b$ groups, where
each $R^a$ is independently selected from the group consisting of cyano, hydroxyl, oxo, mercapto, halogen, $C_1$-$C_{20}$-alkoxy, $C_1$-$C_{20}$-alkylthio, nitro, —$NR^{Ar2}R^{Ar3}$, —$NR^{Ar2}COR^{Ar3}$, —$CONR^{Ar2}R^{Ar3}$, —$SO_2NR^{Ar2}R^{Ar3}$, —$COOR^{Ar2}$, —$SO_3R^{Ar2}$, $C_3$-$C_8$-cycloalkyl, 3- to 8-membered heterocyclyl, aryl and heteroaryl, where the cycloalkyl, heterocyclyl, aryl and heteroaryl radicals are unsubstituted or bear one or more $R^b$ groups;
each $R^b$ is independently selected from the group consisting of cyano, hydroxyl, oxo, mercapto, halogen, $C_1$-$C_{20}$-alkoxy, $C_1$-$C_{20}$-alkylthio, nitro, —$NR^{Ar2}R^{Ar3}$, —$NR^{Ar2}COR^{Ar3}$, —$CONR^{Ar2}R^{Ar3}$, —$SO_2NR^{Ar2}R^{Ar3}$, —$COOR^{Ar2}$, —$SO_3R^{Ar2}$, $C_1$-$C_{18}$-alkyl, $C_2$-$C_{18}$-alkenyl, $C_2$-$C_{18}$-alkynyl, $C_3$-$C_8$-cycloalkyl, 3- to 8-membered heterocyclyl, aryl and heteroaryl, where the four latter radicals are unsubstituted or bear one or more $R^{b1}$ groups,
each $R^{b1}$ is independently selected from the group consisting of cyano, hydroxyl, mercapto, oxo, nitro, halogen, —$NR^{Ar2}R^{Ar3}$, —$NR^{Ar2}COR^{Ar3}$, —$CONR^{Ar2}R^{Ar3}$, —$SO_2NR^{Ar2}R^{Ar3}$, —$COOR^{Ar2}$, —$SO_3R^{Ar2}$, —$SO_3R^{Ar2}$, $C_1$-$C_{18}$-alkyl, $C_2$-$C_{18}$-alkenyl, $C_2$-$C_{18}$-alkynyl, $C_1$-$C_{12}$-alkoxy, $C_1$-$C_{12}$-alkylthio,
U is an —O—, —S—, —$NR^{Ar1}$—, —CO—, —SO— or —$SO_2$— moiety;
$R^{Ar1}$, $R^{Ar2}$, $R^{Ar3}$ are each independently hydrogen, $C_1$-$C_{15}$-alkyl, 3- to 8-membered cycloalkyl, 3- to 8-membered heterocyclyl, aryl or heteroaryl, where alkyl is unsubstituted or bears one or more $R^a$ groups, where 3- to 8-membered cycloalkyl, 3- to 8-membered heterocyclyl, aryl and heteroaryl are unsubstituted or bear one or more $R^b$ groups;
with the proviso that one, two or three of the radicals $R^1$, $R^2$, $R^3$, $R^4$, $R^5$, $R^6$, $R^7$, $R^8$, $R^9$ or $R^{10}$ are cyano and 1, 2, 3, 4, 5, 6 or 7 of the $R^1$, $R^2$, $R^3$, $R^4$, $R^5$, $R^6$, $R^7$, $R^8$, $R^9$ and $R^{10}$ radicals is/are aryl which is unsubstituted or has one or more identical or different substituents $R^{Ar}$.

2. The cyanated naphthalenebenzimidazole compound or a mixture of these according to claim 1, in which each $R^{Ar}$ is independently cyano, $C_1$-$C_{12}$-alkoxy, hydroxyl, halogen, nitro, —$NR^{Ar2}R^{Ar3}$, $NR^{Ar2}COR^{Ar3}$, —$CONR^{Ar2}R^{Ar3}$, —$SO_2NR^{Ar2}R^{Ar3}$, —$COOR^{Ar2}$, —$SO_3R^{Ar2}$, $C_1$-$C_{18}$-alkyl which is unsubstituted or mono- or polysubstituted by hydroxyl, halogen, cyano, nitro or —$NR^{Ar2}R^{Ar3}$, or $C_3$-$C_8$- cycloalkyl or phenyl, where the two latter radicals are in turn unsubstituted or mono- or polysubstituted by $C_1$-$C_{18}$-alkyl, $C_1$-$C_{12}$-alkoxy or cyano.

3. The cyanated naphthalenebenzimidazole compound or a mixture of these according to claim 1, in which at least one of the $R^1$, $R^2$, $R^3$, $R^4$, $R^5$, $R^6$, $R^7$, $R^8$, $R^9$ and $R^{10}$ radicals is phenyl which is unsubstituted or has one or more identical or different $R^{Ar}$ radicals.

4. The cyanated naphthalenebenzimidazole compound or a mixture of these according to claim 3, in which at least one of the $R^1$, $R^2$, $R^3$, $R^4$, $R^5$, $R^6$, $R^7$, $R^8$, $R^9$ and $R^{10}$ radicals is phenyl which is unsubstituted or bears a cyano group.

5. The cyanated naphthalenebenzimidazole compound or a mixture of these according to claim 3, in which at least one of the $R^1$, $R^2$, $R^3$, $R^4$, $R^5$, $R^6$, $R^7$, $R^8$, $R^9$ and $R^{10}$ radicals is phenyl, which is unsubstituted or carries 1, 2 or 3 substituents selected from $C_1$-$C_{10}$-alkyl.

6. The cyanated naphthalenebenzimidazole compound or a mixture of these according to claim 1, in which one or two of the $R^1$, $R^2$, $R^3$, $R^4$, $R^5$, $R^6$, $R^7$, $R^8$, $R^9$ and $R^{10}$ radicals is/are cyano.

7. The cyanated naphthalenebenzimidazole compound or a mixture of these according to claim 1, in which
one or two of the $R^1$, $R^2$, $R^3$, $R^4$, $R^5$, $R^6$ radicals is/are phenyl, 4-cyanophenyl or phenyl which carries 1, 2 or 3 substituents selected from $C_1$-$C_{10}$-alkyl and the other $R^1$, $R^2$, $R^3$, $R^4$, $R^5$, $R^6$ radicals are hydrogen; and
zero, one or two of the $R^7$, $R^8$, $R^9$ and $R^{10}$ radicals is/are phenyl, 4-cyanophenyl or phenyl which carries 1, 2 or 3 substituents selected from $C_1$-$C_{10}$-alkyl and the other $R^7$, $R^8$, $R^9$ and $R^{10}$ radicals are hydrogen or cyano.

8. The cyanated naphthalenebenzimidazole compound according to claim 1, in which one or two of the $R^1$, $R^2$, $R^3$, $R^4$, $R^5$, $R^6$ radicals is/are phenyl, 4-cyanophenyl, cyano or phenyl which carries 1, 2 or 3 substituents selected from $C_1$-$C_{10}$-alkyl and the other $R^1$, $R^2$, $R^3$, $R^4$, $R^5$, $R^6$ radicals are hydrogen; and
zero, one, two or three of the $R^7$, $R^8$, $R^9$ and $R^{10}$ radicals is/are phenyl, 4-cyanophenyl or phenyl which carries 1, 2 or 3 substituents selected from $C_1$-$C_{10}$-alkyl and the other $R^7$, $R^8$, $R^9$ and $R^{10}$ radicals are hydrogen or cyano.

9. The cyanated naphthalenebenzimidazole compound or a mixture of these according to claim 1, wherein the cyanated napthalenebenzimidazole compound corresponds to the formula I-A

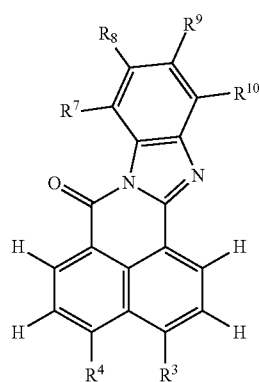

(I-A)

or a mixture of these
in which
$R^3$ and $R^4$ are each independently cyano, phenyl, 4-cyanophenyl or phenyl which carries 1, 2 or 3 substituents selected from $C_1$-$C_{10}$-alkyl; and $R^7$, $R^8$, $R^9$ and $R^{10}$ are each independently hydrogen, cyano, phenyl, 4-cyanophenyl or phenyl which carries 1, 2 or 3 substituents selected from $C_1$-$C_{10}$-alkyl.

10. The cyanated naphthalenebenzimidazole compound according to claim 9,
wherein the cyanated napthalenebenzimidazole compound corresponds to the formula I-Aa

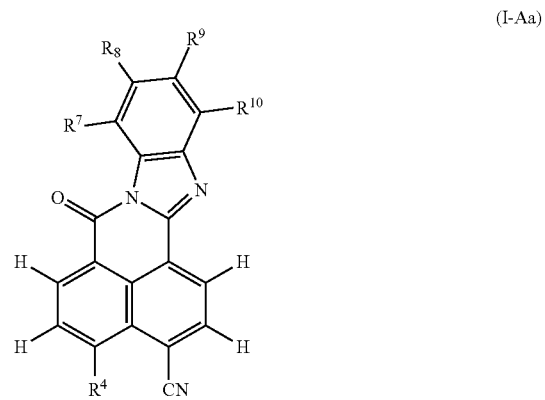

(I-Aa)

in which
$R^4$ is phenyl, 4-cyanophenyl or phenyl which carries 1, 2 or 3 substituents selected from $C_1$-$C_{10}$-alkyl; and
two of the radicals $R^7$, $R^8$, $R^9$ and $R^{10}$ are each independently, phenyl, 4-cyanophenyl or phenyl which carries 1, 2 or 3 substituents selected from $C_1$-$C_{10}$-alkyl and the other radicals $R^7$, $R^8$, $R^9$ and $R^{10}$ are hydrogen.

11. A mixture of cyanated naphthalenebenzimidazole compounds according to claim 9, wherein the cyanated naphthalenebenzimidazole compounds correspond to the formula I-Ab and I-Ab'

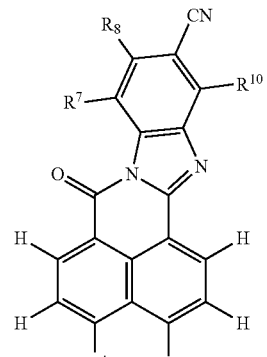

(I-Ab)

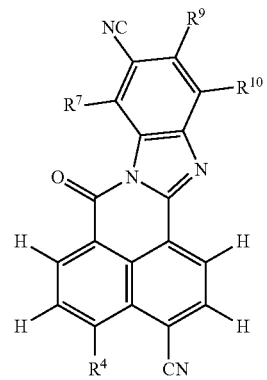

(I-Ab')

in which

R⁴ is phenyl, 4-cyanophenyl or phenyl which carries 1, 2 or 3 substituents selected from $C_1$-$C_{10}$-alkyl; and zero, one or two of the radicals $R^7$, $R^{10}$, $R^8$ and $R^9$, if present, are each independently, phenyl, 4-cyanophenyl or phenyl which carries 1, 2 or 3 substituents selected from $C_1$-$C_{10}$-alkyl and the other radicals $R^7$, $R^{10}$, $R^8$, $R^9$, if present, are hydrogen.

12. A cyanated naphthalenebenzimidazole compound of the formula I

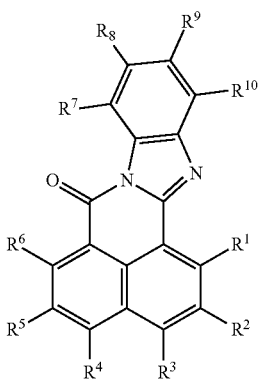

or a mixture of these, where $R^1$, $R^2$, $R^3$, $R^4$, $R^5$, $R^6$, $R^7$, $R^8$, $R^9$ and $R^{10}$ are as defined as in claim 1 obtained by a process comprising 1.1) reacting 1,8-naphthalic anhydride with a diamine of the formula (i)

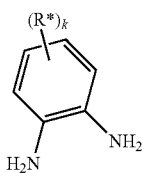

where each R* is independently cyano or aryl which is unsubstituted or has one or more identical or different substituents $R^{Ar}$, where $R^{Arr}$ is as defined above;

k is 0, 1 or 2, to obtain a compound of the formula (ii)

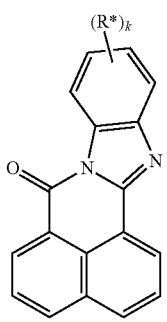

1.2) subjecting the compound of the formula (ii) obtained in step 1.1) to a bromination to obtain a compound of the formula (iii)

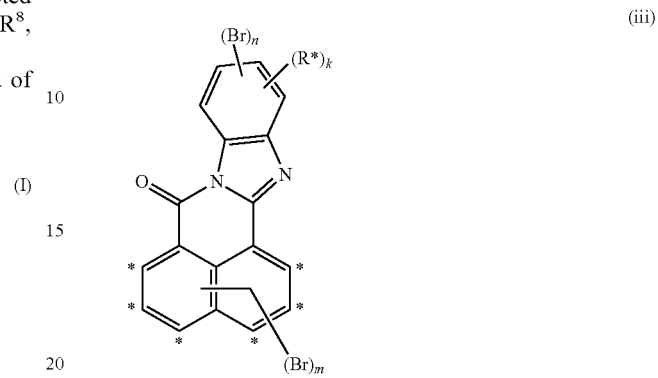

in which n is 1 or 2;

m is 1 or 2, where $(Br)_m$ radicals are at one or more of the positions indicated by *;

1.3) subjecting the compound of the formula (iii) obtained in step 1.2) to a substitution of bromine to aryl which is unsubstituted or has one or more identical or different substituents $R^{Ar}$, where $R^{Ar}$ is as defined in claim 1 by cross-coupling with an organometallic compound of the formula iv Ar-Met (iv)

in which

Ar is aryl which is mono- or polysubstituted by $R^{Ar}$; and

Met is $B(OH)_2$, $B(OR')(OR'')$, Zn—R''' or $Sn(R^*)_3$, in which

R' and R'' are each independently hydrogen, $C_1$-$C_{30}$-alkyl, $C_5$-$C_8$-cycloalkyl, $C_6$-$C_{14}$-aryl or heteroaryl, or R' and R'' together are $C_2$-$C_4$-alkylene which optionally bears 1, 2, 3, 4, 5, 6, 7 or 8 substituents selected from $C_1$-$C_4$-alkyl, $C_5$-$C_8$-cycloalkyl, $C_6$-$C_{14}$-aryl and heteroaryl, R''' is $C_1$-$C_8$-alkyl or phenyl and R* is $C_1$-$C_8$-alkyl or phenyl, in the presence of a transition metal catalyst to obtain the compound of the formula I

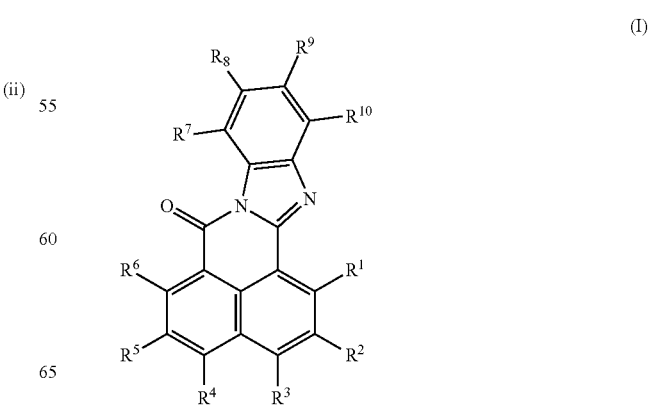

where 1 or 2 of the radicals $R^1$, $R^2$, $R^3$, $R^4$, $R^5$ or $R^6$ are aryl, which is unsubstituted or has one or more identical or different substituents $R^{Ar}$, and the other radicals $R^1$, $R^2$, $R^3$, $R^4$, $R^5$ or $R^6$ are hydrogen and one or two of the radicals $R^7$, $R^8$, $R^9$ or $R^{10}$ are aryl, which is unsubstituted or has one or more identical or different substituents $R^{Ar}$, and the other radicals $R^7$, $R^8$, $R^9$ or $R^{10}$ are hydrogen, cyano or aryl which is unsubstituted or has one or more identical or different substituents $R^{Ar}$ 1.4) optionally subjecting the compound(s) obtained in step 1.3) to at least one separation and/or purification step;

or 2.1) reacting 1,8-dihalonaphthalic anhydride of the formula (v)

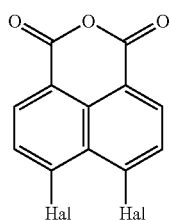

(v)

where Hal is chlorine or bromine
with a diamine of the formula (i)

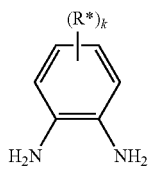

(i)

where
each R* is independently cyano or aryl which is unsubstituted or has one or more identical or different substituents $R^{Ar}$, where $R^{Ar}$ is as defined above;
k is 0, 1 or 2,
to obtain a compound of the formula (vi)

(vi)

2.2) subjecting the compound of the formula (vi) obtained in step 2.1) to a bromination to obtain a compound of the formula (vii)

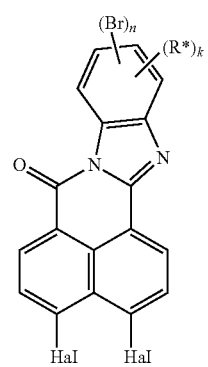

(vii)

in which
n is 1 or 2;

2.3) subjecting the compound of the formula (vii) obtained in step 2.2) to a substitution reaction, wherein each Hal and each bromine atom is substituted by aryl which is unsubstituted or has one or more identical or different substituents $R^{Ar}$, where $R^{Ar}$ is as defined in claim 1, or subjecting the compounds of the formula (vii) obtained in step 2.2) to a substitution reaction, wherein each Hal is substituted by aryl, and a part of the bromine atoms attached to the benzene ring of the benzimidazole moiety are substituted by aryl and the other bromine atoms that are not substituted by aryl, are substituted by hydrogen, where aryl is unsubstituted or has one or more identical or different substituents $R^{Ar}$, where $R^{Ar}$ is as defined in claim 1
by cross-coupling with an organometallic compound of the formula iv Ar-Met            (iv)

in which Ar and Met are as defined above
in the presence of a transition metal catalyst to obtain the compound of the formula I (I)

where
$R^3$ and $R^4$ are aryl, which is unsubstituted or has one or more identical or different substituents $R^{Ar}$,
zero, one or two of the radicals $R^7$, $R^8$, $R^9$ or $R^{10}$ are aryl, which is unsubstituted or has one or more identical or different substituents $R^{Ar}$, and the other radicals $R^7$, $R^8$, $R^9$ or $R^{10}$ are hydrogen, cyano or aryl which is unsubstituted or has one or more identical or different substituents $R^{Ar}$, 2.4) optionally subjecting the compound(s) obtained in step 2.3) to at least one separation and/or purification step;

or 3.1 a) subjecting the compound of the formula (vii) obtained in step 2.2), wherein each Hal is chlorine, to a substitution reaction, where one of the Hal is substituted by aryl, and all or a part of the bromine atoms attached to the benzene ring of the benzimidazole moiety are substituted by aryl and the other bromine atoms that are not substituted by aryl, are substituted by hydrogen, where aryl is unsubstituted or has one or more identical or different substituents $R^{Ar}$, where $R^{Ar}$ is as defined above by cross-coupling with an organometallic compound of the formula IV Ar-Met     (IV)

in which Ar and Met are as defined above
in the presence of a transition metal catalyst to obtain the compound of the formula (viiia) and (viiib)

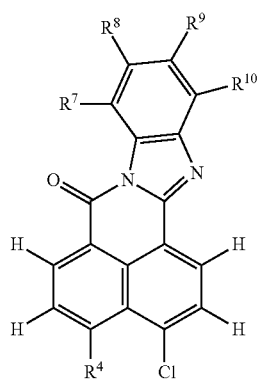

(viiia)

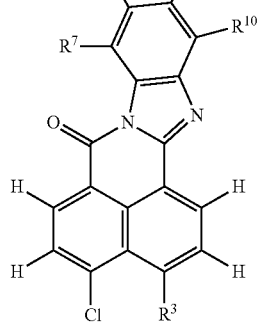

(viiib)

where
$R^3$, if present, is aryl, which is unsubstituted or has one or more identical or different substituents $R^{Ar}$;
$R^4$, if present, is aryl, which is unsubstituted or has one or more identical or different substituents $R^{Ar}$;
zero, one or two of the radicals $R^7$, $R^8$, $R^9$ or $R^{10}$ are aryl, which is unsubstituted or has one or more identical or different substituents $R^{Ar}$, and the other radicals $R^7$, $R^8$, $R^9$ or $R^{10}$ are hydrogen, cyano or aryl which is unsubstituted or has one or more identical or different substituents $R^{Ar}$ 3.2a) optionally subjecting the compounds of formulae (viiia) and (viiib) to at least one purification and/or separation step;

3.3a) reacting the compound(s) obtained in step 3.1) or 3.2) with a metal cyanide to obtain compound(s) of the formula I,

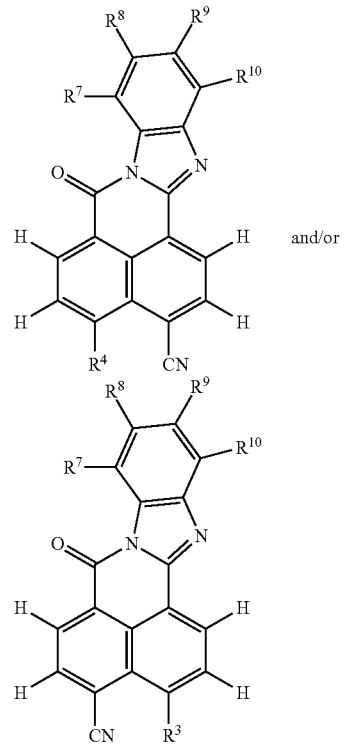

and/or where
$R^3$, if present, is aryl which is unsubstituted or mono- or polysubstituted by $R^{Ar}$;
$R^4$, if present, is aryl which is unsubstituted or mono- or polysubstituted by $R^{Ar}$;
one or two of the radicals $R^7$, $R^8$, $R^9$ or $R^{10}$ are aryl, which is unsubstituted or has one or more identical or different substituents $R^{Ar}$, and the other radicals $R^7$, $R^8$, $R^9$ or $R^{10}$ are hydrogen, cyano or aryl which is unsubstituted or has one or more identical or different substituents $R^{Ar}$ 3.4a) optionally subjecting the compound(s) obtained in step 3.3a) to at least one separation and/or purification step;

or 3.1b1) reacting the compounds of the formula (vi), obtained in step 2.1 with a metal cyanide to obtain compounds of the formulae (ixa) and (ixb)

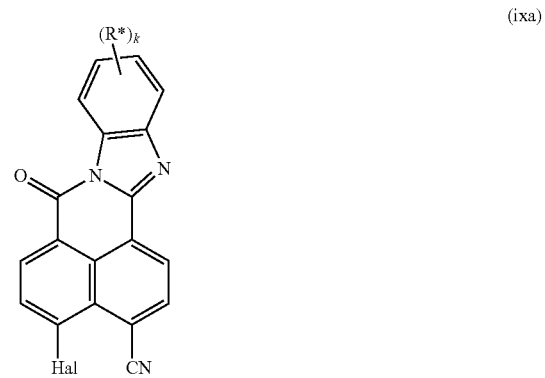

(ixa)

-continued

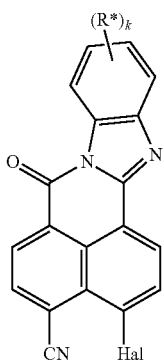
(ixb)

where (R*)$_k$ is as defined above;
3.1b2) subjecting the compounds of the formula (ixa) and (ixb) obtained in step 3.1b1) to a cross-coupling with an organometallic compound of the formula iv Ar-Met (iv)

where Ar and Met are as defined above,
in the presence of a transition metal catalyst to give compounds of the formula I

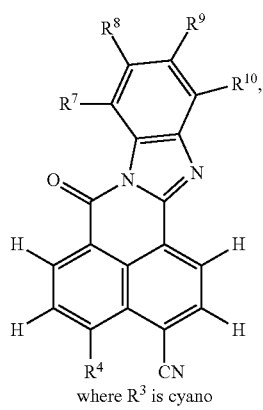
(I)

where R$^3$ is cyano

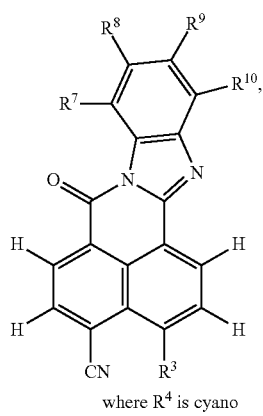
(I)

where R$^4$ is cyano where
R$^3$, if present, is aryl which is unsubstituted or mono- or polysubstituted by R$^{Ar}$;
R$^4$, if present, is aryl which is unsubstituted or mono- or polysubstituted by R$^{Ar}$;
zero, one or two of the radicals R$^7$, R$^8$, R$^9$ or R$^{10}$ are cyano or aryl which is unsubstituted or has one or more identical or different substituents R$^{Ar}$ and the remaining radicals R$^7$, R$^8$, R$^9$ or R$^{10}$ are hydrogen;
3.1b3) optionally subjecting the compound(s) of formula I to at least one separation and/or purification step;
or
3.2b1) first reacting the compound of the formula (vi) obtained in step 2.1) with a compound of the formula (IV)

Ar-Met (iv)

where Ar and Met are as defined above,
in the presence of a transition metal catalyst to give a compound of the formula (xa) and (xb)

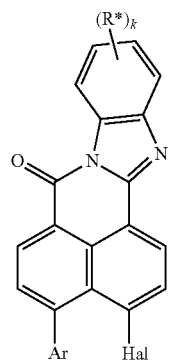
(xa)

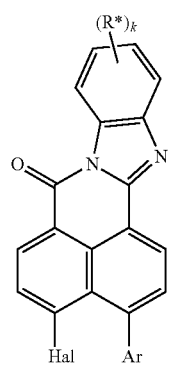
(xb)

with a metal cyanide to obtain compounds of the formulae and then treated with a metal cyanide
3.2b2) reacting the compounds of the formulae (xa) and (xb) obtained in step 3.2b1) with a metal cyanide to obtain compounds of the formulae;

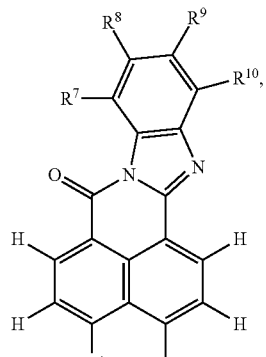
(I)

where R3 is cyano

-continued

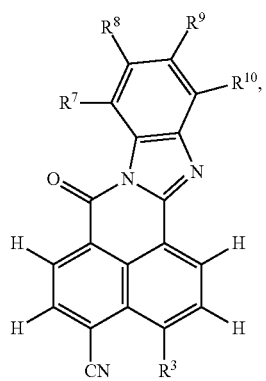

(I)

where R⁴ is cyano where

R³, if present, is aryl which is unsubstituted or mono- or polysubstituted by $R^{Ar}$;

R⁴, if present, is aryl which is unsubstituted or mono- or polysubstituted by $R^{Ar}$;

zero, one or two of the radicals $R^7$, $R^8$, $R^9$ or $R^{10}$ are cyano or aryl which is unsubstituted or has one or more identical or different substituents $R^{Ar}$ and the remaining radicals $R^7$, $R^8$, $R^9$ or $R^{10}$ are hydrogen;

3.2b3) optionally subjecting the compound(s) obtained in step 3.2b2) to at least one separation and/or purification step;

or 4.1) reacting the compounds of the formula (vi) obtained in step 2.1) with a metal cyanide to obtain a compound of the formula (I)

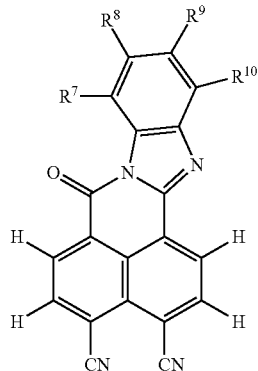

where zero, one or two of the radicals $R^7$, $R^8$, $R^9$ or $R^{10}$ are cyano or aryl which is unsubstituted or has one or more identical or different substituents $R^{Ar}$ and the remaining radicals $R^7$, $R^8$, $R^9$ or $R^{10}$ are hydrogen;

4.2) optionally subjecting the compound(s) of formula I to at least one separation and/or purification step.

13. A cyanated naphthalenebenzimidazole compound of the formula I or a mixture of these according to claim 12, wherein the cyanated napthalenebenzimidazole compound corresponds to a compound of the formula Ia or Ib

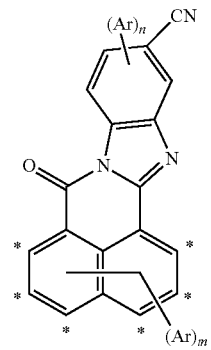

(Ia)

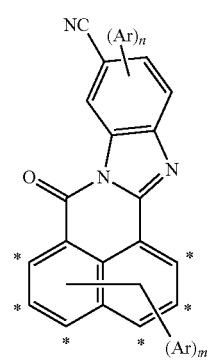

(Ib)

or a mixture of these, in which

Ar is aryl which is optionally mono- or polysubstituted by $R^{Ar}$;

n is 1 or 2, and m is 1 or 2 and where $(Ar)_m$ are at one of the positions indicated with *;

obtained by a process comprising a1) reacting 1,8-naphthalic anhydride with 3,4-diaminobenzonitrile to obtain compounds of the formulae IIa and IIb

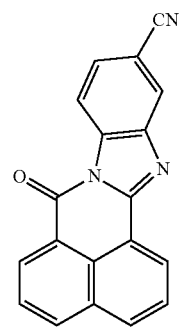

(IIa)

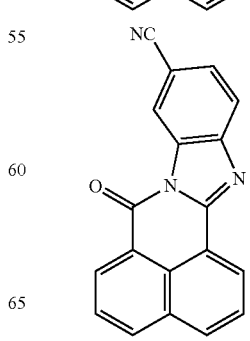

(IIb)

a2) subjecting the compounds of the formulae IIa and IIb obtained in step a1) to a bromination to obtain compounds of the formulae IIIa and IIIb

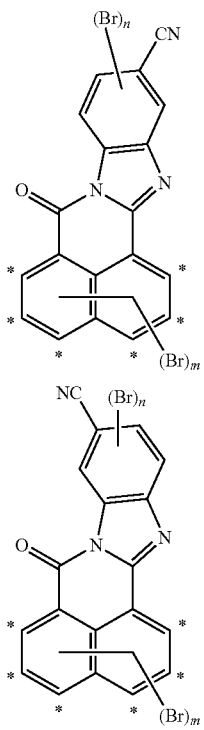

(IIIa)

(IIIb)

in which
n is 1 or 2,
m is 1 or 2 and where $(Br)_m$ are at one of the positions indicated with *;
a3) subjecting the compounds of the formulae IIIa and IIIb obtained in step a2) to a cross-coupling with an organometallic compound of the formula IV Ar-Met  (IV)

in which Ar and Met are as defined in claim 12;
in the presence of a transition metal catalyst to obtain the compounds of the formulae Ia and Ib,
and
a4) optionally subjecting the compounds of the formulae Ia and Ib obtained in step a3) to at least one separation and/or purification step.

14. A cyanated naphthalenebenzimidazole compound of the formula I or a mixture of these according to claim 12, wherein the cyanated napthalenebenzimidazole compound corresponds to a compound formula Ic or Id

(Ic)

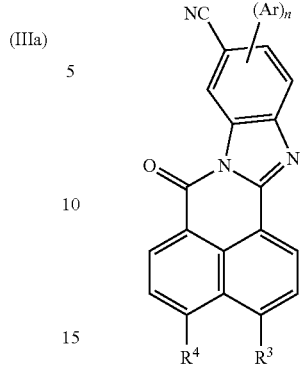

(Id)

or a mixture of these,
in which
$R^3$ is aryl which is unsubstituted or mono- or polysubstituted by $R^{Ar}$;
$R^4$ is aryl which is unsubstituted or mono- or polysubstituted by $R^{Ar}$;
Ar is aryl which is unsubstituted or mono- or polysubstituted by $R^{Ar}$;
$R^{Ar}$ is as defined in claim 1; and
n is 1 or 2,
obtained by a process comprising
b1) reacting 4,5-dihalonaphthalic anhydride of the formula V

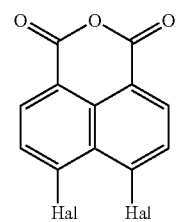

(V)

in which
Hal is bromine or chlorine
with 3,4-diaminobenzonitrile to obtain compounds of the formulae VIa and VIb

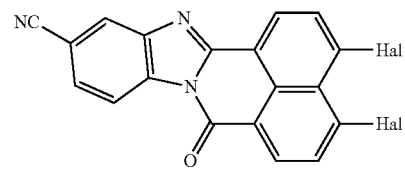

(VIa)

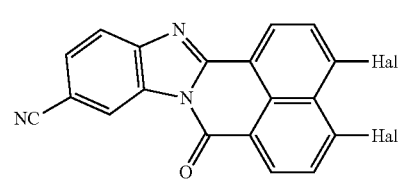

(VIb)

b2) subjecting the compounds of the formulae VIa and VIb obtained in step b1) to a bromination to obtain compounds of the formulae VIIa and VIIb

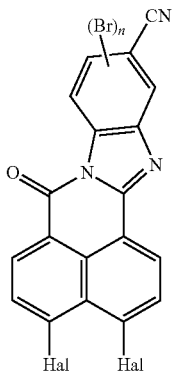
(VIIa)

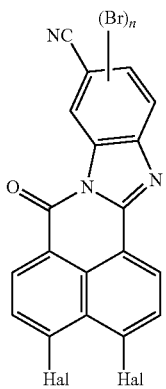
(VIIb)

in which
n is 1 or 2, b3) subjecting the compounds of the formulae VIIa and VIIb obtained in step b2) to a cross-coupling with an organometallic compound of the formula IV Ar-Met (IV)

in which Ar and Met are as defined in claim 12 in the presence of a transition metal catalyst to obtain compounds of the formulae Ic and Id, b4) optionally subjecting the compounds of the formulae Ic and Id obtained in step b3) to at least one separation and/or purification step.

15. A cyanated naphthalenebenzimidazole compound of the formula I or a mixture of these according to claim 12, which corresponds to a compound of the formula Ie or If

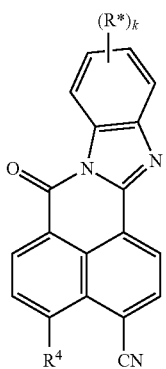
(Ie)

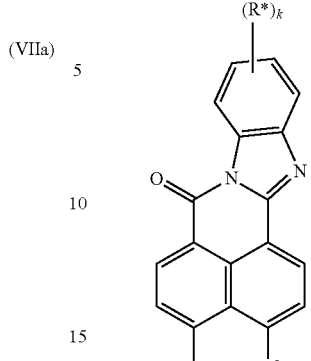
(If)

or a mixture of these,
in which
$R^3$, if present, is aryl which is unsubstituted or mono- or polysubstituted by $R^{Ar}$;
$R^4$, if present is aryl which is unsubstituted or mono- or polysubstituted by $R^{Ar}$;
each $R^*$ is independently cyano or aryl which is unsubstituted or has one or more identical or different substituents $R^{Ar}$;
$R^{Ar}$ is as defined in claim 1; and
k is 0, 1 or 2;
obtained by a process comprising
c1) reacting 4,5-dihalonaphthalic anhydride of the formula V

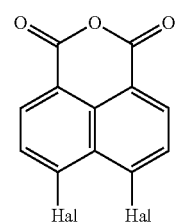
(V)

in which
Hal is bromine or chlorine
with a compound of the formula VIII

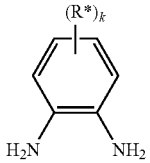
(VIII)

in which $R^*$ is as defined above; and k is 0, 1 or 2,
to obtain compound of the formula IX

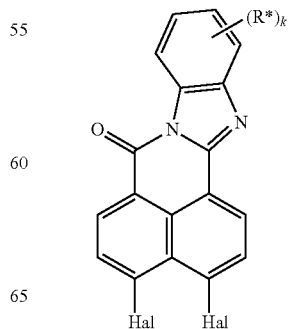
(IX)

c2) subjecting the compound of the formula IX obtained in step c1) to a cross-coupling with an organometallic compound of the formula IV Ar-Met    (IV)

in which Ar and Met are as defined in claim 12 in the presence of a transition metal catalyst to obtain compound(s) of the formulae Xa and/or Xb,

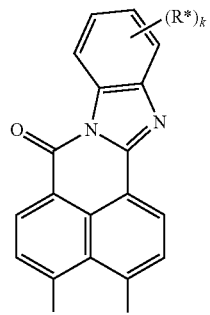

(Xa)

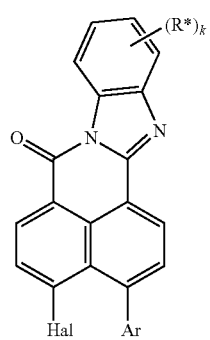

(Xb)

c3) optionally separating the compounds of the formulae Xa and/or Xb obtained in step c2);

c4) reacting the compound(s) of the formulae Xa and/or Xb obtained in step c2) or c3) with a metal cyanide to obtain compounds of the formulae Ie and/or If or c2a) reacting the compound of the formula IX obtained in step c1) with a metal cyanide to obtain compound(s) of the formulae XIa and/or XIb

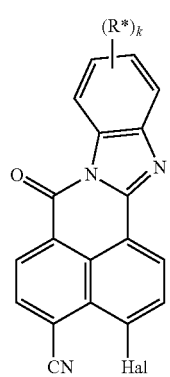

(XIa)

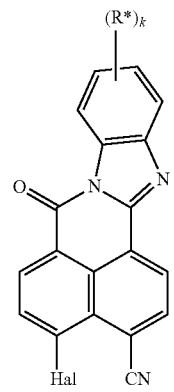

(XIb)

and c3a) subjecting the compound(s) of the formulae XIa and/or XIb obtained in step c2a) to a cross-coupling with an organometallic compound of the formula IV Ar-Met    (IV)

in which Ar and Met are as defined in claim 12, in the presence of a transition metal catalyst to obtain compound(s) of the formula(e) Ie and/or If, c5) optionally subjecting the compound(s) of the formula (e) Ie and/or If obtained in step c3) or c3a) to at least one separation and/or purification step.

16. A cyanated naphthalenebenzimidazole compound of the formula I according to claim 12, wherein the cyanated naphthalenebenzimidazole compound corresponds to a compound of the formula Ig

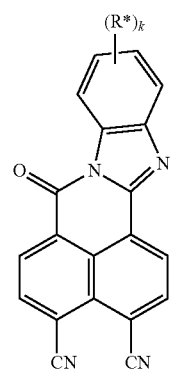

(Ig)

in which each R* is independently cyano or aryl which is unsubstituted or has one or more identical or different substituents $R^{Ar}$, where $R^{Ar}$ is as defined in claim 1;

k is 0, 1 or 2;

obtained by a process comprising d1) reacting a compound of the formula IX

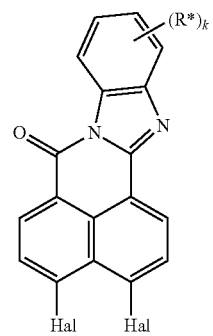

(IX)

in which

R* is as defined above, and k is 0, 1, or 2, with a metal cyanide to obtain compounds of the formula Ig, and d2) optionally subjecting the compounds of the formula Ig obtained in step d1) to at least one separation and/or purification step.

17. A cyanated naphthalenebenzimidazole compound of the formula I or a mixture of these according to claim 12, wherein the cyanated naphthalenebenzimidazole compound corresponds to a compound Ih, Ii, Ik or Im

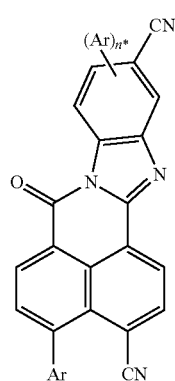
(Ih)

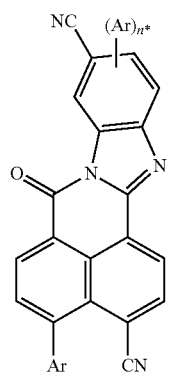
(Ii)

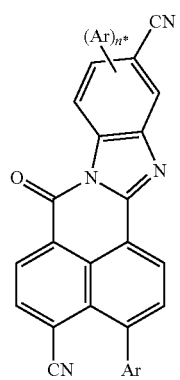
(Ik)

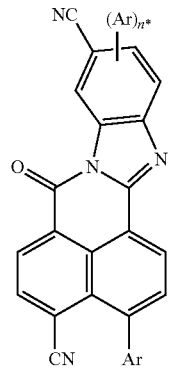
(Im)

or a mixture of these,
in which
Ar is aryl which is unsubstituted or mono- or polysubstituted by $R^{Ar}$ and $R^{Ar}$ is as defined in claim 1; and
n* is 0, 1 or 2;
obtained by a process comprising
e1) subjecting the compounds of the formulae VIIa and VIIb

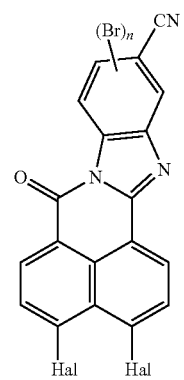
(VIIa)

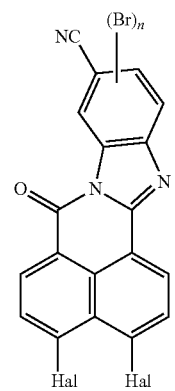
(VIIb)

in which
n is 1 or 2,
to a substitution reaction, wherein one Hal and each bromine atom is substituted by aryl which is unsubstituted or has one or more identical or different substituents $R^{Ar}$,
or
subjecting the compounds of the formulae (VIIa) and (VIIb) to a substitution reaction, wherein one Hal is substituted by aryl, and a part of the bromine atoms attached to the benzene ring of the benzimidazole moiety are substituted by aryl and the other bromine atoms that are not substituted by aryl, are substituted by hydrogen, where aryl is unsubstituted or has one or more identical or different substituents $R^{Ar}$, by cross-coupling with an organometallic compound of the formula IV Ar-Met  (IV)

in which
Ar and Met are as defined in claim 12
in the presence of a transition metal catalyst to obtain compounds of the formulae XIIa, XIIb, XIIc and XIId

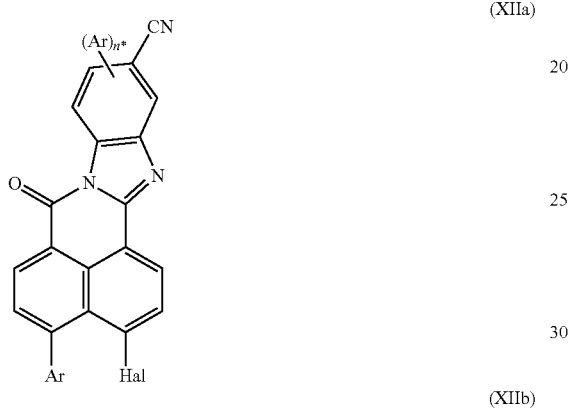
(XIIa)

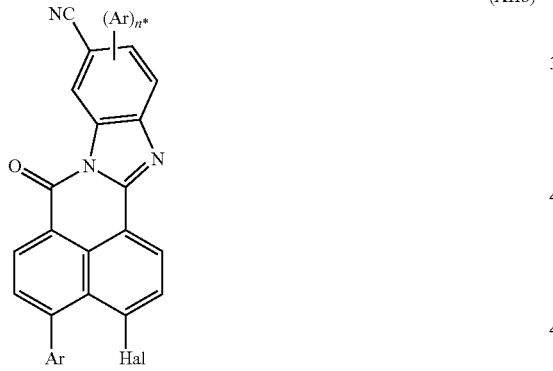
(XIIb)

(XIIc)

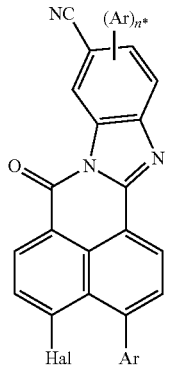
(XIId)

where
n* is 0, 1 or 2; and
Ar is as defined above;

e2) optionally separating the compounds of the formulae (XIIa), (XIIb), (XIIc) and (XIId) to obtain a mixture of the compounds of formulae (XIIa) and (XIIb) and a mixture of the compounds of the formulae (XIIc) and (XIId);

e3) reacting the compounds obtained in step e1) or e2) with a metal cyanide to obtain compounds of the formulae Ih, Ii, and/or Ik and Im;

e4) optionally subjecting the compound(s) of the formula (e) Ih, Ii and/or Ik or Im obtained in step e3) to at least one separation and/or purification step.

\* \* \* \* \*